US012807965B2

(12) United States Patent
Saeki

(10) Patent No.: US 12,807,965 B2
(45) Date of Patent: Nov. 24, 2026

(54) SENDAI VIRAL VECTOR ENCODING A DEGRON-P FUSION PROTEIN

(71) Applicant: ID PHARMA CO., LTD., Tokyo (JP)

(72) Inventor: Koichi Saeki, Tokyo (JP)

(73) Assignee: ID PHARMA CO., LTD., Tokyo (JP)

( * ) Notice: Subject to any disclaimer, the term of this patent is extended or adjusted under 35 U.S.C. 154(b) by 168 days.

(21) Appl. No.: 15/547,544

(22) PCT Filed: Nov. 13, 2015

(86) PCT No.: PCT/JP2015/081921

§ 371 (c)(1),
(2) Date: Dec. 15, 2017

(87) PCT Pub. No.: WO2016/125364

PCT Pub. Date: Aug. 11, 2016

(65) Prior Publication Data

US 2018/0195085 A1 Jul. 12, 2018

(30) Foreign Application Priority Data

Feb. 2, 2015 (JP) ................................ 2015-018844

(51) Int. Cl.

*A01N 63/00* (2020.01)
*C12N 7/04* (2006.01)
*C12N 15/85* (2006.01)
*C12N 15/86* (2006.01)

(52) U.S. Cl.

CPC ............... *C12N 15/85* (2013.01); *C12N 7/04* (2013.01); *C12N 15/86* (2013.01); *C12N 2760/18821* (2013.01); *C12N 2760/18822* (2013.01); *C12N 2760/18843* (2013.01); *C12N 2760/18861* (2013.01); *C12N 2830/42* (2013.01); *C12N 2830/60* (2013.01)

(58) Field of Classification Search

None

See application file for complete search history.

(56) References Cited

U.S. PATENT DOCUMENTS

| | | | | |
|---|---|---|---|---|
| 2009/0215169 | A1 | 8/2009 | Wandless et al. | |
| 2011/0287538 | A1 | 11/2011 | Fusaki et al. | |
| 2012/0115232 | A1 | 5/2012 | Kanemaki et al. | |
| 2012/0178168 | A1 | 7/2012 | Wandless et al. | |
| 2013/0210150 | A1 * | 8/2013 | Ban ...................... | C12N 5/0696 435/456 |
| 2015/0337334 | A1 | 11/2015 | Fusaki et al. | |
| 2016/0177337 | A1 | 6/2016 | Fusaki et al. | |

FOREIGN PATENT DOCUMENTS

| | | | | |
|---|---|---|---|---|
| EP | 1935978 | A1 | 6/2008 | |
| EP | 2639297 | A1 | 9/2013 | |
| JP | 2009-136154 | A | 6/2009 | |
| JP | 2011-101639 | A | 5/2011 | |
| WO | WO-99/54348 | A1 | 10/1999 | |
| WO | WO-2004/025264 | A2 | 3/2004 | |
| WO | WO-2007/032555 | A1 | 3/2007 | |
| WO | WO-2008/007581 | A1 | 1/2008 | |
| WO | WO-2008133206 | A1 * | 11/2008 | ............... C12N 7/00 |
| WO | WO-2010/008054 | A1 | 1/2010 | |
| WO | WO-2010/125620 | A1 | 11/2010 | |
| WO | WO-2012/029770 | A1 | 3/2012 | |
| WO | WO-2012/063817 | A1 | 5/2012 | |

OTHER PUBLICATIONS

Garcin et al Journal of Virology, 78, 8799-8811 (Year: 2004).*
Garcin et al Journal of Virology, 78(16), 8799-8811 (Year: 2004).*
Nishimura et al Stem Cell Report, 3(5), 915-929 (Year: 2014).*
Ban et al Proc, Natl. Acad. Sci, USA, 108(34), 14234-14239 (Year: 2011).*
Irie et al PLoS One, 5(5): e10719, 1-12 (Year: 2010).*
Nishimura et al , JBC, 286, 4760-4771 (Year: 2011).*
Abe et al., "Ex vivo expansion of human HSCs with Sendai virus vector expressing HoxB4 assessed by sheep in utero transplantation," Exp Hematol. 39(1):47-54 (2011).
Ban et al., "Efficient generation of transgene-free human induced pluripotent stem cells (IPSCs) by temperature-sensitive Sendai virus vectors," Proc Natl Acad Sci USA 108(34): 14234-9 (2011) (12 pages).
Bitzer et al., "Sendai virus vectors as an emerging negative-strand RNA viral vector system," J Gene Med. 5(7):543-53 (2003).
Garcin et al., "A short peptide at the amino terminus of the Sendai virus C protein acts as an independent element that induces STAT1 instability," J Virol. 78(16):8799-811 (2004).

(Continued)

*Primary Examiner* — Michael C Wilson

(74) *Attorney, Agent, or Firm* — Clark & Elbing LLP

(57) ABSTRACT

The present invention addresses the problem of providing an improved negative-strand RNA viral vector enabling transient high expression of a gene carried by the vector, and quick removal of the vector after the expression, and the use thereof. It was found that if a degron is added to a P-protein possessed by a negative-strand RNA viral vector, high-level expression of a gene carried by the vector is transiently induced after introduction of the vector, and thereafter, the vector can be quickly removed in a manner dependent on the degron. In particular, if the degron is added to a temperature-sensitive P-protein, the vector can be removed to a level below the detection limit within two weeks after cells are infected with the vector. Since the present invention is useful for transiently expressing a transcription factor, such as a reprogramming factor or the like, in target cells, and then quickly removing the vector, the present invention is expected to be applied in cell therapy and regenerative medicine.

11 Claims, 26 Drawing Sheets

Specification includes a Sequence Listing.

(56) References Cited

OTHER PUBLICATIONS

Griesenbach et al., "Sendai virus for gene therapy and vaccination," Curr Opin Mol Ther. 7(4):346- 52 (2005).
Nishimura et al., "An auxin-based degron system for the rapid depletion of proteins in nonplant cells," Nat Methods. 6(12):917-22 (2009) (28 pages).
Nishimura et al., "Manipulation of KLF4 expression generates iPSCs paused at successive stages of reprogramming," Stem Cell Reports. 3(5):915-29 (2014) (29 pages).
International Search Report for International Patent Application No. PCT/JP2015/081921, mailed Feb. 16, 2016 (6 pages, English language translation provided).
Written Opinion of the International Searching Authority for International for International Patent Application No. PCT/JP2015/081921, mailed Feb. 16, 2016 (15 pages, English language translation provided).
International Preliminary Report on Patentability for International Patent Application No. PCT/JP2015/081921, issued Aug. 8, 2017 (17 pages, English language translation provided).
Noda, "Orthomyxoviruses," VIRUS(UIRUSU). 62(2):219-28 (2012) (24 pages) (English language translation provided).
Takada, "Filoviruses," VIRUS(UIRUSU). 62(2):197-208 (2012) (30 pages) (English language translation provided).
Yoshimatsu et al., "Bunyavirus and its ecology," VIRUS(UIRUSU). 62(2):239-50 (2012) (30 pages) (English language translation provided).

* cited by examiner

[Fig. 1]
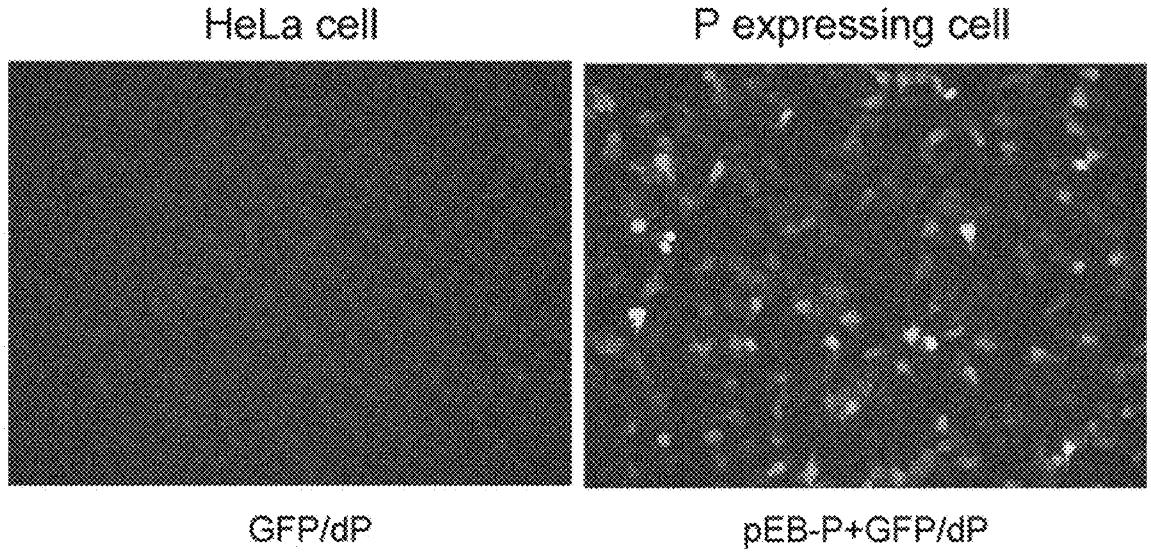
[Fig. 2]
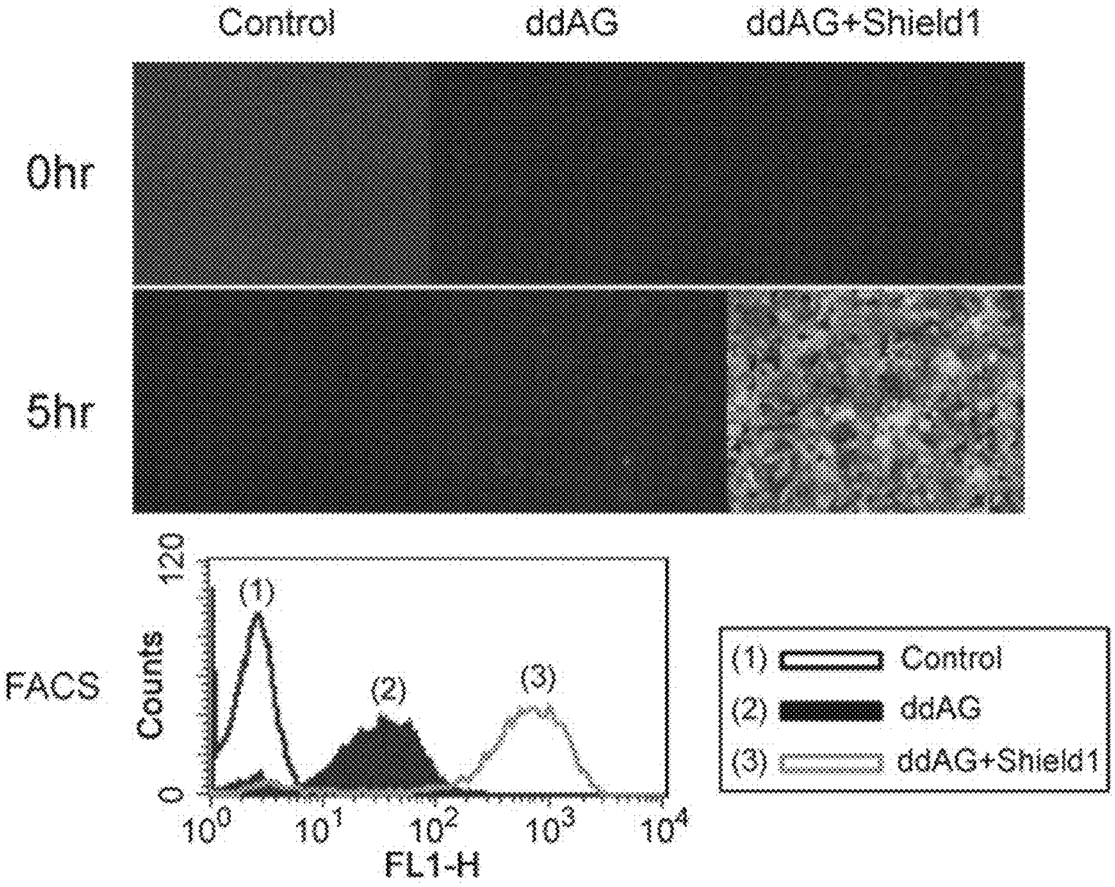

[Fig. 3]
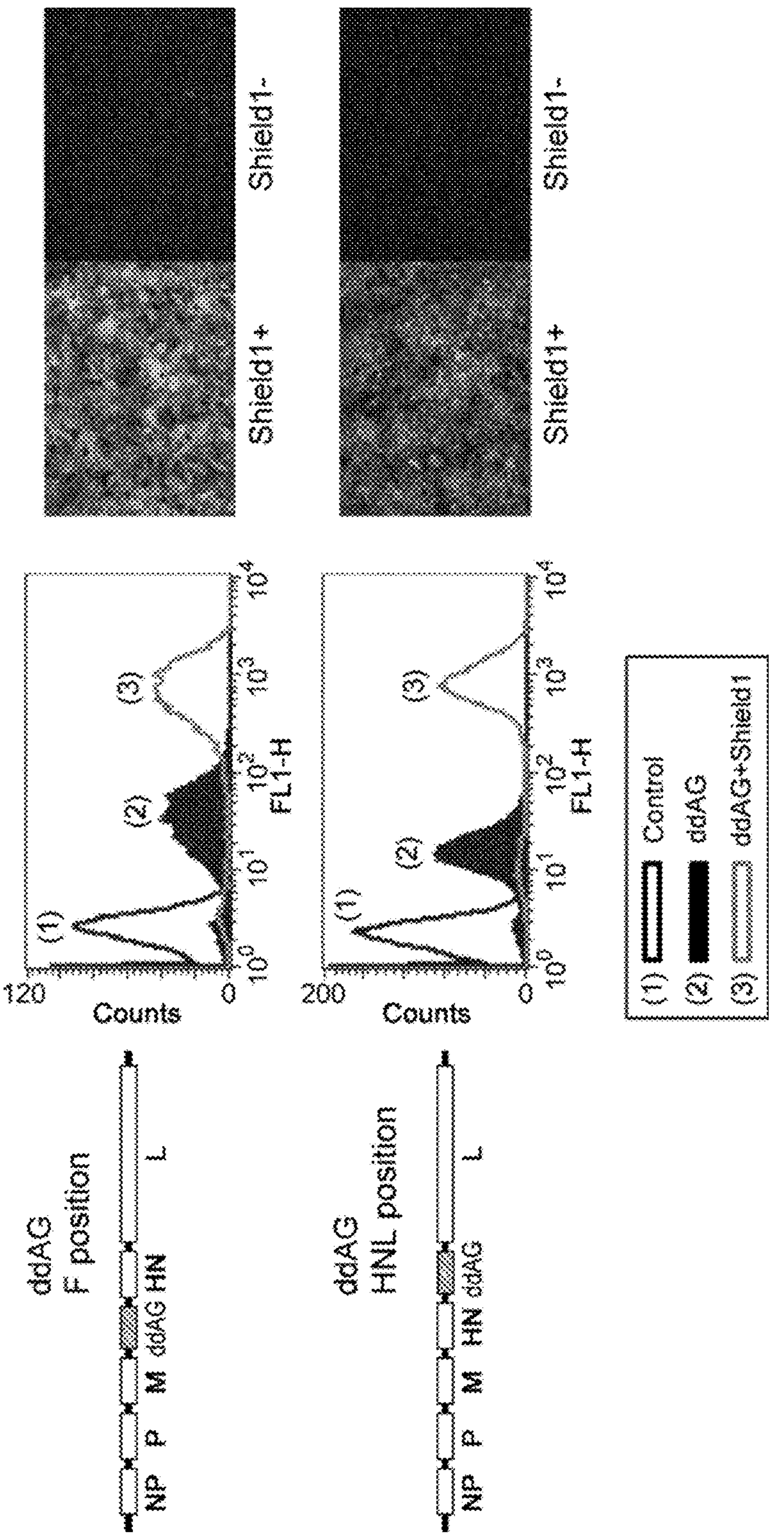

[Fig. 4]
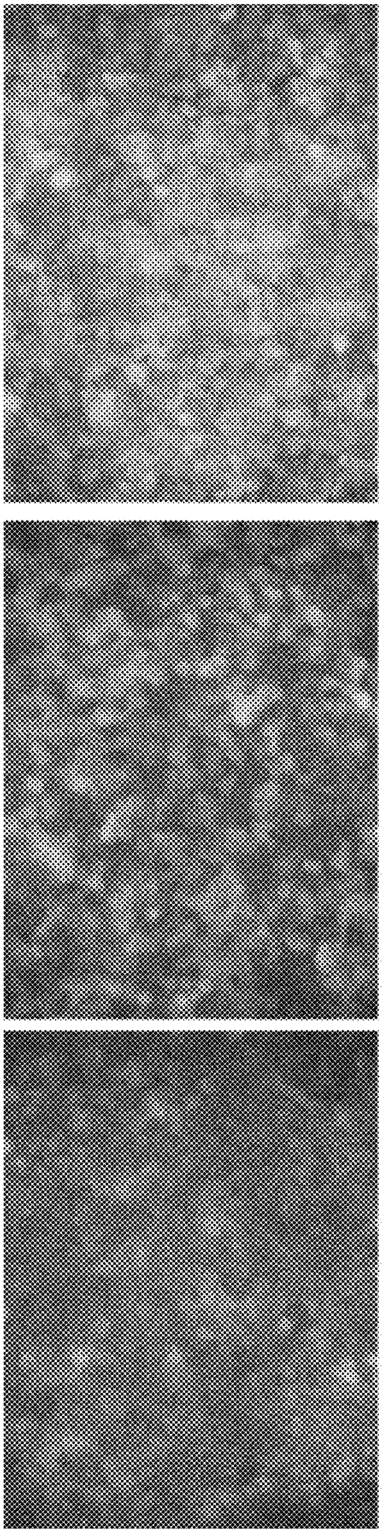
d4GFP
d2GFP
d1GFP

[Fig. 5]
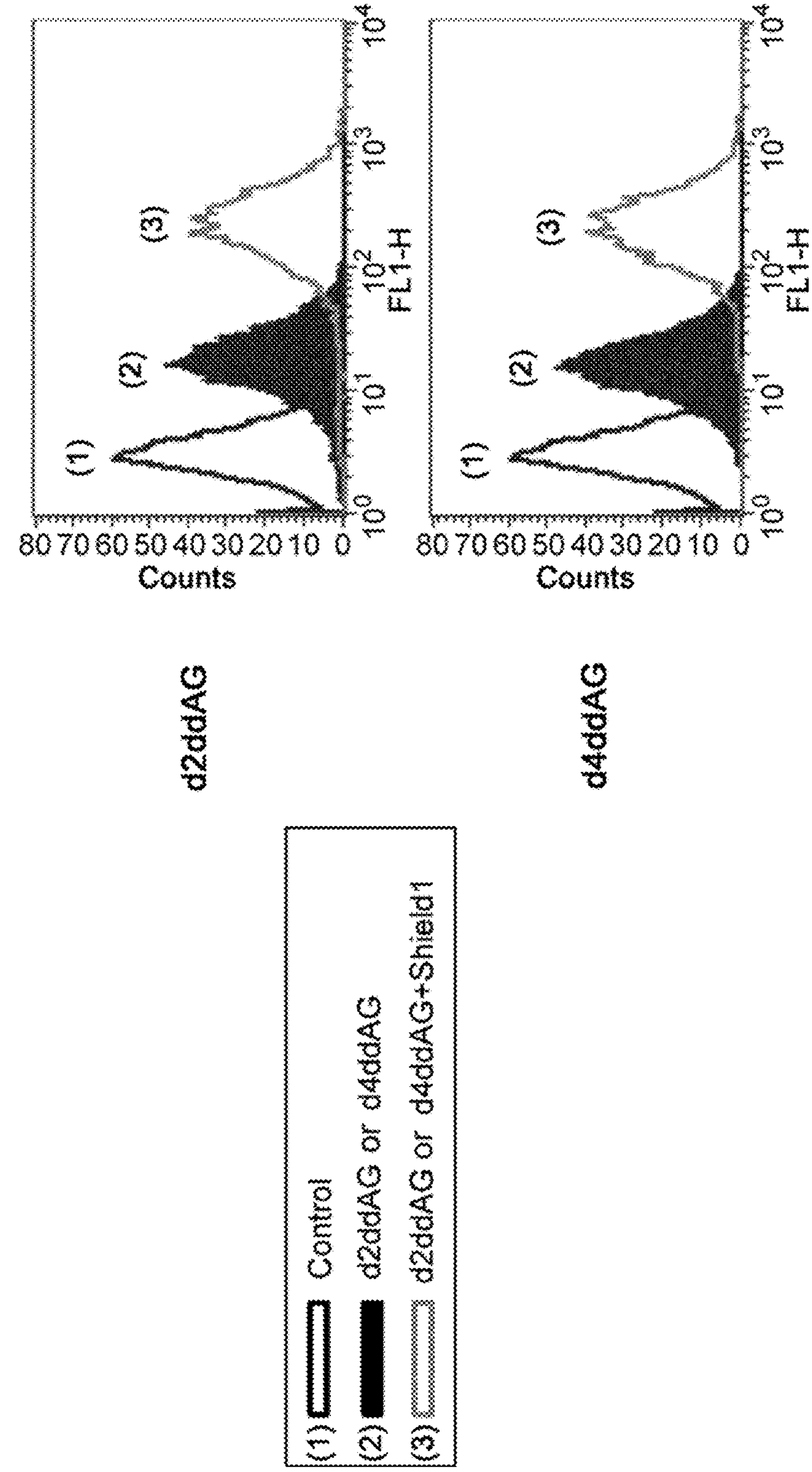

[Fig. 6]
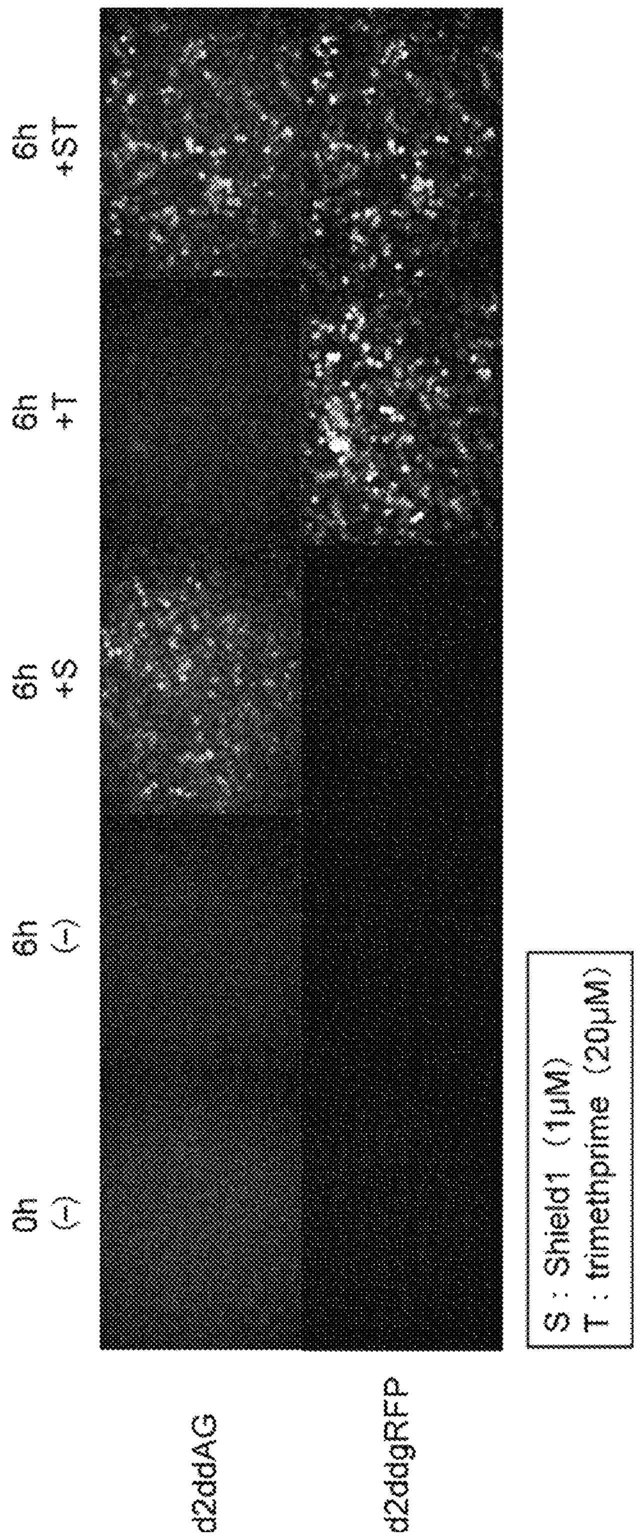

[Fig. 7]
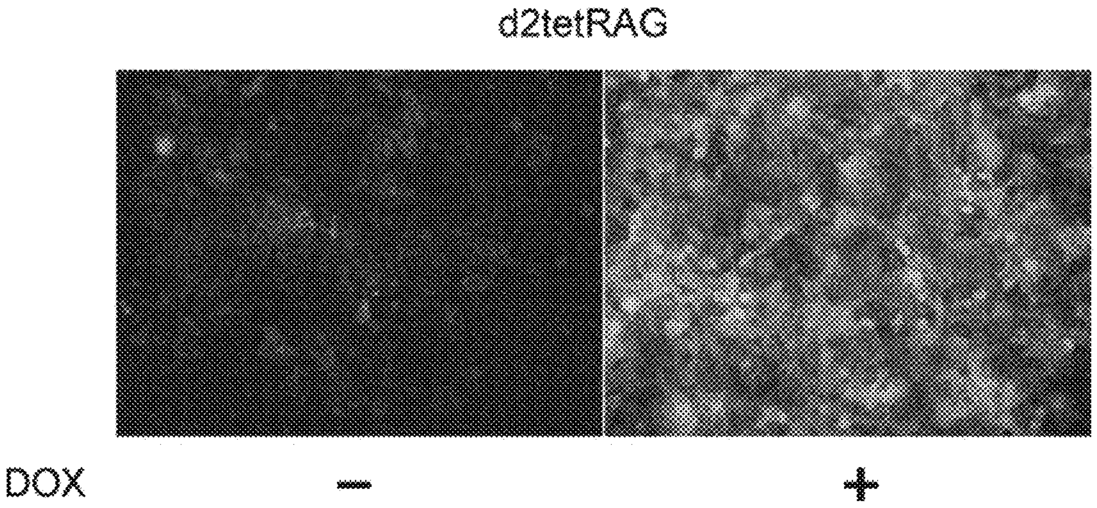
[Fig. 8]
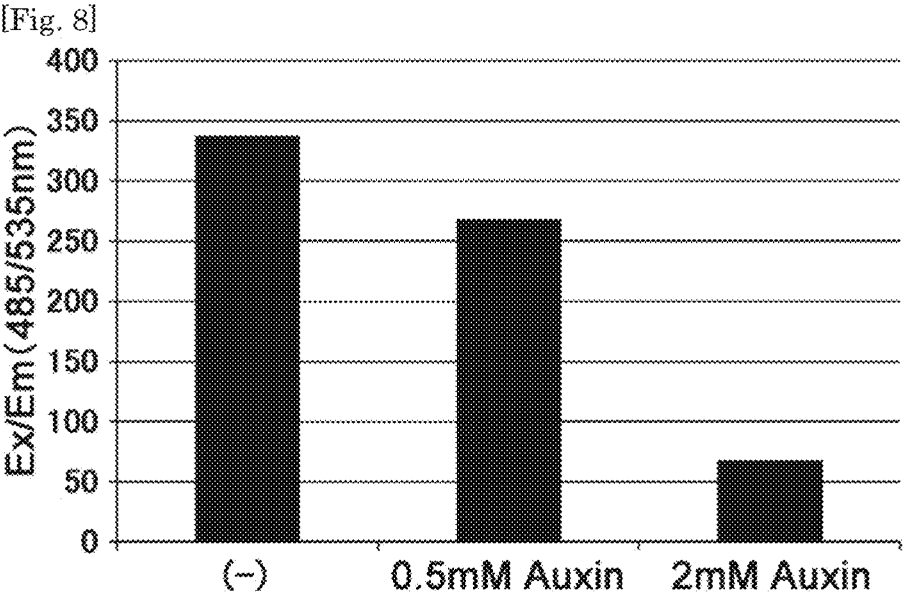
[Fig. 9]
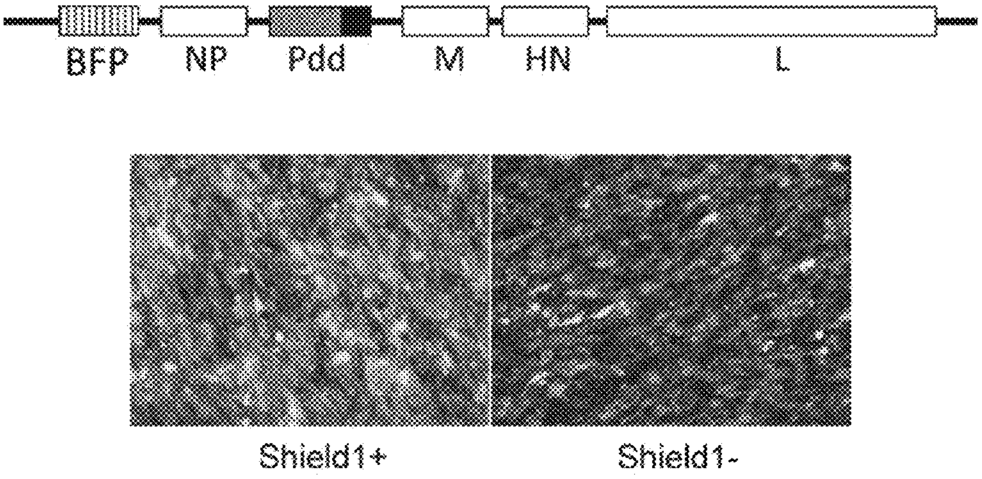

[Fig.10]
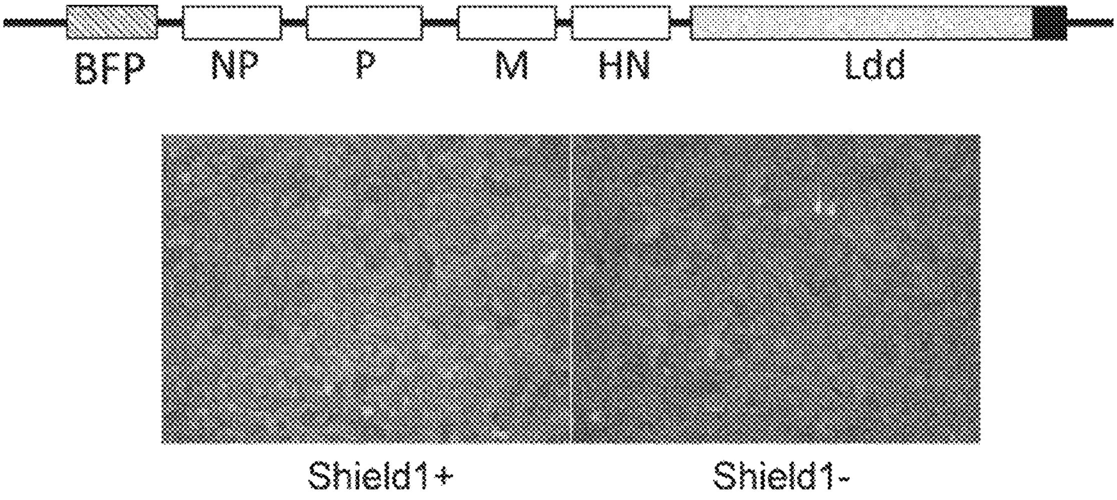
[Fig.11]
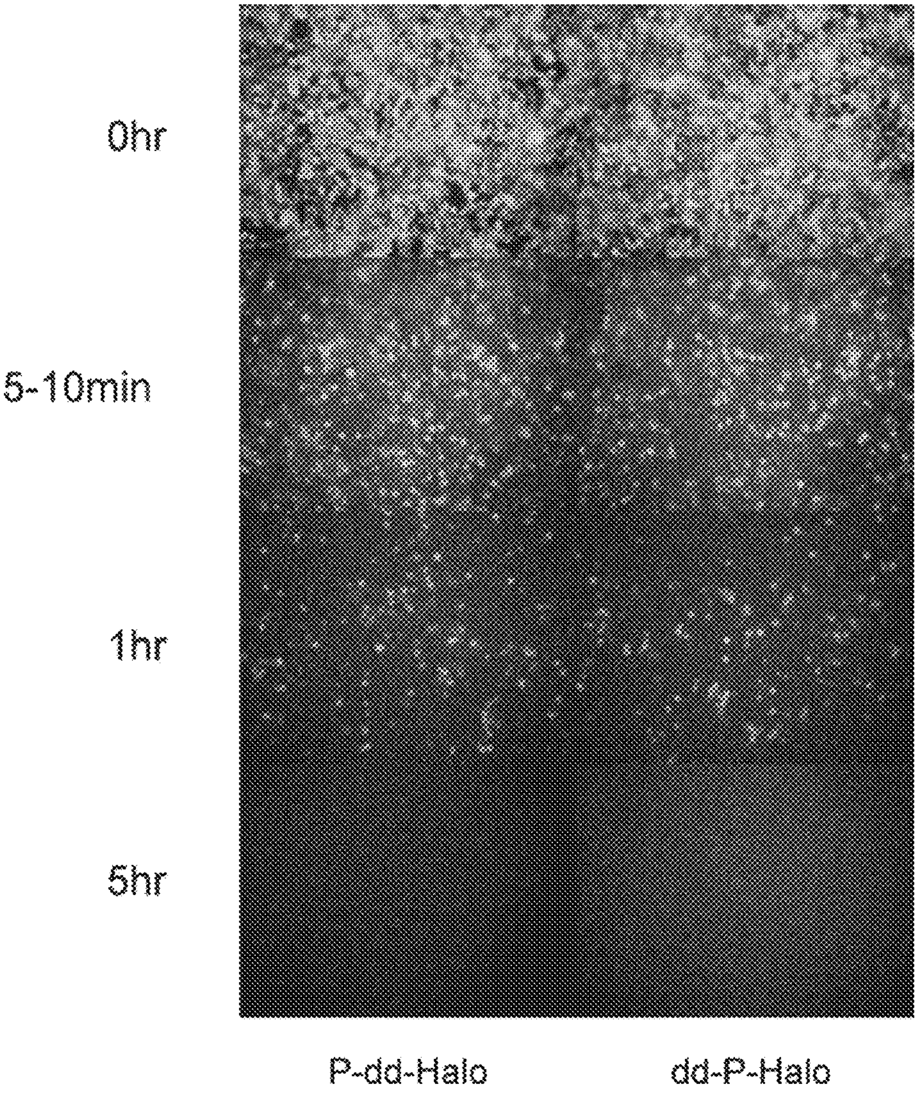

[Fig.12]
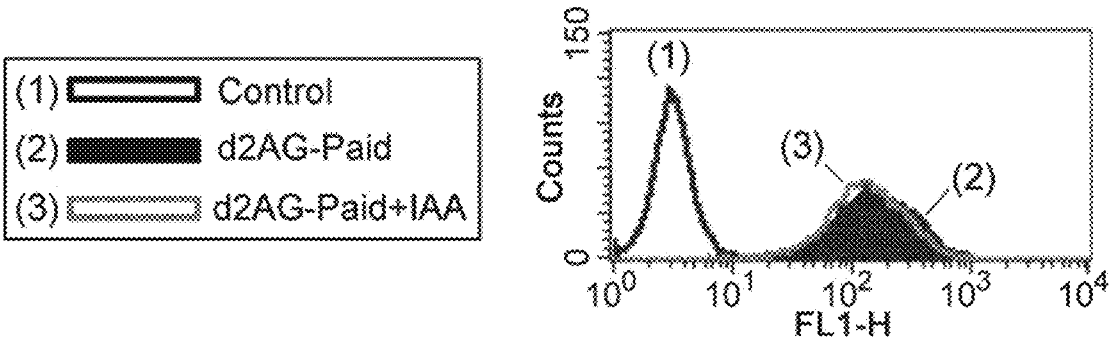
| | Median |
|---|---|
| d2AG-Paid | : 149.89 |
| d2AG-Paid+IAA | : 126.35 |

[Fig.13]
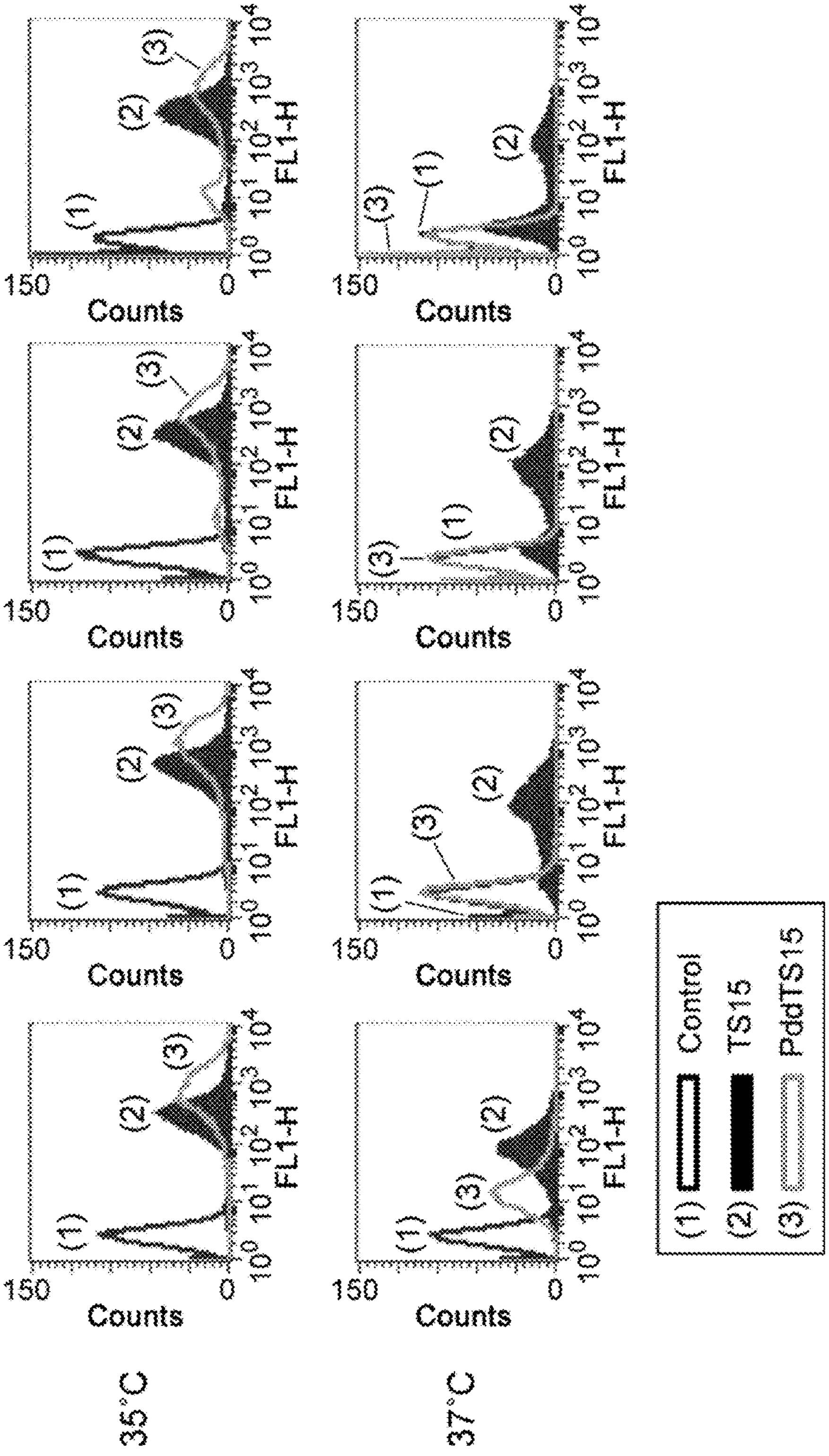

[Fig.14]
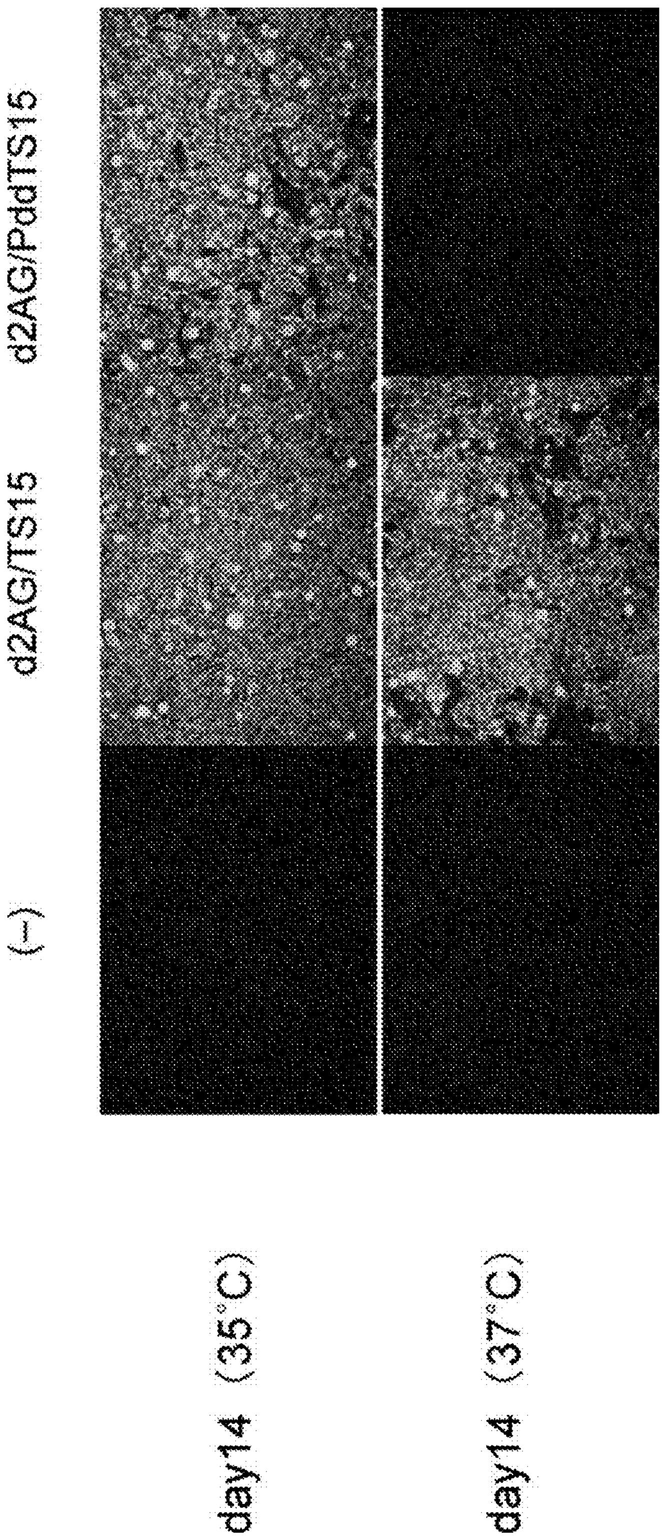

[Fig.15]
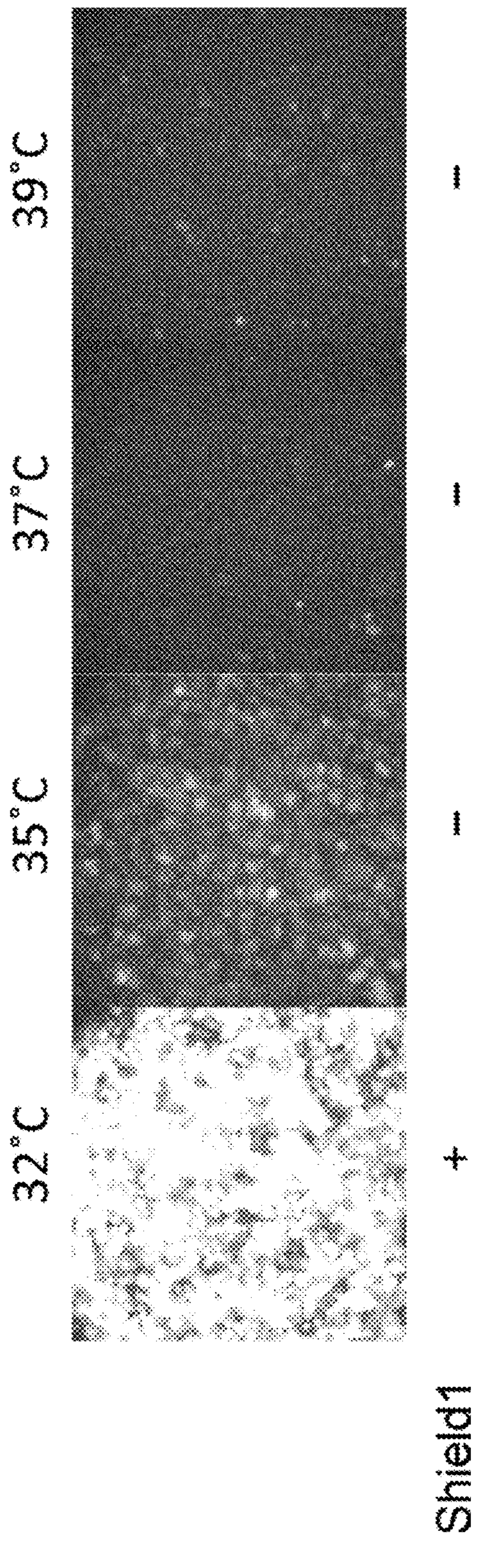

[Fig.16]
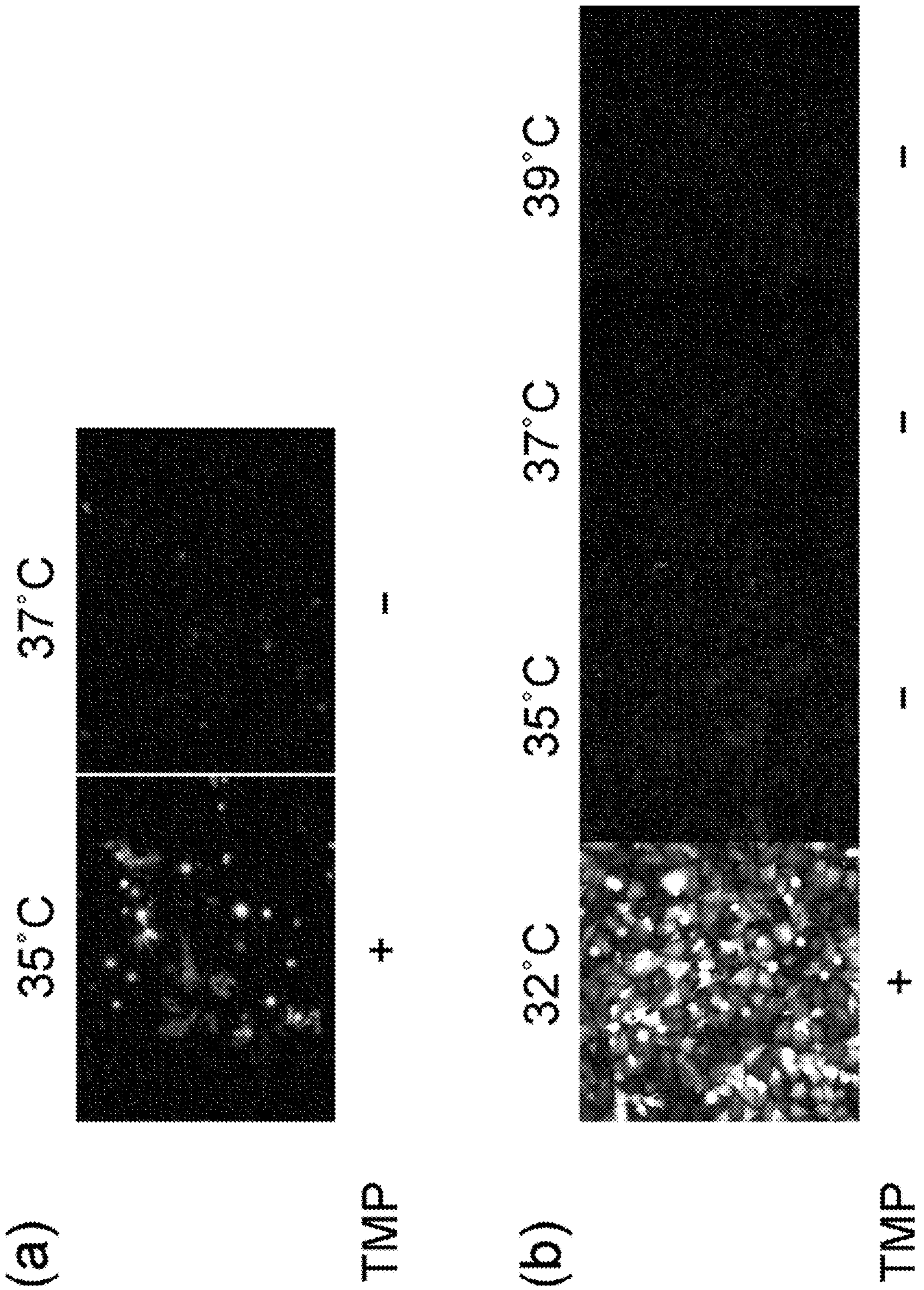

[Fig.17]
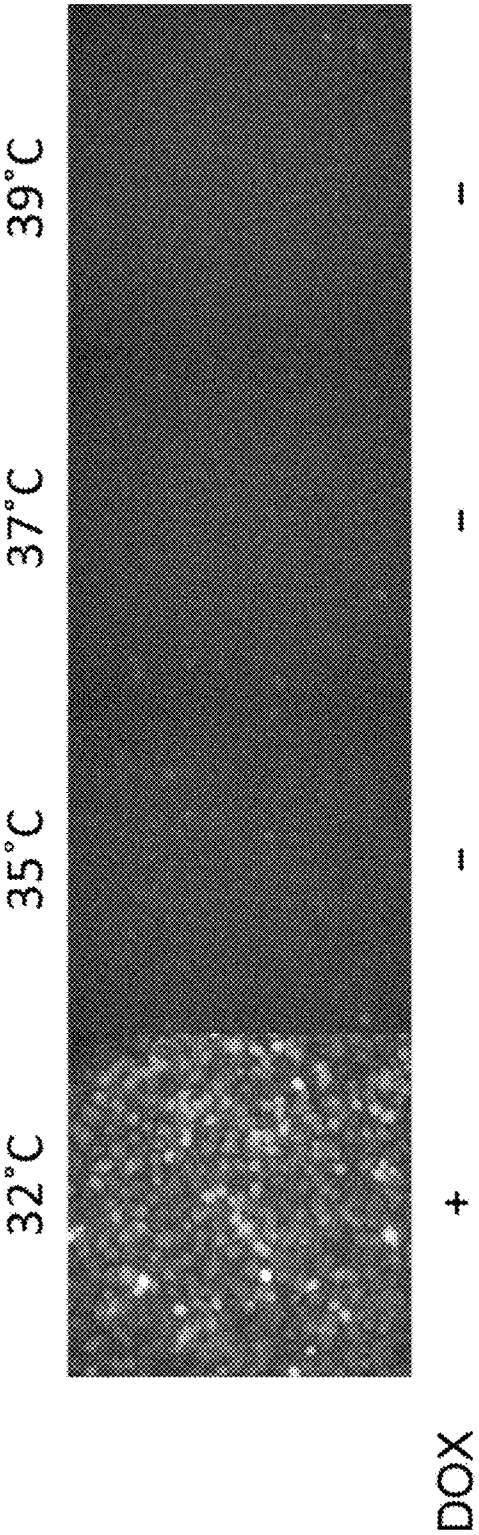

[Fig.18]
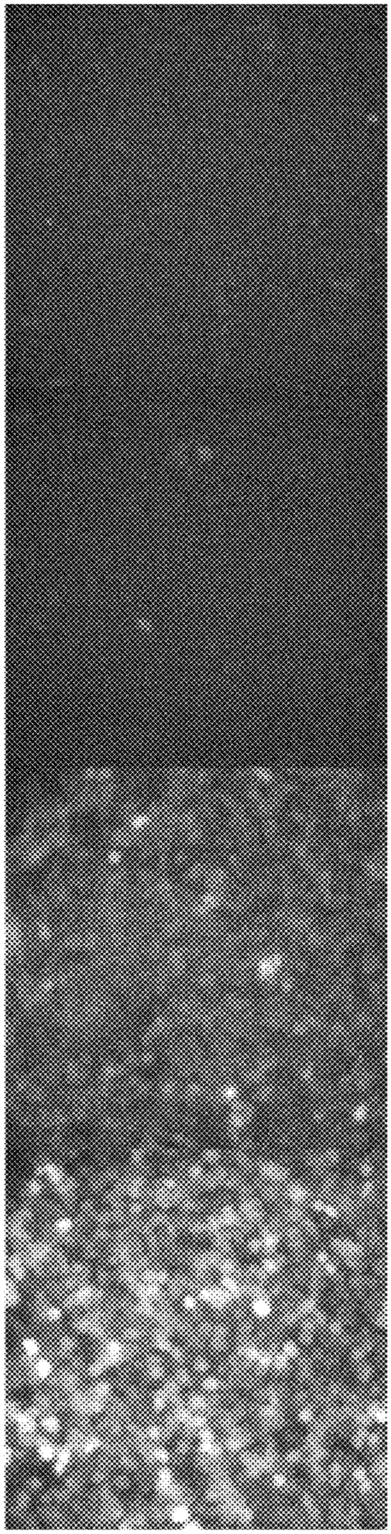

[Fig.19]
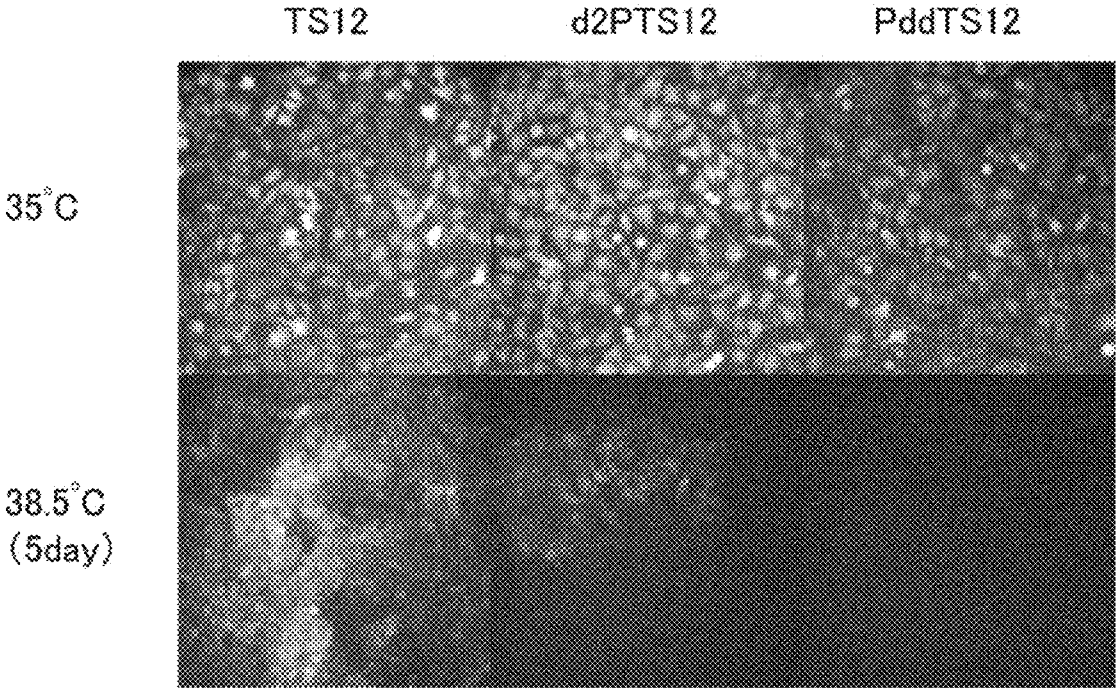

[Fig.20]
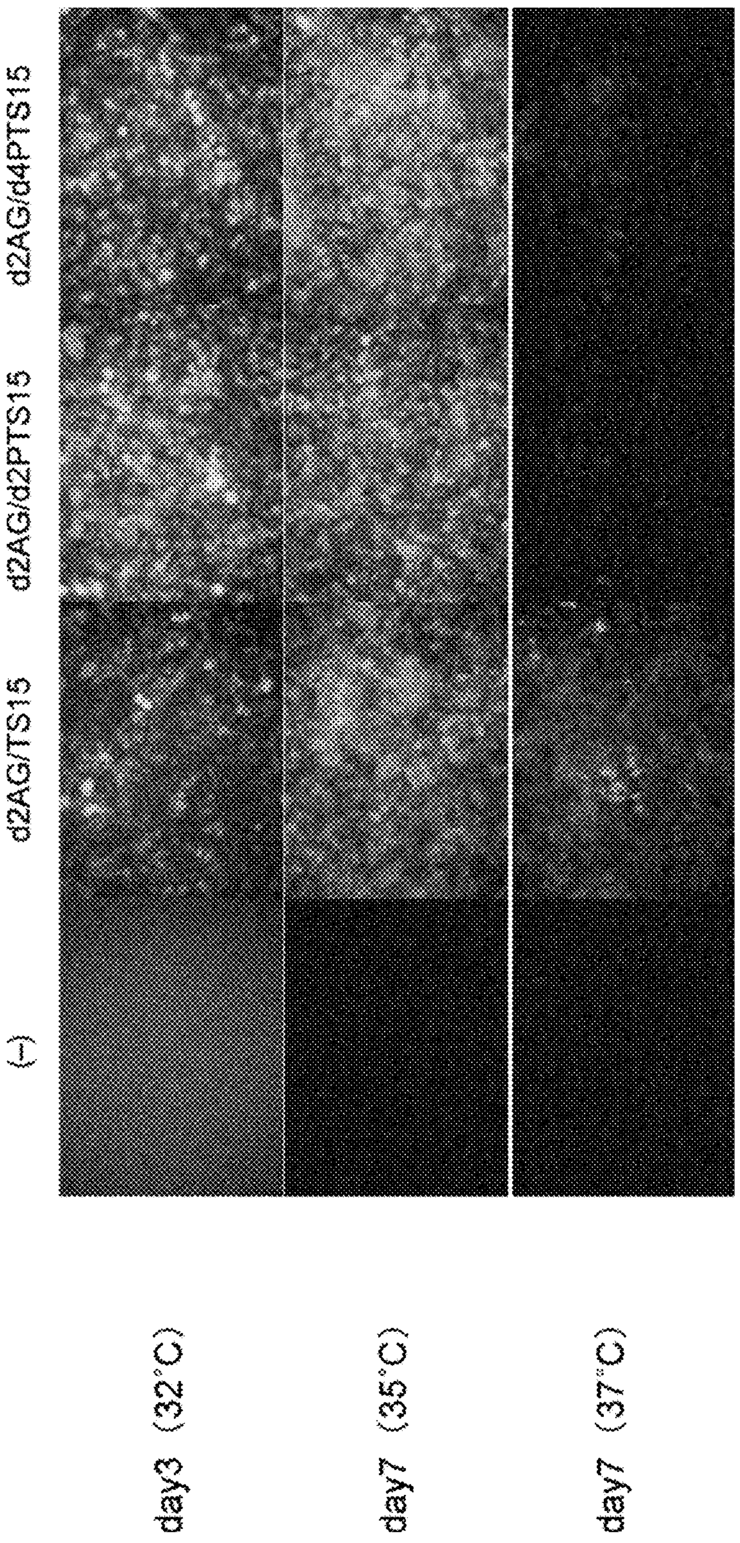

[Fig.21]
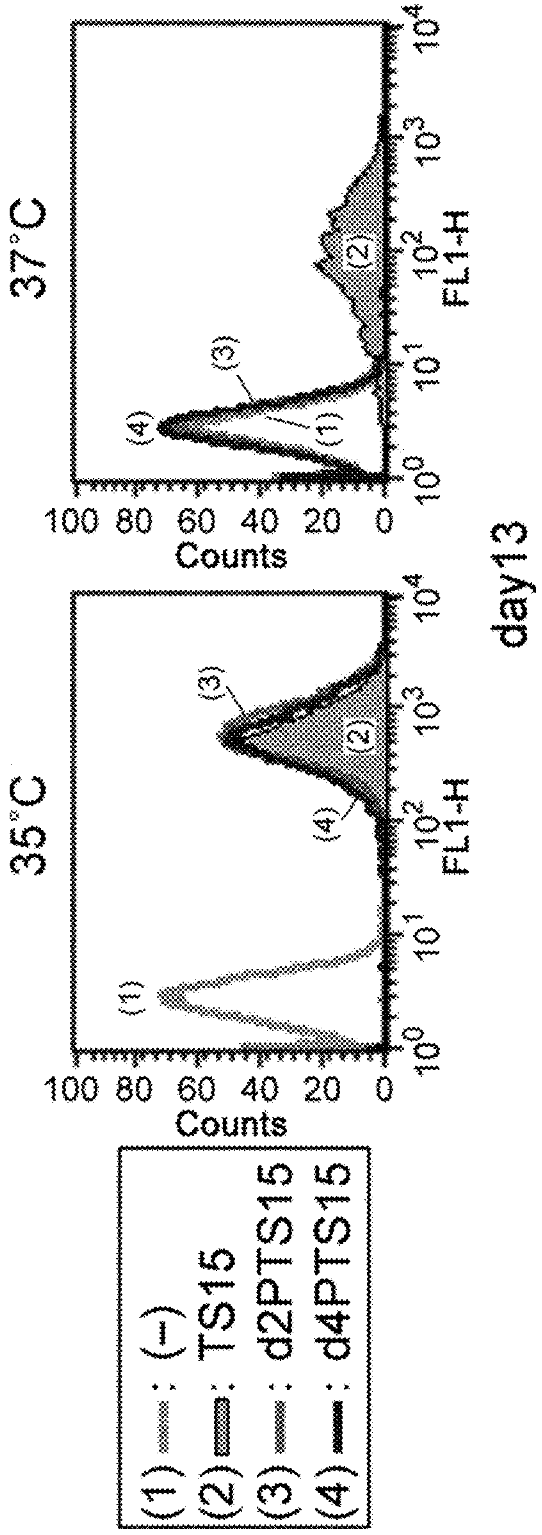

[Fig.22]
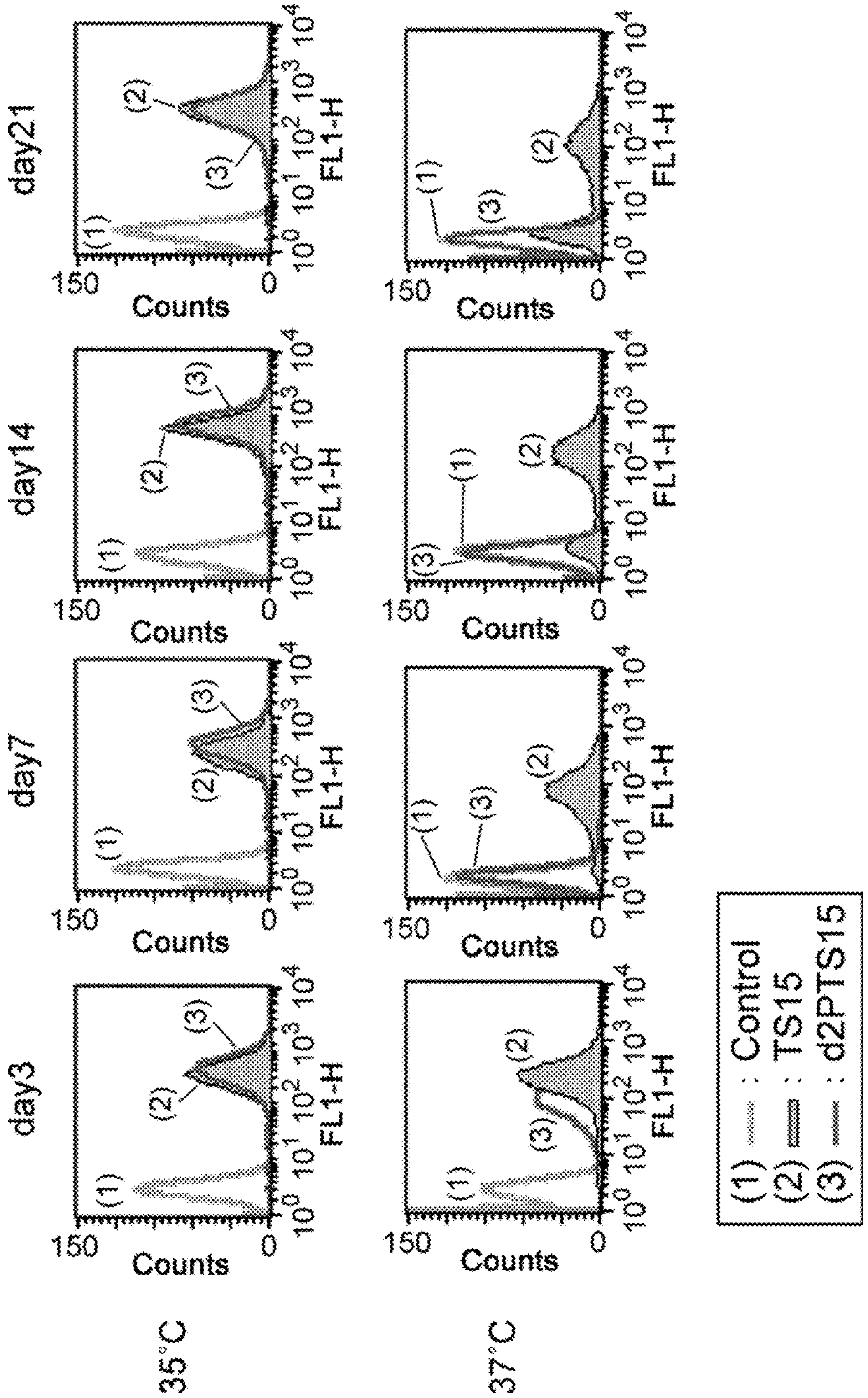

[Fig.23]
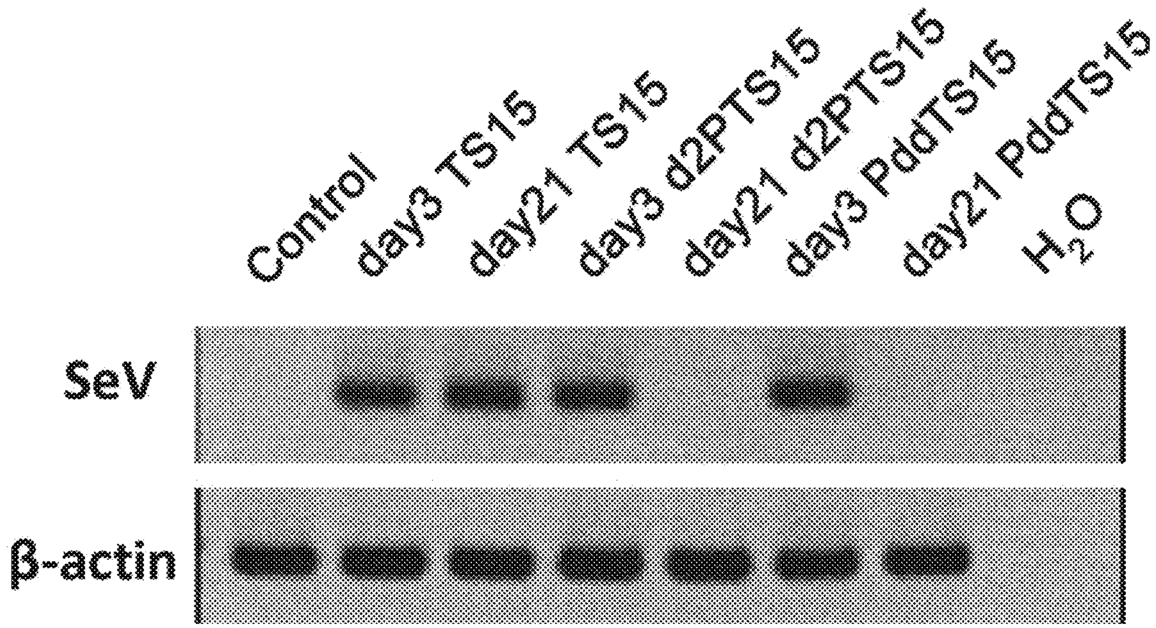
[Fig.24]
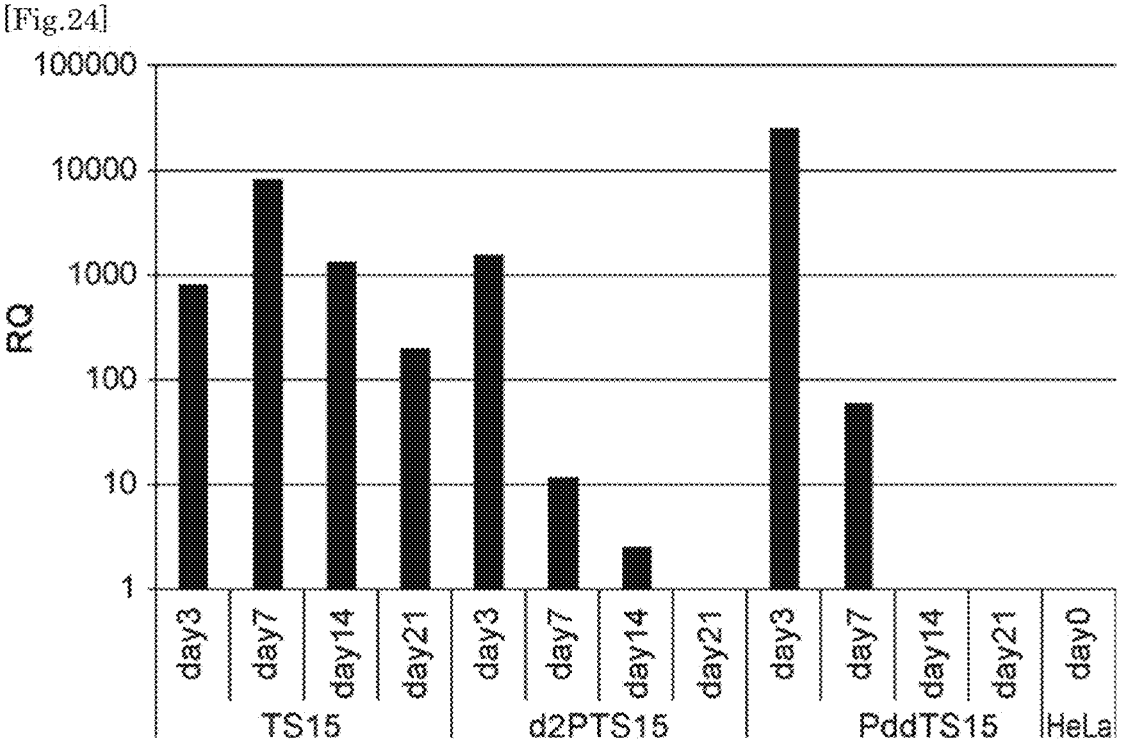
[Fig.25]
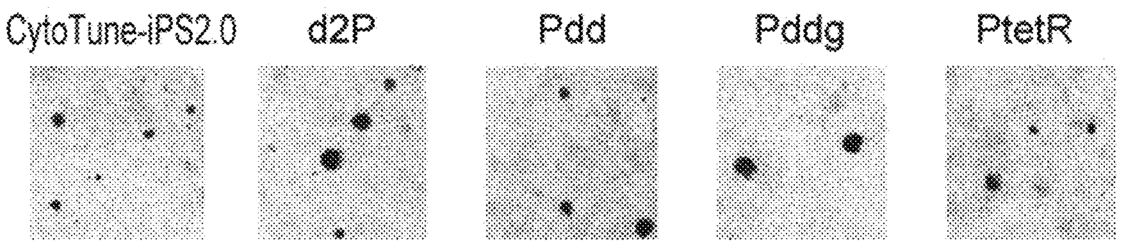

[Fig.26]
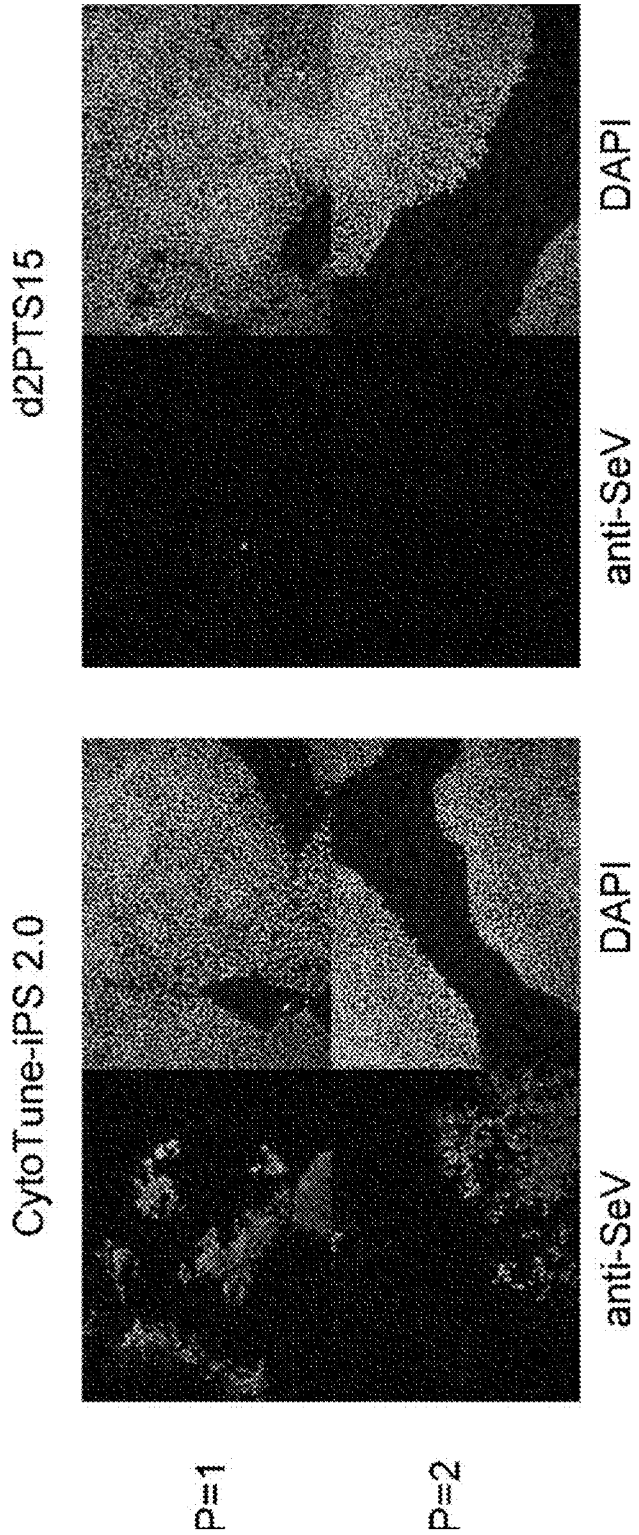

[Fig.27]
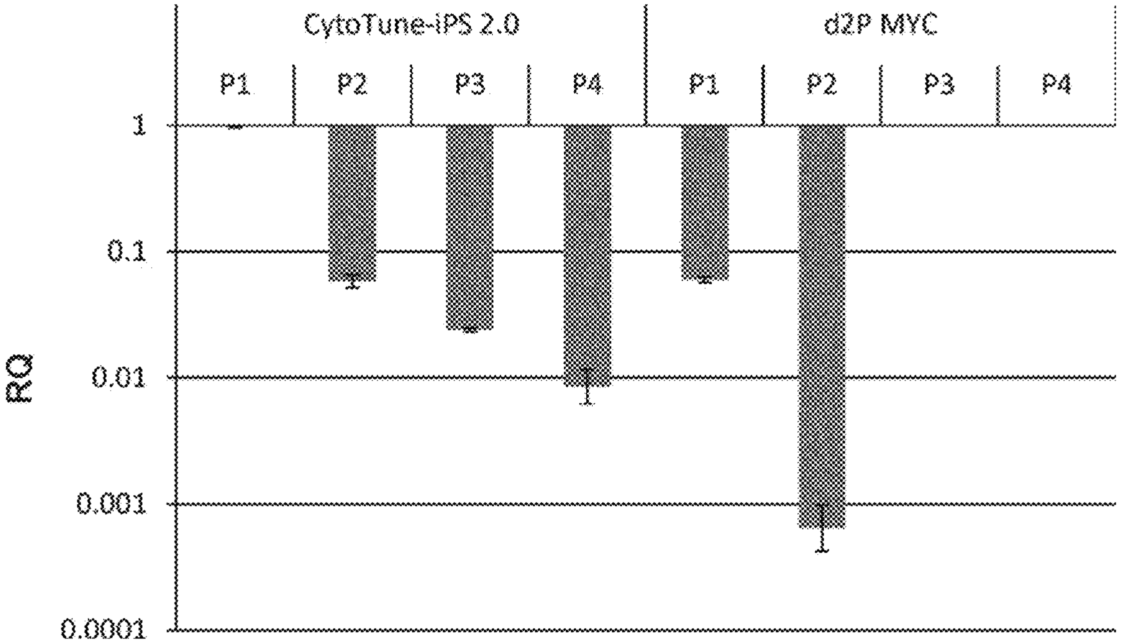
[Fig.28]
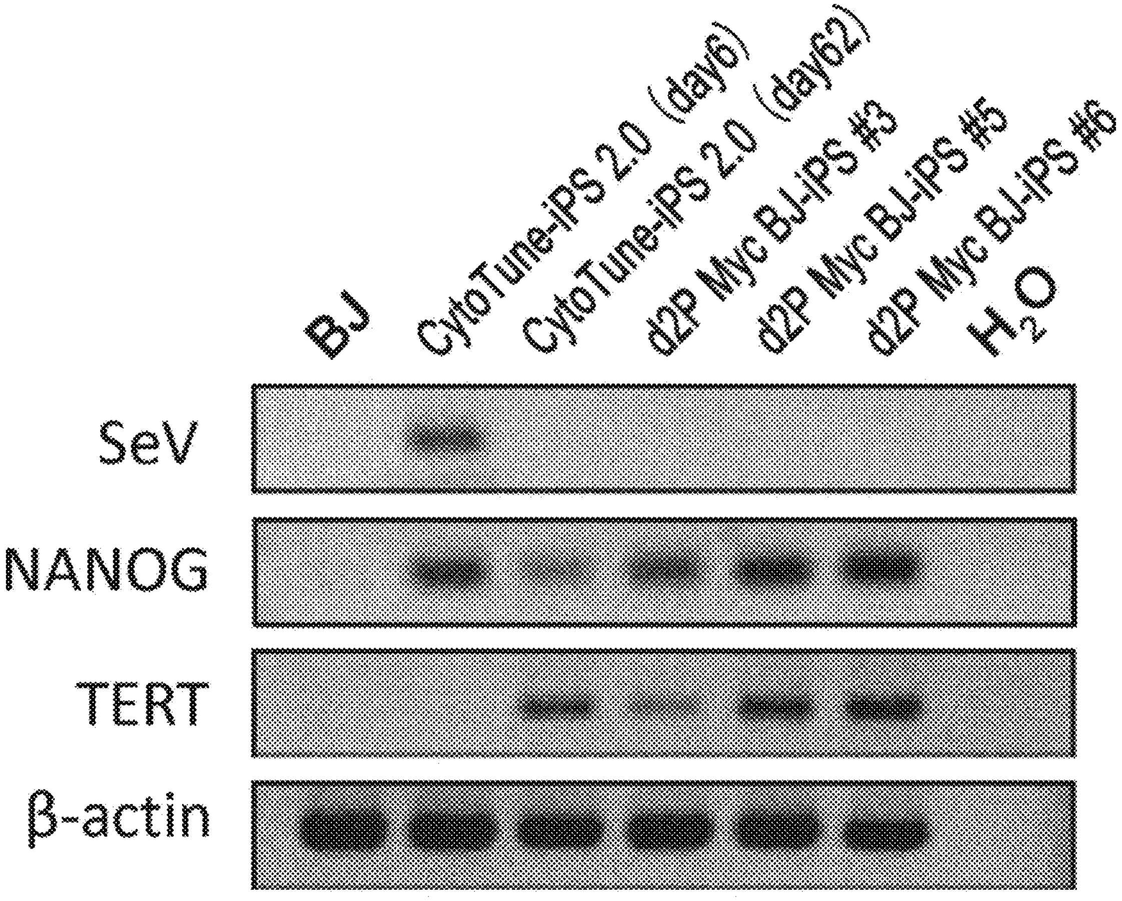

[Fig.29]
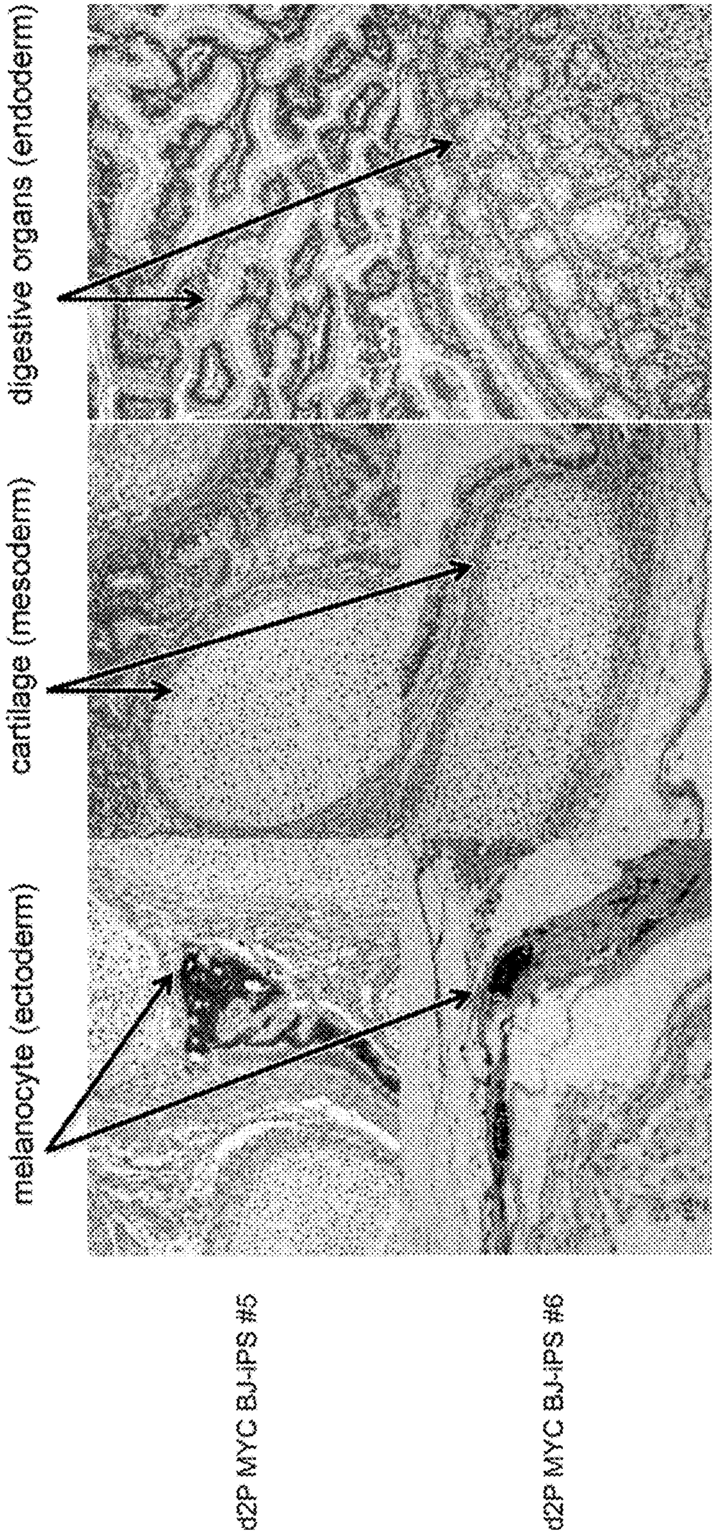

[Fig.30]
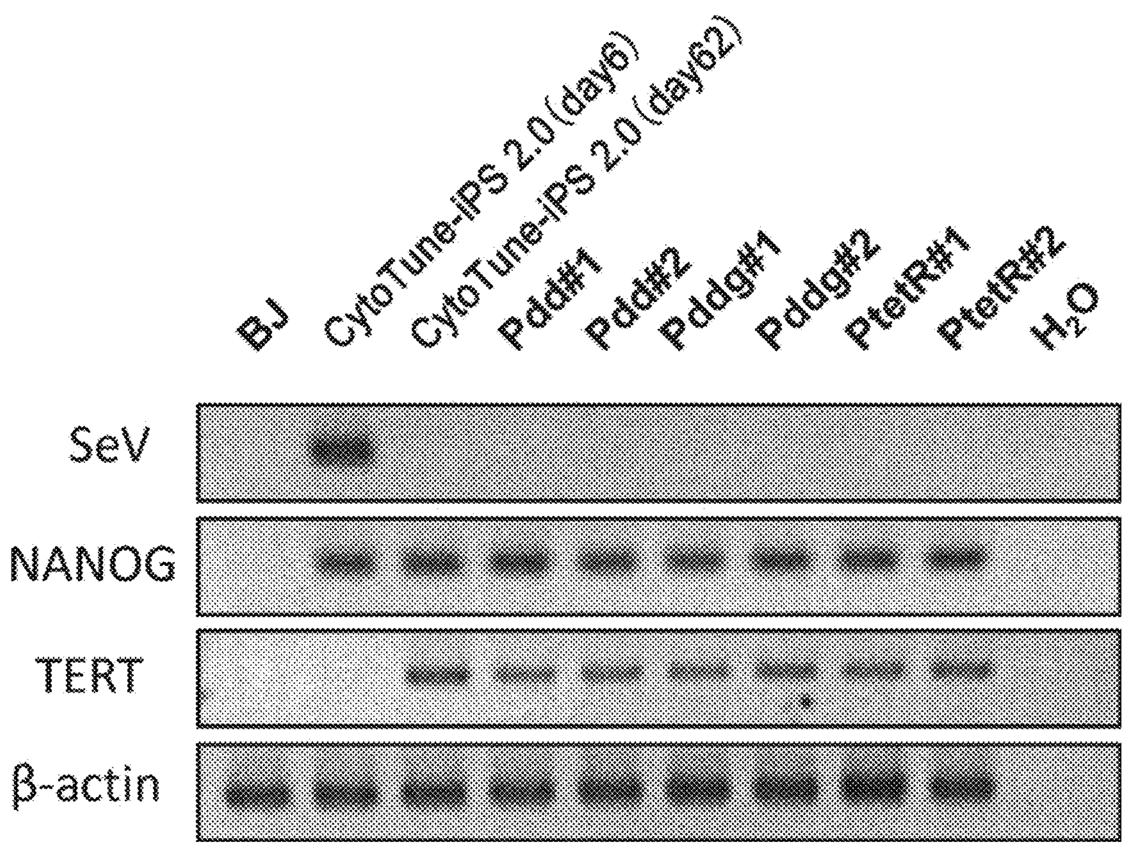
[Fig.31]
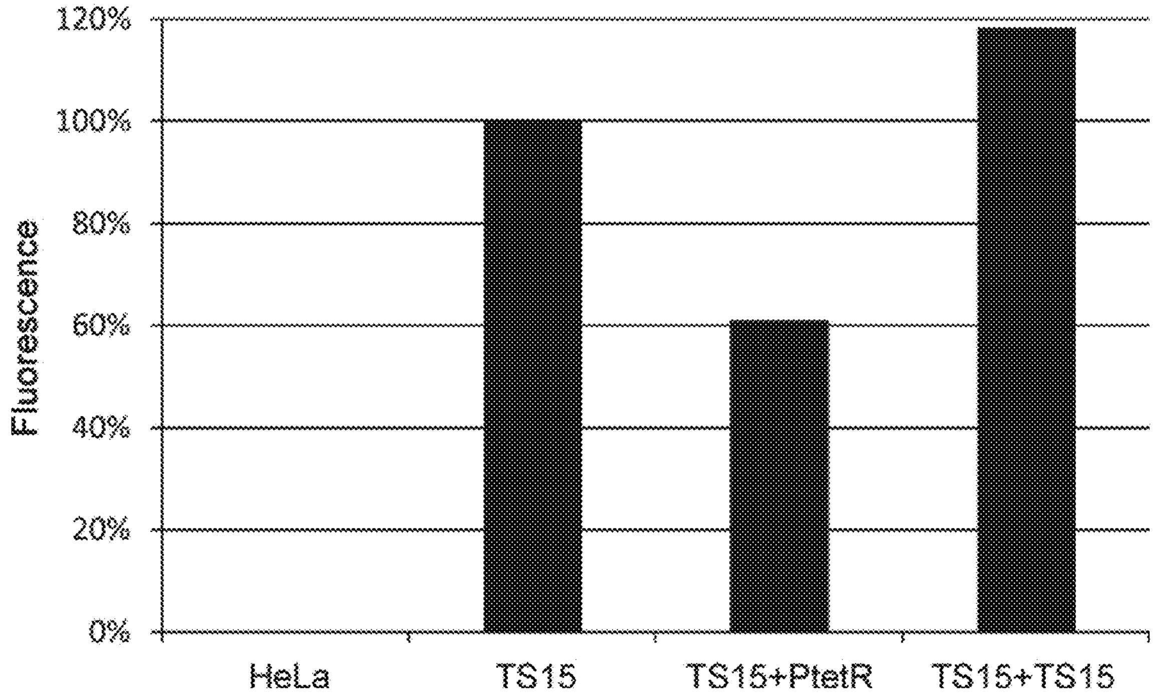

[Fig.32]
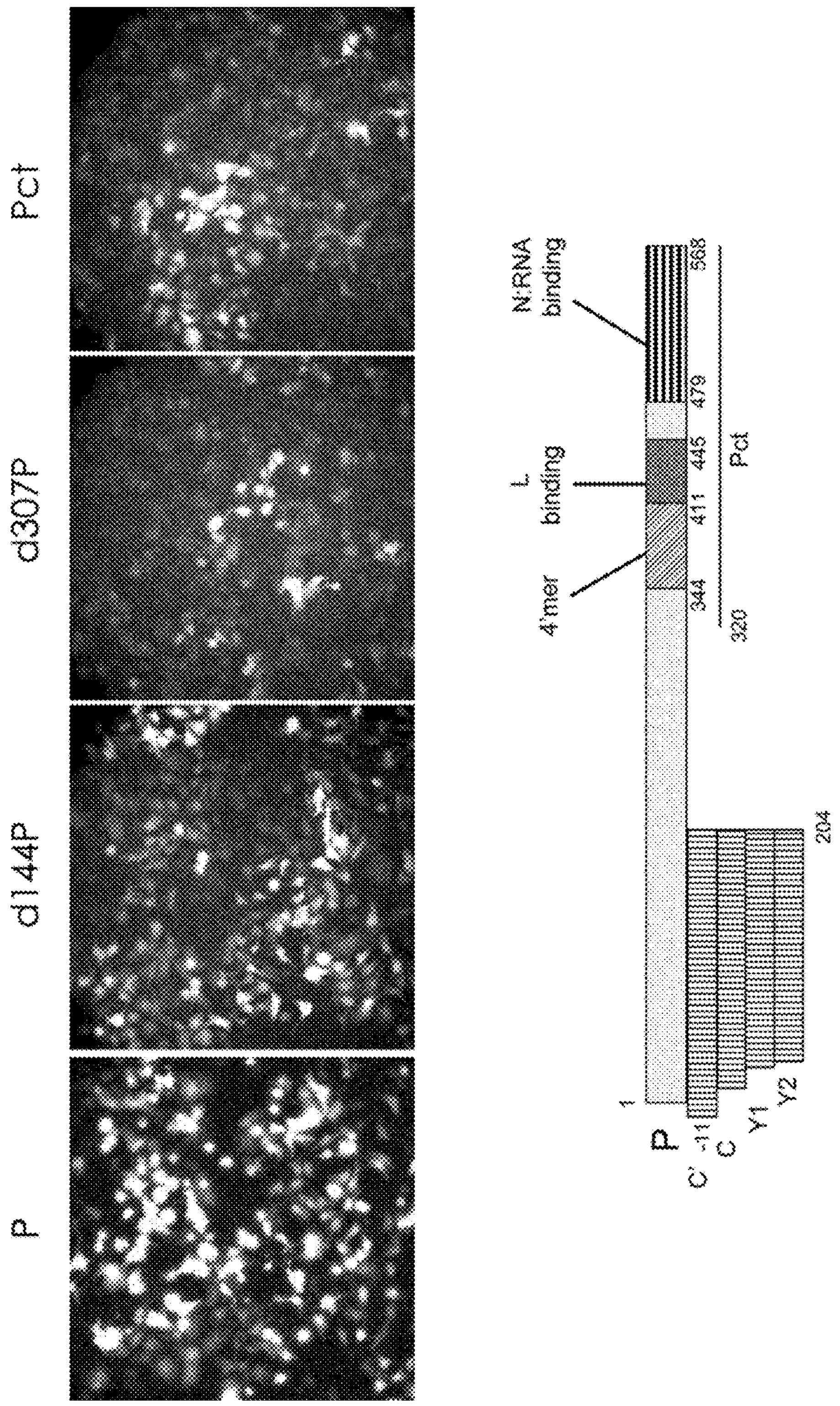

[Fig.33]
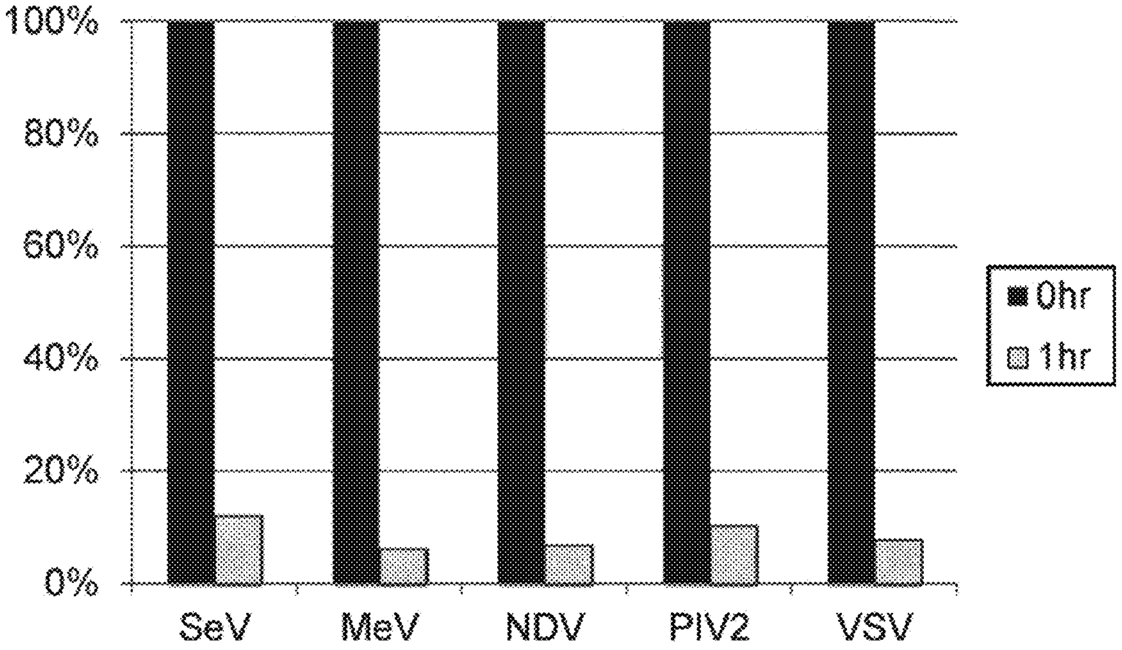
[Fig.34a]
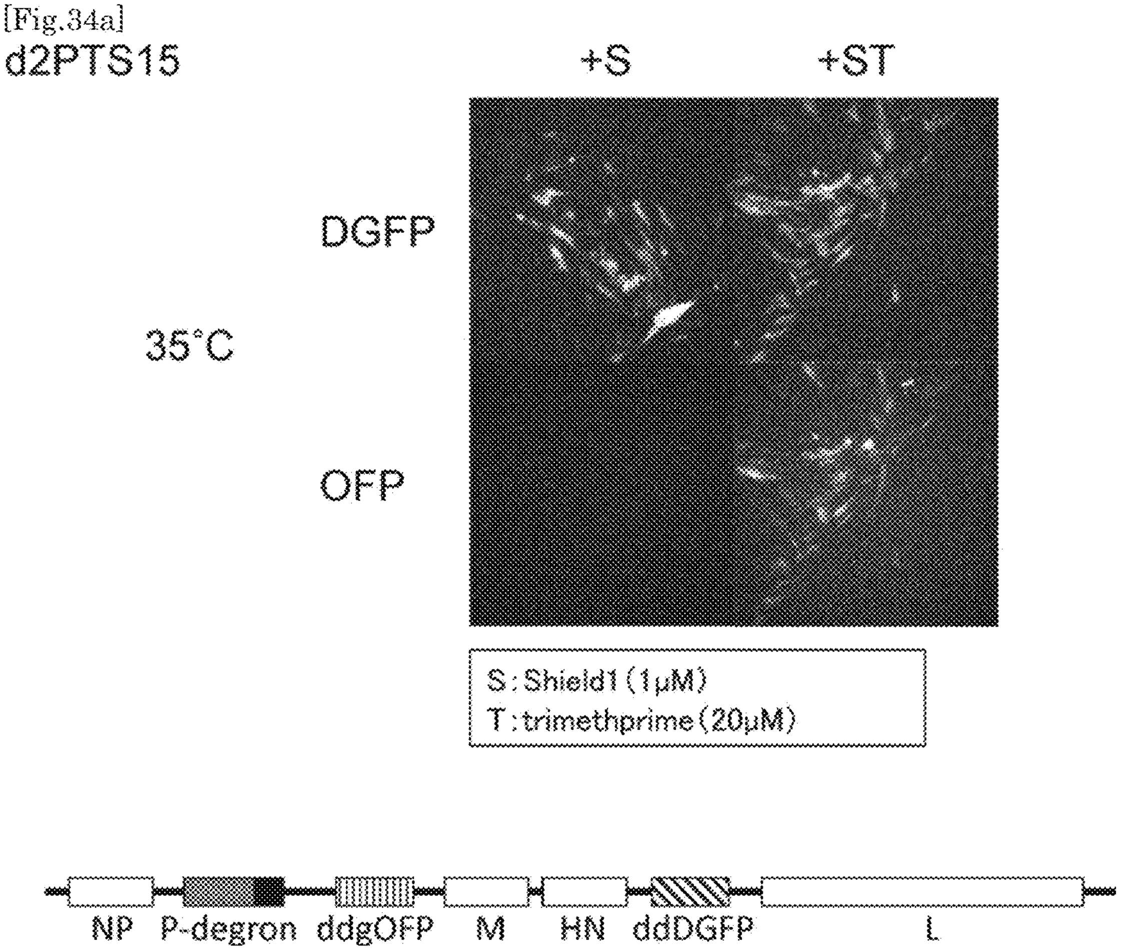

[Fig.34b]
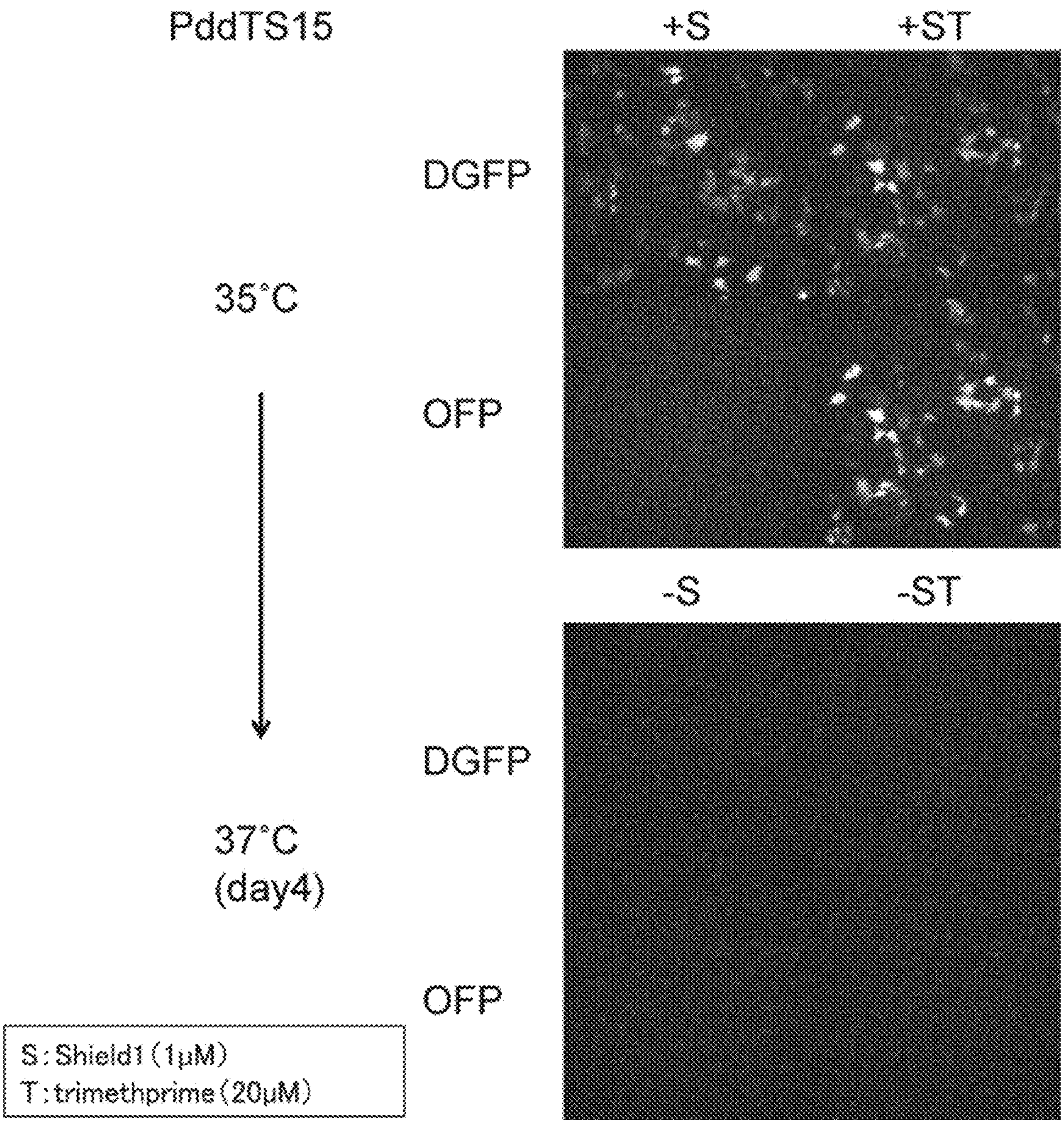
[Fig.35]
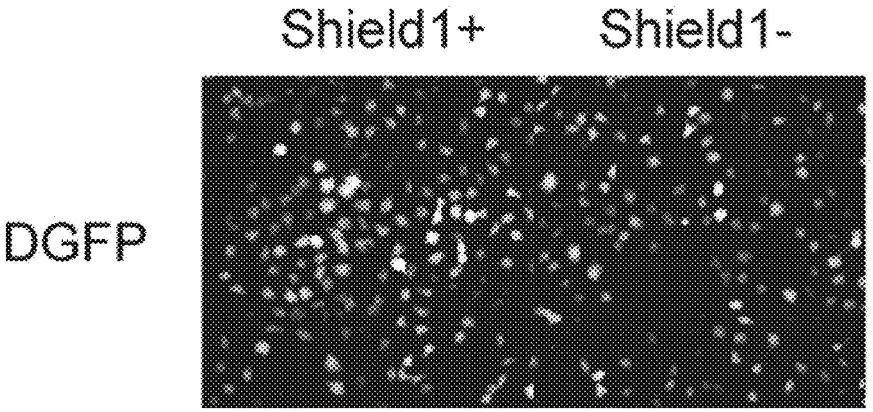

SEQUENCE LISTING

```
<160> NUMBER OF SEQ ID NOS: 121

<210> SEQ ID NO 1
<211> LENGTH: 10
<212> TYPE: RNA
<213> ORGANISM: Artificial sequence
<220> FEATURE:
<223> OTHER INFORMATION: synthesized: sendai virus start signal

<400> SEQUENCE: 1

cwuuvwcccu                                                          10


<210> SEQ ID NO 2
<211> LENGTH: 10
<212> TYPE: RNA
<213> ORGANISM: Artificial sequence
<220> FEATURE:
<223> OTHER INFORMATION: synthesized: sendai virus start signal

<400> SEQUENCE: 2

cuuugacccu                                                          10


<210> SEQ ID NO 3
<211> LENGTH: 10
<212> TYPE: RNA
<213> ORGANISM: Artificial sequence
```

<220> FEATURE:
<223> OTHER INFORMATION: synthesized: sendai virus start signal

<400> SEQUENCE: 3
cauucacccu 10

<210> SEQ ID NO 4
<211> LENGTH: 10
<212> TYPE: RNA
<213> ORGANISM: Artificial sequence
<220> FEATURE:
<223> OTHER INFORMATION: synthesized: sendai virus start signal

<400> SEQUENCE: 4
cuuucacccu 10

<210> SEQ ID NO 5
<211> LENGTH: 10
<212> TYPE: DNA
<213> ORGANISM: Artificial sequence
<220> FEATURE:
<223> OTHER INFORMATION: synthesized: sendai virus start signal

<400> SEQUENCE: 5
agggtcaaag 10

<210> SEQ ID NO 6
<211> LENGTH: 10
<212> TYPE: DNA
<213> ORGANISM: Artificial sequence
<220> FEATURE:
<223> OTHER INFORMATION: synthesized: sendai virus start signal

<400> SEQUENCE: 6
agggtgaatg 10

<210> SEQ ID NO 7
<211> LENGTH: 10
<212> TYPE: DNA
<213> ORGANISM: Artificial sequence
<220> FEATURE:
<223> OTHER INFORMATION: synthesized: sendai virus start signal

<400> SEQUENCE: 7
agggtgaaag 10

<210> SEQ ID NO 8
<211> LENGTH: 28
<212> TYPE: DNA
<213> ORGANISM: Artificial sequence
<220> FEATURE:
<223> OTHER INFORMATION: synthesized: XhoI-AG-F

<400> SEQUENCE: 8
atatctcgag ctatggtgag cgtgatca 28

<210> SEQ ID NO 9
<211> LENGTH: 26
<212> TYPE: DNA
<213> ORGANISM: Artificial sequence
<220> FEATURE:
<223> OTHER INFORMATION: synthesized: EcoRI-AG-R

<400> SEQUENCE: 9
atatgaattc gcggccgcga tgaact 26

<210> SEQ ID NO 10
<211> LENGTH: 32
<212> TYPE: DNA
<213> ORGANISM: Artificial sequence
<220> FEATURE:
<223> OTHER INFORMATION: synthesized: NotI-ddAG-F

<400> SEQUENCE: 10
atatgcggcc gcaccatggg agtgcaggtg ga 32

<210> SEQ ID NO 11
<211> LENGTH: 26
<212> TYPE: DNA
<213> ORGANISM: Artificial sequence
<220> FEATURE:
<223> OTHER INFORMATION: synthesized: BamHI-P-F

<400> SEQUENCE: 11
atatggatcc agttcacgcg gccgca 26

<210> SEQ ID NO 12
<211> LENGTH: 26
<212> TYPE: DNA
<213> ORGANISM: Artificial sequence
<220> FEATURE:
<223> OTHER INFORMATION: synthesized: XhoI-P-R

<400> SEQUENCE: 12
atatctcgag tcggtgcagg ccttta 26

<210> SEQ ID NO 13
<211> LENGTH: 27
<212> TYPE: DNA
<213> ORGANISM: Artificial sequence
<220> FEATURE:
<223> OTHER INFORMATION: synthesized: Pmut-F1

<400> SEQUENCE: 13
ggatcatacg gcgcgccaag gtacttg 27

<210> SEQ ID NO 14
<211> LENGTH: 27
<212> TYPE: DNA
<213> ORGANISM: Artificial sequence
<220> FEATURE:
<223> OTHER INFORMATION: synthesized: Pmut-R1

<400> SEQUENCE: 14
caagtacctt ggcgcgccgt atgatcc 27

<210> SEQ ID NO 15
<211> LENGTH: 28
<212> TYPE: DNA
<213> ORGANISM: Artificial sequence
<220> FEATURE:
<223> OTHER INFORMATION: synthesized: Pmut-F2

<400> SEQUENCE: 15
caactagatc ctgcaggagg catcctac 28

<210> SEQ ID NO 16
<211> LENGTH: 28
<212> TYPE: DNA
<213> ORGANISM: Artificial sequence
<220> FEATURE:
<223> OTHER INFORMATION: synthesized: Pmut-R2

<400> SEQUENCE: 16
gtaggatgcc tcctgcagga tctagttg 28

<210> SEQ ID NO 17
<211> LENGTH: 30
<212> TYPE: DNA
<213> ORGANISM: Artificial sequence
<220> FEATURE:
<223> OTHER INFORMATION: synthesized: BamHI-L-F

<400> SEQUENCE: 17
atatggatcc gtacgatcgc agtccaccat 30

<210> SEQ ID NO 18
<211> LENGTH: 26
<212> TYPE: DNA
<213> ORGANISM: Artificial sequence
<220> FEATURE:
<223> OTHER INFORMATION: synthesized: XhoI-L-R

<400> SEQUENCE: 18
atatctcgag cagctagctc aactga 26

<210> SEQ ID NO 19
<211> LENGTH: 25
<212> TYPE: DNA
<213> ORGANISM: Artificial sequence
<220> FEATURE:
<223> OTHER INFORMATION: synthesized: Lmut-F

<400> SEQUENCE: 19
gtgaatggga ggccggccat aggtc 25

<210> SEQ ID NO 20
<211> LENGTH: 25
<212> TYPE: DNA
<213> ORGANISM: Artificial sequence
<220> FEATURE:
<223> OTHER INFORMATION: synthesized: Lmut-R

<400> SEQUENCE: 20
gacctatggc cggcctccca ttcac 25

<210> SEQ ID NO 21
<211> LENGTH: 22
<212> TYPE: DNA
<213> ORGANISM: Artificial sequence
<220> FEATURE:
<223> OTHER INFORMATION: synthesized: XhoI-L-F

<400> SEQUENCE: 21
atatctcgag tcactaaaga gt 22

<210> SEQ ID NO 22
<211> LENGTH: 27
<212> TYPE: DNA
<213> ORGANISM: Artificial sequence
<220> FEATURE:
<223> OTHER INFORMATION: synthesized: HindIII-L-R

<400> SEQUENCE: 22
atataagctt cgagctgtca tatggct 27

<210> SEQ ID NO 23

<211> LENGTH: 35
<212> TYPE: DNA
<213> ORGANISM: Artificial sequence
<220> FEATURE:
<223> OTHER INFORMATION: synthesized: HindIII-dd-F

<400> SEQUENCE: 23
atataagctt caccggtcgg gagtgcaggt ggaaa 35

<210> SEQ ID NO 24
<211> LENGTH: 39
<212> TYPE: DNA
<213> ORGANISM: Artificial sequence
<220> FEATURE:
<223> OTHER INFORMATION: synthesized: KpnI-dd-R

<400> SEQUENCE: 24
atatggtacc ctattccagt tctagaagct ccacatcga 39

<210> SEQ ID NO 25
<211> LENGTH: 27
<212> TYPE: DNA
<213> ORGANISM: Artificial sequence
<220> FEATURE:
<223> OTHER INFORMATION: synthesized: KpnI-Ldd-R

<400> SEQUENCE: 25
atatggtacc gcctattcca gttctag 27

<210> SEQ ID NO 26
<211> LENGTH: 27
<212> TYPE: DNA
<213> ORGANISM: Artificial sequence
<220> FEATURE:
<223> OTHER INFORMATION: synthesized: AscI-Pdd-F

<400> SEQUENCE: 26
atatggcgcg ccaaggtact tgatccg 27

<210> SEQ ID NO 27
<211> LENGTH: 25
<212> TYPE: DNA
<213> ORGANISM: Artificial sequence
<220> FEATURE:
<223> OTHER INFORMATION: synthesized: HindIII-Pdd-R

<400> SEQUENCE: 27
atataagctt gttggtcagt gactc 25

<210> SEQ ID NO 28
<211> LENGTH: 29
<212> TYPE: DNA
<213> ORGANISM: Artificial sequence
<220> FEATURE:
<223> OTHER INFORMATION: synthesized: SbfI-dd-R

<400> SEQUENCE: 28
atatcctgca ggatctattc cagttctag 29

<210> SEQ ID NO 29
<211> LENGTH: 54
<212> TYPE: DNA
<213> ORGANISM: Artificial sequence
<220> FEATURE:
<223> OTHER INFORMATION: synthesized: NotI-GFP-F

<400> SEQUENCE: 29
attgcggccg ccaaggttca cttatggtga gcaagggcga ggagctgttc accg 54

<210> SEQ ID NO 30
<211> LENGTH: 41
<212> TYPE: DNA
<213> ORGANISM: Artificial sequence
<220> FEATURE:
<223> OTHER INFORMATION: synthesized: NotI-GFP-R1

<400> SEQUENCE: 30
ccggcgggaa gccatggcta agcttcttgt acagctcgtc c 41

<210> SEQ ID NO 31
<211> LENGTH: 70
<212> TYPE: DNA
<213> ORGANISM: Artificial sequence
<220> FEATURE:
<223> OTHER INFORMATION: synthesized: NotI-GFP-R2

<400> SEQUENCE: 31
ggcgctctcc tgggcacaag acatgggcag cgtgccatca tcctgggcgg ccacggccgg 60
cgggaagcca 70

<210> SEQ ID NO 32
<211> LENGTH: 70
<212> TYPE: DNA
<213> ORGANISM: Artificial sequence
<220> FEATURE:
<223> OTHER INFORMATION: synthesized: NotI-GFP-R3

<400> SEQUENCE: 32
ctacacattg atcctagcag aagcacaggc tgcagggtgg cggtccatgg cgctctcctg 60
ggcacaagac 70

<210> SEQ ID NO 33
<211> LENGTH: 70
<212> TYPE: DNA
<213> ORGANISM: Artificial sequence
<220> FEATURE:
<223> OTHER INFORMATION: synthesized: NotI-GFP-R4

<400> SEQUENCE: 33
atatgcggcc gcgatgaact ttcaccctaa gtttttctta ctacggctac acattgatcc 60
tagcagaagc 70

<210> SEQ ID NO 34
<211> LENGTH: 70
<212> TYPE: DNA
<213> ORGANISM: Artificial sequence
<220> FEATURE:
<223> OTHER INFORMATION: synthesized: NotI-GFP-R5

<400> SEQUENCE: 34
ggcgctctcc tgggcacaag acatgggcag cgtgccatca tcctgctcct ccacctccgg 60
cgggaagcca 70

<210> SEQ ID NO 35
<211> LENGTH: 70
<212> TYPE: DNA
<213> ORGANISM: Artificial sequence
<220> FEATURE:
<223> OTHER INFORMATION: synthesized: NotI-GFP-R6

<400> SEQUENCE: 35
ggcgctctcc tgggcacaag acatgggcag ggcgccatca tcctgctcct ccacctccgg 60
cgggaagcca 70

<210> SEQ ID NO 36
<211> LENGTH: 22
<212> TYPE: DNA
<213> ORGANISM: Artificial sequence
<220> FEATURE:
<223> OTHER INFORMATION: synthesized: AG-F1

<400> SEQUENCE: 36
acaagagaaa aaacatgtat gg 22

<210> SEQ ID NO 37
<211> LENGTH: 30
<212> TYPE: DNA
<213> ORGANISM: Artificial sequence
<220> FEATURE:
<223> OTHER INFORMATION: synthesized: AG-R1

<400> SEQUENCE: 37
ccatggctaa gcttcttggc ctggctgggc 30

<210> SEQ ID NO 38
<211> LENGTH: 30
<212> TYPE: DNA
<213> ORGANISM: Artificial sequence
<220> FEATURE:
<223> OTHER INFORMATION: synthesized: AG-F2

<400> SEQUENCE: 38
gcccagccag gccaagaagc ttagccatgg 30

<210> SEQ ID NO 39
<211> LENGTH: 23
<212> TYPE: DNA
<213> ORGANISM: Artificial sequence
<220> FEATURE:
<223> OTHER INFORMATION: synthesized: AG-R2

<400> SEQUENCE: 39
gataacagca cctcctcccg act 23

<210> SEQ ID NO 40
<211> LENGTH: 18
<212> TYPE: DNA
<213> ORGANISM: Artificial sequence
<220> FEATURE:
<223> OTHER INFORMATION: synthesized: ddAG-F1

<400> SEQUENCE: 40
atcagagacc tgcgacaa 18

<210> SEQ ID NO 41
<211> LENGTH: 28
<212> TYPE: DNA
<213> ORGANISM: Artificial sequence
<220> FEATURE:
<223> OTHER INFORMATION: synthesized: ddAG-R

<400> SEQUENCE: 41
ctggatagag tatgtcagaa gggttttg 28

<210> SEQ ID NO 42
<211> LENGTH: 497
<212> TYPE: DNA
<213> ORGANISM: Artificial sequence
<220> FEATURE:
<223> OTHER INFORMATION: synthesized: ecDHFR

<400> SEQUENCE: 42
gcggccgcgc caccatgatc agtctgattg cggcgttagc ggtagatctc gttatcggca 60
tggaaaacgc catgccgtgg aacctgcctg ccgatctcgc ctggtttaaa cgcaacacct 120
taaataaacc cgtgattatg ggccgccata cctgggaatc aatcggtcgt ccgttgccag 180
gacgcaagaa tattatcctc agcagtcaac cgagtacgga cgatcgcgta acgtgggtga 240
agtcggtgga tgaagccatc gcggcgtgtg gtgacgtacc agaaatcatg gtgattggcg 300
gcggtcgcgt tattgaacag ttcttgccaa aagcgcagaa actgtatctg acgcatatcg 360
acgcagaagt ggaaggcgac actcatttcc cggattacga gccggatgac tgggaatcgg 420
tattcagcga gttccacgat gctgatgcgc agaactctca cagctattgc tttgagattc 480
tggagcggcg actcgag 497

<210> SEQ ID NO 43
<211> LENGTH: 20
<212> TYPE: DNA
<213> ORGANISM: Artificial sequence
<220> FEATURE:
<223> OTHER INFORMATION: synthesized: ddg-F

<400> SEQUENCE: 43
attaaccctc actaaaggga 20

<210> SEQ ID NO 44
<211> LENGTH: 28
<212> TYPE: DNA
<213> ORGANISM: Artificial sequence
<220> FEATURE:
<223> OTHER INFORMATION: synthesized: ddg-R

<400> SEQUENCE: 44
ccttagacac tcgccgctcc agaatctc 28

<210> SEQ ID NO 45
<211> LENGTH: 30
<212> TYPE: DNA
<213> ORGANISM: Artificial sequence
<220> FEATURE:
<223> OTHER INFORMATION: synthesized: RFP-F

<400> SEQUENCE: 45
gagcggcgag tgtctaaggg cgaagagctg 30

<210> SEQ ID NO 46
<211> LENGTH: 28
<212> TYPE: DNA
<213> ORGANISM: Artificial sequence
<220> FEATURE:
<223> OTHER INFORMATION: synthesized: RFP-R

<400> SEQUENCE: 46
ggctaagctt attaagtttg tgccccag 28

<210> SEQ ID NO 47
<211> LENGTH: 30
<212> TYPE: DNA

<213> ORGANISM: Artificial sequence
<220> FEATURE:
<223> OTHER INFORMATION: synthesized: d2-F

<400> SEQUENCE: 47
caaacttaat aagcttagcc atggcttccc 30

<210> SEQ ID NO 48
<211> LENGTH: 1778
<212> TYPE: DNA
<213> ORGANISM: Artificial sequence
<220> FEATURE:
<223> OTHER INFORMATION: synthesized: TIR1

<400> SEQUENCE: 48
gcggccgcgc caccatgacc tacttccccg aggaggtcgt ggagcacatc ttcagcttcc 60
tgcccgcaca gagagacagg aacaccgtct ccctggtgtg caaggtgtgg tacgagatcg 120
aaagactgtc caggaggggc gtgtttgtgg gcaactgtta tgccgtgagg gccggaaggg 180
tggccgcaag gttccccaac gtgagagccc tgaccgtgaa gggcaagccc cacttcgccg 240
acttcaacct ggtgcctccc gactggggcg gatatgccgg accctggatc gaggcagccg 300
ccagagggtg ccatggactg gaggaactga ggatgaagag aatggtggtc tccgacgagt 360
ccctggagct gctggcaagg agctttccta gattcagggc actggtgctg atctcctgcg 420
agggctttag caccgacggc ctggcagctg tggcctccca ctgcaaactg ctgagggagc 480
tggacctgca agagaacgag gtggaggaca gaggccctag gtggctgagc tgttttcctg 540
actcctgcac tagcctggtc agcctgaatt ttgcctgcat caagggagag gtgaacgccg 600
gcagcctgga gaggctggtg agcaggagcc ccaatctgag gtccctgagg ctgaatagga 660
gcgtgagcgt ggacaccctg gccaagatcc tgctgaggac acctaacctg gaagacctgg 720
gcaccggcaa cctgacagac gacttccaga ccgagagcta cttcaagctg acctccgccc 780
tggaaaagtg taagatgctg agatccctgt ccggcttctg ggacgccagc cccgtgtgtc 840
tgagcttcat ctacccccctg tgcgcccagc tgactgggct gaacctgagc tacgccccca 900
ccctggacgc cagcgatctg actaagatga tcagcaggtg cgtgaagctg caaaggctgt 960
gggtgctgga ttgcatcagc gacaagggac tgcaagtggt ggccagcagc tgtaaagatc 1020
tgcaggaact gagggtgttc cctagcgact tctacgtggc cggctacagc gccgtgaccg 1080
aggagggcct ggtcgccgtc agcctgggat gccccaagct gaacagcctg ctgtacttct 1140
gccaccaaat gaccaacgct gccctggtga ccgtggccaa gaactgccca aactttacca 1200
ggtttagact gtgtatcctg gagcccggca agcccgatgt cgtgaccagc caacccctgg 1260
acgagggctt cggcgcaatt gtgagggagt gcaaggggct gcagagactg agcatctccg 1320
ggctgctgac cgacaaagtg ttcatgtata ttggcaagta cgctaaacaa ctggaaatgc 1380
tgtccatcgc cttcgcaggc gacagcgata agggcatgat gcacgtcatg aacggctgca 1440
agaatctgag aaaactggag atcagggact ccccatttgg ggatgctgct ctgctgggca 1500
acttcgccag gtacgagacc atgaggagcc tgtggatgtc ctcctgtaac gtcacactga 1560
agggctgtca ggtcctggcc tccaaaatgc ccatgctgaa cgtggaggtg attaacgaga 1620
gggacggctc caacgagatg gaggagaacc atggcgacct gccaaaggtg gagaagctgt 1680
acgtgtatag gaccacagct ggggccagag atgacgcccc caatttcgtg aaaatcctgt 1740
agtaagtaag aaaaacttag ggtgaaagtt gcggccgc 1778

<210> SEQ ID NO 49
<211> LENGTH: 22
<212> TYPE: DNA
<213> ORGANISM: Artificial sequence
<220> FEATURE:
<223> OTHER INFORMATION: synthesized: AGaid-F

<400> SEQUENCE: 49
taactgacta gcaggcttgt cg 22

<210> SEQ ID NO 50
<211> LENGTH: 70
<212> TYPE: DNA
<213> ORGANISM: Artificial sequence
<220> FEATURE:
<223> OTHER INFORMATION: synthesized: AGaid-R1

<400> SEQUENCE: 50
cactggtggc catcccacaa cttgactacc tccacctccg cttccacctc caccactctt 60
ggcctgactc 70

<210> SEQ ID NO 51
<211> LENGTH: 62
<212> TYPE: DNA
<213> ORGANISM: Artificial sequence
<220> FEATURE:
<223> OTHER INFORMATION: synthesized: AGaid-R2

<400> SEQUENCE: 51
ctttcaccct aagtttttct tactacggct actttctata tgatctcact ggtggccatc 60
cc 62

<210> SEQ ID NO 52
<211> LENGTH: 35
<212> TYPE: DNA
<213> ORGANISM: Artificial sequence
<220> FEATURE:
<223> OTHER INFORMATION: synthesized: AGaid-R3

<400> SEQUENCE: 52
ctgcggccgc gatgaacttt caccctaagt ttttc 35

<210> SEQ ID NO 53
<211> LENGTH: 22
<212> TYPE: DNA
<213> ORGANISM: Artificial sequence
<220> FEATURE:
<223> OTHER INFORMATION: synthesized: Paid-F

<400> SEQUENCE: 53
ctgcaaccca tggagatgaa gg 22

<210> SEQ ID NO 54
<211> LENGTH: 70
<212> TYPE: DNA
<213> ORGANISM: Artificial sequence
<220> FEATURE:
<223> OTHER INFORMATION: synthesized: Paid-R1

<400> SEQUENCE: 54
ctggtggcca tcccacaact tgactacctc cacctccgct tccacctcca ccactgttgg 60
tcagtgactc 70

<210> SEQ ID NO 55

<211> LENGTH: 50
<212> TYPE: DNA
<213> ORGANISM: Artificial sequence
<220> FEATURE:
<223> OTHER INFORMATION: synthesized: Paid-R2

<400> SEQUENCE: 55
tatacctgca ggatctactt tctatatgat ctcactggtg gccatcccac 50

<210> SEQ ID NO 56
<211> LENGTH: 22
<212> TYPE: DNA
<213> ORGANISM: Artificial sequence
<220> FEATURE:
<223> OTHER INFORMATION: synthesized: Laid-F

<400> SEQUENCE: 56
atcactgcta gatctgtgct gc 22

<210> SEQ ID NO 57
<211> LENGTH: 69
<212> TYPE: DNA
<213> ORGANISM: Artificial sequence
<220> FEATURE:
<223> OTHER INFORMATION: synthesized: Laid-R1

<400> SEQUENCE: 57
ggtggccatc ccacaacttg actacctcca cctccgcttc cacctccacc actcgagctg 60
tcatatggc 69

<210> SEQ ID NO 58
<211> LENGTH: 54
<212> TYPE: DNA
<213> ORGANISM: Artificial sequence
<220> FEATURE:
<223> OTHER INFORMATION: synthesized: Laid-R2

<400> SEQUENCE: 58
ctaattacta ctttctatat gatctcactg gtggccatcc cacaacttga ctac 54

<210> SEQ ID NO 59
<211> LENGTH: 65
<212> TYPE: DNA
<213> ORGANISM: Artificial sequence
<220> FEATURE:
<223> OTHER INFORMATION: synthesized: Laid-R3

<400> SEQUENCE: 59
tataggtacc gcggagcttc gatcgttctg cacgataggg actaattact actttctata 60
tgatc 65

<210> SEQ ID NO 60
<211> LENGTH: 28
<212> TYPE: DNA
<213> ORGANISM: Artificial sequence
<220> FEATURE:
<223> OTHER INFORMATION: synthesized: ddPts15-F1

<400> SEQUENCE: 60
attctcgagg atcaagatgc cttcattc 28

<210> SEQ ID NO 61
<211> LENGTH: 27
<212> TYPE: DNA
<213> ORGANISM: Artificial sequence
<220> FEATURE:
<223> OTHER INFORMATION: synthesized: ddPts15-R2

<400> SEQUENCE: 61
aataagcttc tagttggtca gtgactc 27

<210> SEQ ID NO 62
<211> LENGTH: 29
<212> TYPE: DNA
<213> ORGANISM: Artificial sequence
<220> FEATURE:
<223> OTHER INFORMATION: synthesized: ddPts15-F2

<400> SEQUENCE: 62
attggcgcgc caaggtactt gatccgtag 29

<210> SEQ ID NO 63
<211> LENGTH: 29
<212> TYPE: DNA
<213> ORGANISM: Artificial sequence
<220> FEATURE:
<223> OTHER INFORMATION: synthesized: ddPts15-R2

<400> SEQUENCE: 63
cacctgcact cccatgcggt aagtgtagc 29

<210> SEQ ID NO 64
<211> LENGTH: 29
<212> TYPE: DNA
<213> ORGANISM: Artificial sequence
<220> FEATURE:
<223> OTHER INFORMATION: synthesized: ddPts15-F3

<400> SEQUENCE: 64
gctacactta ccgcatggga gtgcaggtg 29

<210> SEQ ID NO 65
<211> LENGTH: 36
<212> TYPE: DNA
<213> ORGANISM: Artificial sequence
<220> FEATURE:
<223> OTHER INFORMATION: synthesized: ddPts15-R3

<400> SEQUENCE: 65
aatcctgcag gtgatgatct agttggtcag tgactc 36

<210> SEQ ID NO 66
<211> LENGTH: 30
<212> TYPE: DNA
<213> ORGANISM: Artificial sequence
<220> FEATURE:
<223> OTHER INFORMATION: synthesized: HSVp-F

<400> SEQUENCE: 66
atatagatct aaatgagtct tcggacctcg 30

<210> SEQ ID NO 67
<211> LENGTH: 28
<212> TYPE: DNA
<213> ORGANISM: Artificial sequence
<220> FEATURE:
<223> OTHER INFORMATION: synthesized: HSVp-R

<400> SEQUENCE: 67
atatgctagc ttaagcgggt cgctgcag 28

<210> SEQ ID NO 68
<211> LENGTH: 46
<212> TYPE: DNA
<213> ORGANISM: Artificial sequence
<220> FEATURE:
<223> OTHER INFORMATION: synthesized: HaloTag-F1

<400> SEQUENCE: 68
tctgtacttt cagagcgata acgatggatc cgaaatcggt actggc 46

<210> SEQ ID NO 69
<211> LENGTH: 30
<212> TYPE: DNA
<213> ORGANISM: Artificial sequence
<220> FEATURE:
<223> OTHER INFORMATION: synthesized: HaloTag-R

<400> SEQUENCE: 69
gcggccgctt aaccggaaat ctcgagcgtc 30

<210> SEQ ID NO 70
<211> LENGTH: 47
<212> TYPE: DNA
<213> ORGANISM: Artificial sequence
<220> FEATURE:
<223> OTHER INFORMATION: synthesized: HaloTag-F2

<400> SEQUENCE: 70
gctagcatat ggtaccccaa ccactgagga tctgtacttt cagagcg 47

<210> SEQ ID NO 71
<211> LENGTH: 30
<212> TYPE: DNA
<213> ORGANISM: Artificial sequence
<220> FEATURE:
<223> OTHER INFORMATION: synthesized: ddP-Halo-F

<400> SEQUENCE: 71
atatgctagc atgggagtgc aggtggaaac 30

<210> SEQ ID NO 72
<211> LENGTH: 28
<212> TYPE: DNA
<213> ORGANISM: Artificial sequence
<220> FEATURE:
<223> OTHER INFORMATION: synthesized: ddP-Halo-R

<400> SEQUENCE: 72
atatggtacc ctagttggtc agtgactc 28

<210> SEQ ID NO 73
<211> LENGTH: 28
<212> TYPE: DNA
<213> ORGANISM: Artificial sequence
<220> FEATURE:
<223> OTHER INFORMATION: synthesized: Pdd-Halo-F

<400> SEQUENCE: 73
atatgctagc atggatcaag atgccttc 28

<210> SEQ ID NO 74
<211> LENGTH: 28
<212> TYPE: DNA
<213> ORGANISM: Artificial sequence
<220> FEATURE:
<223> OTHER INFORMATION: synthesized: dAG-R2

<400> SEQUENCE: 74
caaaaccctt ctgacatact ctatccag 28

<210> SEQ ID NO 75
<211> LENGTH: 29
<212> TYPE: DNA
<213> ORGANISM: Artificial sequence
<220> FEATURE:
<223> OTHER INFORMATION: synthesized: dP-R1

<400> SEQUENCE: 75
ccatggctaa gcttgttggt cagtgactc 29

<210> SEQ ID NO 76
<211> LENGTH: 30
<212> TYPE: DNA
<213> ORGANISM: Artificial sequence
<220> FEATURE:
<223> OTHER INFORMATION: synthesized: dP-R2

<400> SEQUENCE: 76
ccggcgggaa gccatggcta agcttgttgg 30

<210> SEQ ID NO 77
<211> LENGTH: 37
<212> TYPE: DNA
<213> ORGANISM: Artificial sequence
<220> FEATURE:
<223> OTHER INFORMATION: synthesized: dP-R5

<400> SEQUENCE: 77
attcctgcag gatctacaca ttgatcctag cagaagc 37

<210> SEQ ID NO 78
<211> LENGTH: 34
<212> TYPE: DNA
<213> ORGANISM: Artificial sequence
<220> FEATURE:
<223> OTHER INFORMATION: synthesized: HindIII-ddg-F

<400> SEQUENCE: 78
aataagcttc accggtcgat cagtctgatt gcgg 34

<210> SEQ ID NO 79
<211> LENGTH: 37
<212> TYPE: DNA
<213> ORGANISM: Artificial sequence
<220> FEATURE:
<223> OTHER INFORMATION: synthesized: SbfI-ddg-R

<400> SEQUENCE: 79
cttcctgcag gattatctat cgccgctcca gaatctc 37

<210> SEQ ID NO 80
<211> LENGTH: 621
<212> TYPE: DNA
<213> ORGANISM: Artificial sequence
<220> FEATURE:
<223> OTHER INFORMATION: synthesized: TetR

<400> SEQUENCE: 80
atgtctaggc tggacaagag taaggtgatt aacagcgcac tggagctgct taatgaggtc 60
ggaatcgaag gtttgacaac ccagaaactc gcccagaagc tgggtgtgga gcagcctaca 120

```
ttgtattggc atgtgaagaa taagcgggct ttgctcgacg ccttggccat tgagatgttg    180

gataggcacc atactcactt ttgccctttg gaaggggaaa gctggcaaga cttcttgcgc    240

aataacgcta agagttttag atgtgctttg ctgagtcatc gcaatggagc aaaggtgcat    300

tctgacacac ggcctacaga gaagcagtat gaaactctgg agaatcaatt ggccttcttg    360

tgccaacaag gtttctcact ggagaatgca ttgtatgcac tcagcgctgt gggacatttt    420

actttgggtt gcgtgttgga agatcaagag catcaagtcg ctaaagaaga aagggaaaca    480

cctactactg atagtatgcc gcccttgttg cggcaagcta tcgaattgtt tgatcaccaa    540

ggtgcagagc cagccttctt gttcggcctt gaattgatca tctgcggatt ggagaaacaa    600

cttaaatgtg aaagtgggtc t                                              621
```

<210> SEQ ID NO 81
<211> LENGTH: 39
<212> TYPE: DNA
<213> ORGANISM: Artificial sequence
<220> FEATURE:
<223> OTHER INFORMATION: synthesized: NotI-TetR-F

<400> SEQUENCE: 81

```
atatgcggcc gccttgccac catgtctagg ctggacaag                            39
```

<210> SEQ ID NO 82
<211> LENGTH: 30
<212> TYPE: DNA
<213> ORGANISM: Artificial sequence
<220> FEATURE:
<223> OTHER INFORMATION: synthesized: TetR-R

<400> SEQUENCE: 82

```
cacgctcaca gacccacttt cacatttaag                                      30
```

<210> SEQ ID NO 83
<211> LENGTH: 29
<212> TYPE: DNA
<213> ORGANISM: Artificial sequence
<220> FEATURE:
<223> OTHER INFORMATION: synthesized: d2AG-F

<400> SEQUENCE: 83

```
gtgggtctgt gagcgtgatc aagcccgag                                       29
```

<210> SEQ ID NO 84
<211> LENGTH: 30
<212> TYPE: DNA
<213> ORGANISM: Artificial sequence
<220> FEATURE:
<223> OTHER INFORMATION: synthesized: dP-R7

<400> SEQUENCE: 84

```
cagcctagag ttggtcagtg actctatgtc                                      30
```

<210> SEQ ID NO 85
<211> LENGTH: 30
<212> TYPE: DNA
<213> ORGANISM: Artificial sequence
<220> FEATURE:
<223> OTHER INFORMATION: synthesized: PtetR-F

<400> SEQUENCE: 85

```
ctgaccaact ctaggctgga caagagtaag                                      30
```

<210> SEQ ID NO 86
<211> LENGTH: 38
<212> TYPE: DNA
<213> ORGANISM: Artificial sequence
<220> FEATURE:
<223> OTHER INFORMATION: synthesized: PtetR-R

<400> SEQUENCE: 86
atatcctgca ggatctaaga cccactttca catttaag 38

<210> SEQ ID NO 87
<211> LENGTH: 25
<212> TYPE: DNA
<213> ORGANISM: Artificial sequence
<220> FEATURE:
<223> OTHER INFORMATION: synthesized: SeV-L

<400> SEQUENCE: 87
ccgtagtaag aaaaacttag ggtga 25

<210> SEQ ID NO 88
<211> LENGTH: 21
<212> TYPE: DNA
<213> ORGANISM: Artificial sequence
<220> FEATURE:
<223> OTHER INFORMATION: synthesized: SeV-R

<400> SEQUENCE: 88
gatccatgcg gtaagtgtag c 21

<210> SEQ ID NO 89
<211> LENGTH: 40
<212> TYPE: PRT
<213> ORGANISM: Artificial sequence
<220> FEATURE:
<223> OTHER INFORMATION: synthesized: d2tag

<400> SEQUENCE: 89

```
Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40
```

<210> SEQ ID NO 90
<211> LENGTH: 40
<212> TYPE: PRT
<213> ORGANISM: Artificial sequence
<220> FEATURE:
<223> OTHER INFORMATION: synthesized: d4tag

<400> SEQUENCE: 90

```
Ser His Gly Phe Pro Pro Glu Val Glu Glu Gln Asp Asp Gly Ala Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40
```

<210> SEQ ID NO 91
<211> LENGTH: 40
<212> TYPE: PRT
<213> ORGANISM: Artificial sequence
<220> FEATURE:

<223> OTHER INFORMATION: synthesized: d1tag

<400> SEQUENCE: 91

Ser His Gly Phe Pro Pro Ala Val Ala Ala Gln Asp Asp Gly Thr Leu
1 5 10 15

Pro Met Ser Cys Ala Gln Glu Ser Gly Met Asp Arg His Pro Ala Ala
20 25 30

Cys Ala Ser Ala Arg Ile Asn Val
35 40

<210> SEQ ID NO 92
<211> LENGTH: 107
<212> TYPE: PRT
<213> ORGANISM: Artificial sequence
<220> FEATURE:
<223> OTHER INFORMATION: synthesized: DD-tag (ACCESSION: NP_000792)

<400> SEQUENCE: 92

Gly Val Gln Val Glu Thr Ile Ser Pro Gly Asp Gly Arg Thr Phe Pro
1 5 10 15

Lys Arg Gly Gln Thr Cys Val Val His Tyr Thr Gly Met Leu Glu Asp
20 25 30

Gly Lys Lys Phe Asp Ser Ser Arg Asp Arg Asn Lys Pro Phe Lys Phe
35 40 45

Met Leu Gly Lys Gln Glu Val Ile Arg Gly Trp Glu Glu Gly Val Ala
50 55 60

Gln Met Ser Val Gly Gln Arg Ala Lys Leu Thr Ile Ser Pro Asp Tyr
65 70 75 80

Ala Tyr Gly Ala Thr Gly His Pro Gly Ile Ile Pro Pro His Ala Thr
85 90 95

Leu Val Phe Asp Val Glu Leu Leu Lys Leu Glu
100 105

<210> SEQ ID NO 93
<211> LENGTH: 107
<212> TYPE: PRT
<213> ORGANISM: Artificial sequence
<220> FEATURE:
<223> OTHER INFORMATION: synthesized: DD-tag (F36V/L106P)

<400> SEQUENCE: 93

Gly Val Gln Val Glu Thr Ile Ser Pro Gly Asp Gly Arg Thr Phe Pro
1 5 10 15

Lys Arg Gly Gln Thr Cys Val Val His Tyr Thr Gly Met Leu Glu Asp
20 25 30

Gly Lys Lys Val Asp Ser Ser Arg Asp Arg Asn Lys Pro Phe Lys Phe
35 40 45

Met Leu Gly Lys Gln Glu Val Ile Arg Gly Trp Glu Glu Gly Val Ala
50 55 60

Gln Met Ser Val Gly Gln Arg Ala Lys Leu Thr Ile Ser Pro Asp Tyr
65 70 75 80

Ala Tyr Gly Ala Thr Gly His Pro Gly Ile Ile Pro Pro His Ala Thr
85 90 95

Leu Val Phe Asp Val Glu Leu Leu Lys Pro Glu
100 105

<210> SEQ ID NO 94
<211> LENGTH: 159
<212> TYPE: PRT

<213> ORGANISM: Artificial sequence
<220> FEATURE:
<223> OTHER INFORMATION: synthesized: DDG-tag (ACCESSION: B7MAH1)

<400> SEQUENCE: 94

```
Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

<210> SEQ ID NO 95
<211> LENGTH: 159
<212> TYPE: PRT
<213> ORGANISM: Artificial sequence
<220> FEATURE:
<223> OTHER INFORMATION: synthesized: DDG-tag (R12L/G67S/Y100I)

<400> SEQUENCE: 95

```
Met Ile Ser Leu Ile Ala Ala Leu Ala Val Asp Leu Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

<210> SEQ ID NO 96
<211> LENGTH: 207

<212> TYPE: PRT
<213> ORGANISM: Escherichia coli
<220> FEATURE:
<223> OTHER INFORMATION: TetR-tag (ACCESSION: NP_941292)

<400> SEQUENCE: 96

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

<210> SEQ ID NO 97
<211> LENGTH: 207
<212> TYPE: PRT
<213> ORGANISM: Artificial sequence
<220> FEATURE:
<223> OTHER INFORMATION: synthesized: TetR-tag (R28Q/D95N/L101S/G102D)

<400> SEQUENCE: 97

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Gln Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asn Gly
                85                  90                  95

Ala Lys Val His Ser Asp Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125
```

```
Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205


<210> SEQ ID NO 98
<211> LENGTH: 39
<212> TYPE: DNA
<213> ORGANISM: Artificial sequence
<220> FEATURE:
<223> OTHER INFORMATION: synthesized: AID variant

<400> SEQUENCE: 98

caagttgtgg gatggccacc ggtgagatca taccggaag                            39


<210> SEQ ID NO 99
<211> LENGTH: 13
<212> TYPE: PRT
<213> ORGANISM: Artificial sequence
<220> FEATURE:
<223> OTHER INFORMATION: synthesized: AID

<400> SEQUENCE: 99

Gln Val Val Gly Trp Pro Pro Val Arg Ser Tyr Arg Lys
1               5                   10


<210> SEQ ID NO 100
<211> LENGTH: 39
<212> TYPE: DNA
<213> ORGANISM: Artificial sequence
<220> FEATURE:
<223> OTHER INFORMATION: synthesized: AID

<400> SEQUENCE: 100

caagttgtgg gatggccacc agtgagatca tatagaaag                            39


<210> SEQ ID NO 101
<211> LENGTH: 120
<212> TYPE: DNA
<213> ORGANISM: Artificial sequence
<220> FEATURE:
<223> OTHER INFORMATION: synthesized: mODC422-461 DNA

<400> SEQUENCE: 101

agccatggct tcccgccgga ggtggaggag caggatgatg gcacgctgcc catgtcttgt     60

gcccaggaga gcgggatgga ccgtcaccct gcagcctgtg cttctgctag gatcaatgtg    120


<210> SEQ ID NO 102
<211> LENGTH: 321
<212> TYPE: DNA
<213> ORGANISM: Artificial sequence
<220> FEATURE:
<223> OTHER INFORMATION: synthesized: DD-tag DNA

<400> SEQUENCE: 102

ggagtgcagg tggaaaccat ctccccagga gacgggcgca ccttccccaa gcgcggccag     60
```

-continued acctgcgtgg tgcactacac cgggatgctt gaagatggaa agaaatttga ttcctcccgg 120
gacagaaaca agccctttaa gtttatgcta ggcaagcagg aggtgatccg aggctgggaa 180
gaaggggttg cccagatgag tgtgggtcag agagccaaac tgactatatc tccagattat 240
gcctatggtg ccactgggca cccaggcatc atcccaccac atgccactct cgtcttcgat 300
gtggagcttc taaaactgga a 321

<210> SEQ ID NO 103
<211> LENGTH: 30
<212> TYPE: DNA
<213> ORGANISM: Artificial sequence
<220> FEATURE:
<223> OTHER INFORMATION: synthesized: NotI-SeV-Pd144-F

<400> SEQUENCE: 103
atatgcggcc gcaccatggg atatccgaga 30

<210> SEQ ID NO 104
<211> LENGTH: 30
<212> TYPE: DNA
<213> ORGANISM: Artificial sequence
<220> FEATURE:
<223> OTHER INFORMATION: synthesized: SeV-P-NotI-R

<400> SEQUENCE: 104
atatgcggcc gcctagttgg tcagtgactc 30

<210> SEQ ID NO 105
<211> LENGTH: 30
<212> TYPE: DNA
<213> ORGANISM: Artificial sequence
<220> FEATURE:
<223> OTHER INFORMATION: synthesized: NotI-SeV-Pd307-F

<400> SEQUENCE: 105
atatgcggcc gcaccatggg tctagagacc 30

<210> SEQ ID NO 106
<211> LENGTH: 30
<212> TYPE: DNA
<213> ORGANISM: Artificial sequence
<220> FEATURE:
<223> OTHER INFORMATION: synthesized: NotI-SeV-Pct-F

<400> SEQUENCE: 106
atatgcggcc gcaccatggg agagaacaca 30

<210> SEQ ID NO 107
<211> LENGTH: 1533
<212> TYPE: DNA
<213> ORGANISM: Artificial sequence
<220> FEATURE:
<223> OTHER INFORMATION: synthesized: MeV (AIK-C)

<400> SEQUENCE: 107
gctagcatgg cagaagagca ggcacgccat gtcaagaacg gactggaatg catccgggct 60
ctcaaggccg agcccatcgg ctcactggcc atcgaggaag ctatggcagc atggtcagaa 120
atatcagaca acccaggaca ggagcgagcc acctgcaggg aagagaaggc aggcagttcg 180
ggtctcagca aaccatgcct ctcagcaatt ggatcaactg aaggcggtgc acctcgcatc 240
cgcggtcagg gacctggaga gagcgatgac gacgctgaaa ctttgggaat ccccccaaga 300
aatctccagg catcaagcac tgggttacag tgttattatg tttatgatca cagcggtgaa 360
gcggttaagg gaatccaaga tgctgactct atcatggttc aatcaggcct tgatggtgat 420
agcaccctat caggaggaga caatgaatct gaaaacagcg atgtggatat tggcgaacct 480
gataccgagg gatatgctat cactgaccgg ggatctgctc ccatctctat ggggttcagg 540
gcttctgatg ttgaaactgc agaaggaggg gagatccacg agctcctgag actccaatcc 600
agaggcaaca actttccgaa gctggggaaa actctcaatg ttcctccgcc cccggacccc 660
ggtagggcca gcacttccgg gacacccatt aagaagggca cagacgcgag attagcctca 720
tttggaacgg agatcgcgtc tttattgaca ggtggtgcaa cccaatgtgc tcgaaagtca 780
ccctcggaac catcagggcc aggtgcacct gcggggaatg tccccgagta tgtgagcaat 840
gccgcactga tacaggagtg gacacccgaa tctggtacta caatctcccc gagatcccag 900
aataatgaag aagggggaga ctattatgat gatgagctgt tctctgatgt ccaagatatt 960
aaaacagcct tggccaaaat acacgaggat aatcagaaga taatctccaa gctagaatca 1020
ctgctgttat tgaagggaga agttgagtca attaagaagc agatcaacag gcaaaatatc 1080
agcatatcca ccctggaagg acacctctca agcatcatga tcgccattcc tggacttggg 1140
aaggacccca acgaccccac tgcagatgtc gaaatcaatc ccgacttgaa acccatcata 1200
ggcagagatt caggccgagc actggccgaa gttctcaaga aacccgttgc cagccgacaa 1260
ctccaaggaa tgacaaatgg acggaccagt tccagaggac agctgctgaa ggaatttcag 1320
ccaaagccga tcgggaagaa gatgagctca gccgtcgggt ttgttcctga caccggccct 1380
gcatcacgca gtgtaatccg ctccattata aaatccagcc ggctagagga ggatcggaag 1440
cgttacctga tgactctcct tgatgatatc aaaggagcca atgatcttgc caagttccac 1500
cagatgctga tgaagataat aatgaagaag ctt 1533

<210> SEQ ID NO 108
<211> LENGTH: 1197
<212> TYPE: DNA
<213> ORGANISM: Artificial sequence
<220> FEATURE:
<223> OTHER INFORMATION: synthesized: NDV (LaSota)

<400> SEQUENCE: 108
gctagcatgg ccacctttac ggatgcagag atcgacgagc tatttgagac aagtggaact 60
gtcattgaca acataattac agcccagggt aaaccagcag agactgttgg aaggagtgca 120
atcccacaag gcaagaccaa ggtgctgagc gcagcatggg agaagcatgg gagcatccag 180
ccaccggcca gtcaagacaa ccccgatcga caggacagat ctgacaaaca accatccaca 240
cccgagcaaa cgaccccgca tgacagcccg ccggccacat ccgccgacca gcccccccacc 300 caggccacag acgaagccgt cgacacacag ctcaggaccg gagcaagcaa ctctctgctg 360
ttgatgcttg acaagctcag caataaatcg tccaatgcta agaagggccc atggtcgagc 420
ccccaagagg ggaatcacca acgtccgact caacagcagg ggagtcaacc cagtcgcgga 480
aacagtcagg aaagaccgca gaaccaagtc aaggccgccc ctggaaacca gggcacagac 540
gtgaacacag catatcatgg acaatgggag gagtcacaac tatcagctgg tgcaacccct 600
catgctctcc gatcaaggca gagccaagac aatacccttg tatctgcgga tcatgtccag 660
ccacctgtag actttgtgca agcgatgatg tctatgatgg aggcgatatc acagagagta 720
agtaaggttg actatcagct agatcttgtc ttgaaacaga catcctccat ccctatgatg 780
cggtccgaaa tccaacagct gaaaacatct gttgcagtca tggaagccaa cttgggaatg 840

```
atgaagattc tggaccccgg ttgtgccaac atttcatctc tgagtgatct acgggcagtt    900

gcccgatctc acccggtttt agtttcaggc cctggagacc cctctcccta tgtgacacaa    960

ggaggcgaaa tggcacttaa taaactttcg caaccagtgc cacatccatc tgaattgatt   1020

aaacccgcca ctgcatgcgg gcctgatata ggagtggaaa aggacactgt ccgtgcattg   1080

atcatgtcac gcccaatgca cccgagttct tcagccaagc tcctaagcaa gttagatgca   1140

gccgggtcga tcgaggaaat caggaaaatc aagcgccttg ctctaaatgg caagctt      1197
```

<210> SEQ ID NO 109
<211> LENGTH: 687
<212> TYPE: DNA
<213> ORGANISM: Artificial sequence
<220> FEATURE:
<223> OTHER INFORMATION: synthesized: PIV2

<400> SEQUENCE: 109

```
gctagcatgg ccgaggaacc aacatacacc actgagcaag ttgatgaatt aatccatgct     60

ggactgggaa cagtagattt cttcctatct agacccatag atgctcagtc ttctttaggc    120

aaaggcagca tcccaccagg tgtcacagct gttctaacta gtgcagcgga ggcaaaatcc    180

aaaccagttg ctgctggtcc agttaaaccc aggcggaaga aagtgatcag caatactact    240

ccatacacta ttgcagacaa tattccacct gagaagctac cgatcaacac tccaataccc    300

aatccattac ttccactggc acgccctcac ggaaagatga cagacattga cattgtcact    360

gggaacatta cagaaggatc gtacaaaggt gtggagcttg ctaaattagg gaagcagaca    420

ctactcacaa ggttcacctc gaatgagcca gtctcctcag ctggatcagc ccaagacccc    480

aactttaaga gggggggagc taatagagaa agagcaagag gcaaccatag gagagaatgg    540

agtattgcat gggtcggaga tcaggtcaaa gtcttcgagt ggtgtaatcc caggtgtgcc    600

ccagtcacgg cctcagctcg caagttcacc tgcacatgcg gatcatgccc cagcatctgc    660

ggagaatgtg aaggagatca taagctt                                         687
```

<210> SEQ ID NO 110
<211> LENGTH: 807
<212> TYPE: DNA
<213> ORGANISM: Artificial sequence
<220> FEATURE:
<223> OTHER INFORMATION: synthesized: VSV

<400> SEQUENCE: 110

```
gctagcatgg ataatctcac aaaagttcgt gagtatctca agtcctattc tcgtctggat     60

caggcggtag gagagataga tgagatcgaa gcacaacgag ctgaaaagtc caattatgag    120

ttgttccaag aggatggagt ggaagagcat actaagccct cttattttca ggcagcagat    180

gattctgaca cagaatctga accagaaatt gaagacaatc aaggcttgta tgcaccagat    240

ccagaagctg agcaagttga aggctttata caggggcctt tagatgacta tgcagatgag    300

gaagtggatg ttgtatttac ttcggactgg aaacagcctg agcttgaatc tgacgagcat    360

ggaaagacct tacggttgac atcgccagag ggtttaagtg gagagcagaa atcccagtgg    420

ctttcgacga ttaaagcagt cgtgcaaagt gccaaatact ggaatctggc agagtgcaca    480

tttgaagcat cgggagaagg ggtcattatg aaggagcgcc agataactcc ggatgtatat    540

aaggtcactc cagtgatgaa cacacatccg tcccaatcag aagcagtatc agatgtttgg    600

tctctctcaa agacatccat gactttccaa cccaagaaag caagtcttca gcctctcacc    660

atatccttgg atgaattgtt ctcatctaga ggagagttca tctctgtcgg aggtgacgga    720
```

```
cgaatgtctc ataaagaggc catcctgctc ggcctgagat acaagaagtt gtacaatcag    780

gcgagagtca aatattctct gaagctt                                        807


<210> SEQ ID NO 111
<211> LENGTH: 27
<212> TYPE: DNA
<213> ORGANISM: Artificial sequence
<220> FEATURE:
<223> OTHER INFORMATION: synthesized: NotI-TKp-F

<400> SEQUENCE: 111

atatgcggcc gcgcttaagc tagcatg                                         27


<210> SEQ ID NO 112
<211> LENGTH: 41
<212> TYPE: DNA
<213> ORGANISM: Artificial sequence
<220> FEATURE:
<223> OTHER INFORMATION: synthesized: NotI-OFP-F

<400> SEQUENCE: 112

atatgcggcc gctcgccacc atgtcactgt ctaaacaggt g                         41


<210> SEQ ID NO 113
<211> LENGTH: 70
<212> TYPE: DNA
<213> ORGANISM: Artificial sequence
<220> FEATURE:
<223> OTHER INFORMATION: synthesized: OFP-EIS-NotI-R

<400> SEQUENCE: 113

atatgcggcc gcgaactttc accctaagtt tttcttactt actaggtttc cttgacgtcc     60

acggtgaaat                                                            70


<210> SEQ ID NO 114
<211> LENGTH: 30
<212> TYPE: DNA
<213> ORGANISM: Artificial sequence
<220> FEATURE:
<223> OTHER INFORMATION: synthesized: NotI-DGFP-F

<400> SEQUENCE: 114

atagcggccg cgacatgact gccctgaccg                                      30


<210> SEQ ID NO 115
<211> LENGTH: 69
<212> TYPE: DNA
<213> ORGANISM: Artificial sequence
<220> FEATURE:
<223> OTHER INFORMATION: synthesized: DGFP-EIS-NotI-R

<400> SEQUENCE: 115

tatgcggccg cgatgaactt tcaccctaag tttttcttac tacggttact gataggtatc     60

gagatcgac                                                             69


<210> SEQ ID NO 116
<211> LENGTH: 29
<212> TYPE: DNA
<213> ORGANISM: Artificial sequence
<220> FEATURE:
<223> OTHER INFORMATION: synthesized: ddgOFP-R

<400> SEQUENCE: 116
```

ttagacagtg atcgccgctc cagaatctc 29

<210> SEQ ID NO 117
<211> LENGTH: 29
<212> TYPE: DNA
<213> ORGANISM: Artificial sequence
<220> FEATURE:
<223> OTHER INFORMATION: synthesized: ddgOFP-F

<400> SEQUENCE: 117
ggagcggcga tcactgtcta aacaggtgc 29

<210> SEQ ID NO 118
<211> LENGTH: 35
<212> TYPE: DNA
<213> ORGANISM: Artificial sequence
<220> FEATURE:
<223> OTHER INFORMATION: synthesized: EIS-NotI-2R

<400> SEQUENCE: 118
cctgcggccg catgaacttt caccctaagt ttttc 35

<210> SEQ ID NO 119
<211> LENGTH: 39
<212> TYPE: DNA
<213> ORGANISM: Artificial sequence
<220> FEATURE:
<223> OTHER INFORMATION: synthesized: NotI-dd-F

<400> SEQUENCE: 119
atatgcggcc gcgccaccat gggagtgcag gtggaaacc 39

<210> SEQ ID NO 120
<211> LENGTH: 29
<212> TYPE: DNA
<213> ORGANISM: Artificial sequence
<220> FEATURE:
<223> OTHER INFORMATION: synthesized: ddgOFP-R

<400> SEQUENCE: 120
cggtcagggc agtttccagt tctagaagc 29

<210> SEQ ID NO 121
<211> LENGTH: 30
<212> TYPE: DNA
<213> ORGANISM: Artificial sequence
<220> FEATURE:
<223> OTHER INFORMATION: synthesized: ddDGFP-F

<400> SEQUENCE: 121
tctagaactg gaaactgccc tgaccgaagg 30

SENDAI VIRAL VECTOR ENCODING A DEGRON-P FUSION PROTEIN

TECHNICAL FIELD

The present invention relates to an improved negative-strand RNA virus vector. More specifically, the present invention relates to a negative-strand RNA virus vector including the P protein added with a degron and a use thereof.

BACKGROUND ART

Negative-strand RNA virus vectors such as Sendai virus (SeV) vectors are cytoplasm-type RNA virus vectors (vectors whose all expression stages are carried out in the cytoplasm), and thus, even when such negative-strand RNA virus vectors are used in vivo, there is no concern in that carried genes are integrated into host chromosomes to generate genetic toxicity. Furthermore, the negative-strand RNA virus vectors have various excellent capabilities, for example, high gene transfer efficiency and high expression efficiency can be obtained in both in vitro and in vivo and long-term persistent expression in vitro can be achieved. For these reasons, SeV vectors are widely applied and used as gene transfer vectors in production of pluripotent stem cells, gene therapy/gene vaccination, application to antibody production and functional analysis, and the like (Patent Documents 1 and 2 and Non-patent Documents 1 and 2).

Hitherto, transient expression caused by deficiency of the P protein of SeV vectors (Patent Document 3 and Non-patent Document 3), non-replicating vectors (Patent Document 4), removal of SeV vectors by the insertion of temperature-sensitive mutation(s) to the P protein or the L protein and temperature shift (Patent Documents 1 and 2), and removal of SeV vectors by adding mir-302 target sequence or siRNA to the SeV genome encoding the L protein (Patent Document 5) have been reported. However, P protein-deficient vectors have problems of low expression of carried genes and short-term expression (high expression capability of SeV vectors is impaired), and conventional temperature-sensitive mutant vectors have a problem in that it takes time to remove the vectors (culturing for several days at 39° C.). Incidentally, mir-302 is not a versatile method since expression thereof varies depending on cell species, and siRNA is a method that is influenced by gene transfer efficiency and inhibitory efficiency.

Meanwhile, regarding a degron that is a protein destabilizing sequence, Patent Documents 6 to 13 are known, and there is an example in which a degron is added to the protein of the carried gene (gene of interest; GOI) of the SeV vector (Non-patent Document 4); however, there is no example in which a degron is added to the viral protein of the SeV vector, nor the object of which is to enhance removal of the vector.

PRIOR ART DOCUMENTS

Patent Documents

Patent Document 1: International Publication No. WO 2010/008054

Patent Document 2: International Publication No. WO 2012/029770

Patent Document 3: International Publication No. WO 2008/133206

Patent Document 4: International Publication No. WO 2008/007581

Patent Document 5: International Publication No. WO 2012/063817

Patent Document 6: US Patent Publication No. 2009/0215169

Patent Document 7: US Patent Publication No. 2012/0178168

Patent Document 8: International Publication No. WO 2007/032555

Patent Document 9: International Publication No. WO 99/54348

Patent Document 10: International Publication No. WO 2004/025264

Patent Document 11: Japanese Unexamined Patent Publication No. 2009-136154

Patent Document 12: Japanese Unexamined Patent Publication No. 2011-101639

Patent Document 13: International Publication No. WO 2010/125620

Non-Patent Documents

Non-patent Document 1: Bitzer M, et al., J Gene Med. (2003) 5, 543-553

Non-patent Document 2: Griesenbach U, et al., Curr Opin Mol Ther. (2005) 7, 346-352

Non-patent Document 3: Abe T, et al. Exp Hematol. (2011) 39, 47-54

Non-patent Document 4: Nishimura, K. et al. Stem Cell Reports. (2014) 3, 915-929

SUMMARY OF THE INVENTION

Problems to be Solved by the Invention

An objective of the present invention is to provide a negative-strand RNA virus vector in which a degron is added to the P protein of the negative-strand RNA virus, a method for producing the vector, and a use thereof. In addition, the present invention relates to a method for enhancing removal of a vector by using a negative-strand RNA virus vector in which a degron is added to the P protein of the negative-strand RNA virus.

Means for Solving the Problems

The present inventors have searched for a method of improving the removal speed of the vector while gene expression capacity of a negative-strand RNA virus vector is maintained.

The present inventors tried to use P gene-deficient vectors at first in order to carry out transient expression using negative-strand RNA virus vectors. However, when the produced vectors were introduced into cells and then expression of the reporter protein was examined, expression of the reporter protein could not be confirmed in HeLa cells that were not expressing the P protein. Also, in Non-patent Document 3, it is reported that expression of the carried genes from the P gene-deficient vectors is 1/10 or less as compared to vectors in which P gene is not deleted. Furthermore, the non-replicating SeV vector of Patent Document 4 needs to have a high titer or presence of a helper vector in order to obtain a sufficient gene expression amount and production efficiency is also low. Meanwhile, in TS12 backbone and TS15 backbone described in Patent Document 2, SeV vectors are removed by culturing infected cells under the culturing conditions of seven days at 39° C.; however, a longer time is required for removal at 37° C. and 28 days elapse until alkaline phosphatase-positive colonies are obtained from SeV vector infection. Moreover, the fact that vectors are not readily removed despite the assumption that iPS cell proliferation is fast and therefore vectors are easily removed, seems to suggest that a longer time is required for removal of vectors in conventional cell strains such as HeLa cells.

In regard to such problems, the present inventors have thought that by adding a degron to the viral protein of the SeV vector, removal of the SeV vector may be enhanced. In this regard, the present inventors first tried to remove the SeV vector by adding a degron to the L protein that was considered to be most suitable for enhancing removal of the vector by the degron among viral proteins of the SeV vector. However, when a degron was added to the L protein, in addition to adverse effect on reconstitution efficiency of recombinant viruses and production efficiency, the change in expression level of genes from the vectors caused by induction of destabilization through the degron was small and expression of transgenes and removal of the vectors were difficult to control effectively by adding the degron to the L protein.

In this regard, the present inventors have conducted experiment of adding a degron to the P protein of the SeV. As a result, they found that in the case of adding a degron to the P protein, significantly excellent characteristics are exerted, that is, very high level of expression of transgenes immediately after introduction of the vectors can be achieved, and thereafter, the vectors are rapidly removed. It has been found that in the case of a degron attached to GOI protein instead of the P protein, the expression level of GOI can be reduced only to about 1/10; on the other hand, in the case of using the vector of the present invention in which a degron is added to P protein, the expression level of GOI is dramatically reduced. In particular, by adding a degron, such as mTOR degron, DHFR degron, PEST, TetR degron, and mutants thereof, to the P protein, removal of the SeV vector at 37° C. is enhanced and reducing of the expression amount of GOI to zero is achieved.

Enhancement of removal of SeV vectors has been not only confirmed to be useful in vectors having reporter genes such as Azami-Green carried thereon, but also confirmed to be useful in SeV vectors for producing iPS cells, having transcription factor genes carried thereon. According to this, since target transcription factors and the like are transiently expressed in cells at high level in reprogramming of cells for the production of iPS cells, induction of differentiation of cells, and the like and then vectors can be rapidly removed, the vectors of the present invention can be expected to become gene expression vectors useful in modification of characteristics of cells in regenerative medicine, cell therapy, and the like.

That is, the present invention relates to a negative-strand RNA virus vector in which a degron is added to the P protein of the negative-strand RNA virus vector, and a use or the like thereof, and more specifically, the present invention is to provide the following inventions.

[1] A negative-strand RNA virus vector, in which the P gene of the vector has been modified so as to add a degron to the P protein of said virus.

[2] The vector described in [1], including a temperature-sensitive mutation in said P protein.

[3] The vector described in [2], in which said temperature-sensitive mutation includes L511F mutation.

[4] The vector described in [2] or [3], in which said temperature-sensitive mutation comprises D433A, R434A, and K437A.

[5] The vector described in any one of [1] to [4], in which the L protein of said virus includes L1361C and L1558I mutations.

[6] The vector described in any one of [1] to [5], in which the degron is selected from the group consisting of mTOR degron, dihydrofolate reductase (DHFR) degron, PEST, TetR degron, and auxin-inducible degron (AID).

[7] The vector described in any one of [1] to [5], in which the degron is mTOR degron.

[8] The vector described in any one of [1] to [5], in which the degron is PEST.

[9] The vector described in any one of [1] to [5], in which the degron is DHFR degron.

[10] The vector described in any one of [1] to [5], in which the degron is TetR degron.

[11] The vector described in any one of [1] to [10], in which the vector carries at least one exogenous gene.

[12] The vector described in [11], in which said exogenous gene encodes a protein added with a degron.

[13] The vector described in [12], in which the degron added to the protein encoded by said exogenous gene is different from the degron added to the P protein.

[14] The vector described in any one of [1] to [13], in which the vector carries at least two exogenous genes, and proteins encoded by each of the exogenous genes have a different degron added.

[15] The vector described in any one of [1] to [14], in which the negative-strand RNA virus is a *Paramyxovirus*.

[16] The vector described in [15], in which the *Paramyxovirus* is a Sendai virus.

[17] A method for enhancing removal of a negative-strand RNA virus vector, in which said method is characterized by using the vector described in any one of [1] to [16].

[18] The method described in [17], including a step of culturing at an elevated temperature to enhance removal.

[19] The method described in [17] or [18], including a step of culturing at 35 to 39° C. to enhance removal.

[20] A method of producing the vector described in any one of [1] to [16], in which the method includes a step of expressing a nucleic acid encoding genomic RNA of said vector, or a complementary strand thereof, under the presence of NP, P, and L protein, each of which does not have an added degron.

[21] A method of regulating expression amount of a gene carried, in which the method is characterized by using the vector described in [1] to [16].

[22] The method described in [21], in which the gene carried encodes a transcription factor.

[23] The method described in [21] or [22], in which said method is used in the preparation of pluripotent stem cells.

[24] A method of regulating the expression of an exogenous gene at a timing that is independent of vector removal, in which the method is characterized by using the vector described in [13] or [14].

[25] A method for enhancing removal of a negative-strand RNA virus or negative-strand RNA virus vector, in which the method comprises a step of co-infecting said virus or vector with the vector described in any one of [1] to [16].

[26] An agent for enhancing removal of a negative-strand RNA virus or a negative-strand RNA virus vector, in which the agent comprises the vector described in any one of [1] to [16].

Effects of the Invention

According to the present invention, it is possible to significantly enhance removal of the vector by adding a degron to the P protein. Both of a high gene expression amount and rapid removal of the vector are achieved, and effects of regulating transcription factor expression and enhancing removal of a vector in production of iPS cells can be obtained without culturing at high temperature.

BRIEF DESCRIPTION OF THE DRAWINGS

FIG. 1 is a view showing that sufficient gene expression is not obtained in a P gene-deficient vector without using P protein expressing cells. Fluorescence is not detected in parental cells (HeLa cells), but fluorescence of GFP is observed in P-expressing cells by infection of SeV18+GFP/dP.

FIG. 2 is a view showing expression regulation of ddAG in a SeV vector carrying DD-Azami Green (ddAG) in which a degron is added to the GOI protein. It is shown that basal expression cannot be suppressed by using only DD-tag.

FIG. 3 is a view showing the effect according to a position of ddAG carried in a SeV vector carrying ddAG. When the position of ddAG carried was moved rearward from F position to HNL position, a signal to noise ratio increased, but basal expression was still observed. That is, it is shown that basal expression cannot be suppressed even by combining the DD-tag and the position of GOI carried.

FIG. 4 is a view showing evaluation of PEST sequences of d1, d2, and d4. When d1, d2, or d4 GFP was carried at HNL position and comparison therebetween was carried out, the intensity of fluorescence was d4>d2>d1.

FIG. 5 is a view showing evaluation of SeV vectors carrying d2ddAG and d4ddAG. It is shown that basal expression of GOI protein cannot be suppressed even by combining PEST sequences of d2 and d4 and DD-tag.

FIG. 6 is a view showing expression regulation of d2ddAG and d2ddgRFP. It is shown that DD-tag and DDG-tag are carried on the same vector and independently controlled. d2ddAG and d2ddgRFP were independently controlled by Shield1 or trimethprime (TMP).

FIG. 7 is a view showing expression regulation of Tet-RAG. It was shown that TetR-tag was controlled by DOX. Expression of d2tetRAG from a SeV vector carrying d2tetRAG was induced by addition of DOX.

FIG. 8 is a view showing expression regulation of AGaid. Expression of AGaid from a SeV vector carrying AGaid was controlled by addition of Auxin.

FIG. 9 is a view showing expression regulation of SeV18+/PddTSΔF carrying BFP in which a degron is added to the P protein. After BHK cells were infected with BFP-Pdd, fluorescence of BFP was reduced by removal of Shield1 (through image analysis with ImageJ, reduction to 18% was confirmed).

FIG. 10 is a view showing expression regulation of SeV18+/LddTSΔF carrying BFP in which a degron is added to the L protein. After iPS cells were infected with BFP-Ldd, fluorescence of BFP was observed, but a fluorescence signal was weak and a change in fluorescence of BFP by removal of Shield1 was almost not observed. This indicates that Ldd does not function.

FIG. 11 is a view showing degradation evaluation of Pdd and ddP in which DD-tag is added to each of the C terminus and the N terminus of the P protein. Both Pdd and ddP are rapidly degraded.

FIG. 12 is a view showing expression regulation of SeV18+TIR1(HNL)d2AG/PaidTSΔF. HeLa cells were infected with a SeV vector carrying d2AG-Paid, and it was confirmed that reduction of d2AG by addition of IAA was observed.

FIG. 13 is a view showing, with FACS, enhancement of removal of SeV18+d2AGPddTS15ΔF. Fluorescence of d2AG-PddTS15 was lost on day 7 after increasing the temperature to 37° C.; on the other hand, remaining of fluorescence of the conventional temperature-sensitive vector was observed even in some cells on day 21. Furthermore, regardless of addition of a degron, d2AG-PddTS15 at 35° C. showed a higher fluorescence value than that of the conventional vector (TS15). That is, it is shown that SeV vectors carrying PddTS15 have higher expression amount than that of the conventional vector (TS15) and removal thereof is enhanced.

FIG. 14 is a view showing, with SeV antibody staining, enhancement of removal of SeV18+d2AG/PddTS15ΔF. d2AG-PddTS15 was negative for staining with the SeV antibody on day 14 after increasing the temperature to 37° C. On the other hand, conventional TS15 vector was positive for staining with the SeV antibody on day 14.

FIG. 15 is a view showing expression regulation and removal enhancement of SeV18+d2AG/PddTS15ΔF at 35 to 39° C. With the temperature-sensitive P added with DD-tag, a decrease in expression of the carried gene was observed at 35 to 39° C., and loss of the carried gene was observed at 37 to 39° C.

FIG. 16 is a view showing expression regulation and removal enhancement of SeV18+d2AG/PddgTS15ΔF. In FIG. 16(*a*), with the temperature-sensitive P added with DDG-tag, a decrease in expression of the carried gene was observed at 37° C. In FIG. 16(*b*), a decrease in expression and loss of the carried gene were observed even at 35 to 39° C. by removal of TMP.

FIG. 17 is a view showing expression regulation and removal enhancement of SeV18+d2AG/PtetRTS15ΔF at 35 to 39° C. With the temperature-sensitive P added with TetR-tag, a decrease in expression and loss of the carried gene were observed at 35 to 39° C. While DD-tag was expressed at 35° C., loss of expression was observed in TetR-tag.

FIG. 18 is a view showing expression regulation and removal enhancement of SeV18+d2AG/d4PTS15ΔF at 35 to 39° C. With the temperature-sensitive P added with d4 of PEST sequence, a decrease in expression of the carried gene was observed at 35 to 39° C., and loss of the carried gene was observed at 37 to 39° C.

FIG. 19 is a view showing removal enhancement of SeV18+d2AG/d2PTS12ΔF and SeV18+d2AG/PddTS15ΔF. By adding a PEST sequence or DD-tag to the temperature-sensitive P, as compared to the conventional TS12 vector, removal enhancement or loss of the carried gene was observed at 38.5° C.

FIG. 20 is a view showing expression regulation and removal enhancement of SeV18+d2AG/d2PTS15ΔF and SeV18+d2AG/d4PTS15ΔF. By adding a PEST sequence to the temperature-sensitive P, a decrease in expression and loss of the carried gene were observed at 37° C.

FIG. 21 is a view showing, with FACS, expression regulation and removal enhancement of SeV18+d2AG/d2PTS15ΔF and SeV18+d2AG/d4PTS15ΔF. By adding a PEST sequence to the temperature-sensitive P, a decrease in expression of the carried gene was observed at 37° C. Furthermore, regardless of addition of a degron, d2AG-d2PTS15 at 35° C. showed the same fluorescence value as that of the conventional vector (TS15).

FIG. 22 is a view showing, with FACS, removal enhancement of SeV18+d2AG/d2PTS15ΔF. Fluorescence of d2AG-d2PTS15 was lost on day 7 after increasing the temperature to 37° C.; on the other hand, remaining of fluorescence of the conventional temperature-sensitive vector was observed in some cells even on day 21. Furthermore, regardless of addition of a degron, d2AG-d2PTS15 at 35° C. showed the same fluorescence value as that of the conventional vector (TS15). That is, it is shown that the vector containing the P protein added with a PEST sequence has the same expression amount as that of the conventional vector (TS15) and removal thereof is enhanced.

FIG. 23 is a view showing, with PCR, enhancement of removal of a vector in which a degron is added to the P protein. In d2AG-PddTS15 and d2AG-d2PTS15, SeV was not detected on day 21 after increasing the temperature to 37° C.; on the other hand, remaining of SeV was detected in conventional TS15.

FIG. 24 is a view showing, with real-time PCR, enhancement of removal of a vector in which a degron is added to the P protein. In real-time PCR of SeV, d2PTS15 and PddTS15 were not detected on day 21. On the other hand, the conventional vector TS15 was gradually reduced but it was confirmed that it remained even on day 21. The value of PddTS15 on day 3 was higher than that of TS15 by 30 times or more.

FIG. 25 is a view showing, with alkaline phosphatase staining, production of iPS cells by carrying transcription factors on vectors in which a degron is added to the P protein. Similarly to CytoTune-iPS 2.0, ALP positive colonies were confirmed also in d2P, Pdd, Pddg, and PtetR.

FIG. 26 is a view showing, with SeV antibody staining, enhancement of removal of vectors from iPS cells produced by using vectors in which a degron is added to the P protein. d2P was negative for staining with SeV antibody at P=2 (the second passage).

FIG. 27 is a view showing, with real-time PCR, enhancement of removal of vectors from iPS cells produced by using vectors in which a degron is added to the P protein. In d2P, SeV was not detected at P=3 (the third passage).

FIG. 28 is a view showing, with PCR, undifferentiation marker expression and removal of vectors in iPS cells produced by using vectors (d2P) in which a degron is added to the P protein. Similarly to CytoTune-iPS 2.0, expression of NANOG and TERT was confirmed with d2P. Furthermore, removal of SeV was confirmed.

FIG. 29 is a view showing three germ layer formation ability of the induced iPS cells. iPS cells obtained in Example 22 (FIG. 28) were transplanted to the NOD-scid mice, and three germ layer formation ability of teratoma was observed.

FIG. 30 is a view showing, with PCR, undifferentiation marker expression and removal of vectors in iPS cells produced by using vectors (Pdd, Pddg, and PtetR) in which a degron is added to the P protein. Similarly to CytoTune-iPS 2.0, expression of NANOG and TERT was confirmed with Pdd, Pddg, and PtetR. Furthermore, removal of SeV was confirmed.

FIG. 31 is a view showing enhancement of removal by co-infecting a vector in which a degron is added to the P protein with a conventional vector. As compared to TS15 only, fluorescence of d2AG was reduced to 60%6 by co-infection with PtetR. Meanwhile, by increasing the infection dose of the TS15 vectors twice, fluorescence of d2AG was increased to 118%.

FIG. 32 is a view showing gene expression of the P protein in which the N terminus side is chipped off. The P protein in which the N terminus side is chipped off was expressed in HeLa cells and GFP/dP was infected thereto. Even when the N terminus side is chipped off, the P protein can be functional.

FIG. 33 is a view showing that the effect of the present invention was confirmed in various negative-strand RNA virus vectors. A degron and Halo-tag were added to the P proteins of Sendai virus (SeV), measles virus (MeV). Newcastle disease virus (NDV), parainfluenza virus 2 (PIV2), and vesicular stomatitis virus (VSV), and it was confirmed whether the vectors were removed by the degron similarly to Example 11. As a result, it was confirmed that the vectors were mostly degraded after one hour from removal of the reagents.

FIG. 34*a* is a view showing independent expression control of exogenous genes. Two exogenous genes controlled by different degrons were inserted into the vector of the present invention in which a degron is added to the P protein. Expression of each gene can be controlled independently from the vectors.

FIG. 34*b* is a view showing independent expression control of exogenous genes. Two exogenous genes controlled by different degrons were inserted into the vector of the present invention in which a degron is added to the P protein. Expression of each gene can be controlled independently from the vectors.

FIG. 35 is a view showing expression regulation of SeV18+/PddΔF carrying DGFP in which a degron is added to the P protein. After HeLa cells were infected with DGFP-Pdd/dF, fluorescence of DGFP was reduced by not adding Shield1 (reduction to 40% was confirmed by image analysis with MetaMorph).

MODE FOR CARRYING OUT THE INVENTION

Hereinafter, embodiments of the present invention will be described in detail.

The present invention provides a negative-strand RNA virus vector in which a degron is added to the P protein of the negative-strand RNA virus, a method for producing a vector, a use of a vector, a method for enhancing removal of a vector and the like.

The negative-strand RNA virus vector refers to a virus vector derived from a virus containing a minus-strand (strand encoding a viral protein in antisense) RNA as the genome. The minus-strand RNA is also called negative-strand RNA. In particular, the negative-strand RNA viruses of the present invention include single-stranded negative-strand RNA viruses (also referred to as non-segmented negative-strand RNA viruses) as examples. The single-stranded negative-strand RNA viruses refer to viruses having a single-stranded negative-strand (that is, minus-strand) RNA as the genome. Such viruses include viruses belonging to families such as Paramyxoviridae (including the genera *Paramyxovirus, Morbillivirus, Rubulavirus*, and *Pneumovirus*), Rhabdoviridae (including the genera *Vesiculovirus, Lyssavirus*, and *Ephemerovirus*), and Filoviridae, and taxonomically belong to Mononegavirales (Virus, Vol. 57(1), pp 29-36, 2007; Annu. Rev. Genet. 32, 123-162, 1998; Fields Virology Fourth Edition, Philadelphia, Lippincott-Raven, 1305-1340, 2001; Microbiol. Immunol. 43, 613-624, 1999; Field Virology, Third edition pp. 1205-1241, 1996).

Examples of preferred negative-strand RNA virus vectors in the present invention include *paramyxovirus* vectors and rhabdovirus vectors. The *paramyxovirus* in the present invention refers to a virus belonging to Paramyxoviridae or a derivative thereof. The Paramyxoviridae is one of viral groups having non-segmented negative-strand RNA as the genome and includes Paramyxovirinae (the genera *Respirovirus* (also referred to as the genus *Paramyxovirus*), *Rubulavirus*, and *Morbillivirus*) and Pneumovirinae (including the genera *Pneumovirus* and *Metapneumovirus*). Specific examples of the viruses included in Paramyxoviridae viruses include Sendai virus, Newcastle disease virus, Mumps virus, Measles virus, Respiratory synctial virus (RS virus), rinderpest virus, distemper virus, simian parainfluenza virus (SV5), and human parainfluenza viruses I, II, and III. More specific examples include Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MeV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). As Rhabdoviridae, Vesicular stomatitis virus and Rabies virus belonging to the Rhabdoviridae family, and the like are included.

The viruses of the present invention are preferably viruses belonging to the Paramyxovirinae (including the genera *Respirovirus, Rubulavirus*, and *Morbillivirus*) or derivatives thereof, and more preferably viruses belonging to the genus *Respirovirus* (also referred to as the genus *Paramyxovirus*) or derivatives thereof. Derivatives include chemically modified viruses and viruses whose viral genes have been modified such that the gene transfer ability of the virus is not impaired. Examples of *Respirovirus* viruses to which the present invention can be applied include human parainfluenza virus 1 (HPIV-1), human parainfluenza virus 3 (HPIV-3), bovine parainfluenza virus 3 (BPIV-3), Sendai virus (also called mouse parainfluenza virus 1), measles virus, simian parainfluenza virus (SV5), and simian parainfluenza virus 10 (SPIV-10). The *paramyxovirus* in the present invention is most preferably Sendai virus.

The negative-strand RNA virus typically contains a complex comprising RNA and protein in the interior of the envelope (ribonucleoprotein; RNP). The RNA included in RNP is (−)-strand (negative-strand) single-stranded RNA that is a genome of the negative-strand RNA virus and this single-stranded RNA is bound to NP protein, P protein, and L protein to form RNP. The RNA included in this RNP is used as template for transcribing and replicating the viral genome (Lamb, R. A., and D. Kolakofsky, 1996, Paramyxoviridae: The viruses and their replication. pp. 1177-1204. In Fields Virology, 3rd edn. Fields, B. N., D. M. Knipe, and P. M. Howley et al. (ed.). Raven Press, New York, N.Y.).

The "NP, P, M, F, HN, and L genes" of the negative-strand RNA virus refer to genes encoding nucleocapsid, phospho, matrix, fusion, hemagglutinin-neuraminidase, and large proteins, respectively. The nucleocapsid (NP) protein is bound to the genomic RNA and is an essential protein in order for the genomic RNA to have template activity. In general, the NP gene is also described as "N gene" in some cases. The phospho (P) protein is a phosphorylated protein that is a small subunit of RNA polymerase. The matrix (M) protein exhibits the function of maintaining the virus particle structure from the interior side. The fusion (F) protein is a membrane fusion protein involved in the penetration into host cells, and the hemagglutinin-neuraminidase (HN) protein is a protein involved in binding with host cells. The large (L) protein is a large subunit of RNA polymerase. Each of the above-described genes has a transcriptional regulation unit, and single mRNA is transcribed from each gene and then the protein is translated. From the P gene, in addition to the P protein, non-structural protein (C) translated by using different ORF and protein (V) formed by RNA editing during reading P protein mRNA are translated. For example, respective genes in each virus belonging to Paramyxovirinae are described as follows in the order from 3'.

the genus *Respirovirus* N P/C/V M F HN-L
the genus *Rubulavirus* N P/V M F HN (SH) L
the genus *Morbillivirus* N P/C/V M F H-L For examples of accession numbers in the database for the nucleotide sequences of Sendai virus genes, see M29343, M30202, M30203, M30204, M51331, M55565, M69046, and X17218 for the N gene; M30202, M30203, M30204, M55565, M69046, X00583, X17007, and X17008 for the P gene; D11446, K02742, M30202, M30203, M30204, M69046, U31956, X00584, and X53056 for the M gene; D00152, D11446, D17334, D17335, M30202, M30203, M30204, M69046, X00152, and X02131 for the F gene; D26475, M12397, M30202, M30203, M30204, M69046, X00586, X02808, and X56131 for the HN gene; and D00053, M30202, M30203, M30204, M69040, X00587, and X58886 for the L gene. Examples of viral genes encoded by other viruses may include CDV, AF014953; DMV, X75961; HPIV-1, D01070; HPIV-2, M55320; HPIV-3, D10025; Mapuera, X85128; Mumps, D86172; MeV, K01711; NDV, AF064091; PDPR, X74443; PDV, X75717; RPV, X68311; SeV, X00087; SV5, M81442; and Tupaia, AF079780 for the N gene; CDV, X51869; DMV, Z47758; HPIV-1, M74081; HPIV-3, X04721; HPIV-4a, M55975; HPIV-4b, M55976; Mumps, D86173; MeV, M89920; NDV, M20302; PDV, X75960; RPV, X68311; SeV, M30202; SV5, AF052755; and Tupaia, AF079780 for the P gene; CDV, AF014953; DMV, Z47758; HPIV-1, M74081; HPIV-3, D00047; MeV, ABO16162; RPV, X68311; SeV, AB005796; and Tupaia, AF079780 for the C gene; CDV, M12669; DMV Z30087; HPIV-1, S38067; HPIV-2, M62734; HPIV-3, D00130; HPIV-4a, D10241; HPIV-4b, D10242; Mumps, D86171; MeV, AB012948; NDV, AF089819; PDPR, Z47977; PDV, X75717; RPV, M34018; SeV, U31956; and SV5, M32248 for the M gene; CDV, M21849; DMV, AJ224704; HPN-1, M22347; HPIV-2, M60182; HPIV-3, X05303, HPIV-4a, D49821; HPIV-4b, D49822; Mumps, D86169; MeV, AB003178; NDV, AF048763; PDPR, Z37017; PDV, AJ224706; RPV, M21514; SeV, D17334; and SV5, AB021962 for the F gene; CDV, AF112189; DMV, AJ224705; HPIV-1, U709498; HPIV-2, D000865; HPIV-3, AB012132; HPIV-4A, M34033; HPIV-4B, AB006954; Mumps, X99040; MeV, K01711; NDV, AF204872; PDPR, X74443; PDV, Z36979; RPV, AF132934; SeV, U06433; and SV-5, S76876 for the HN (H or G) gene; and CDV, AF014953; DMV, AJ608288; HPIV-1, AF117818, HPIV-2, X57559; HPIV-3, AB012132; Mumps, AB040874; MeV, K01711; NDV, AY049766; PDPR, AJ849636; PDV, Y09630; RPV, Z30698; and SV-5, D13868 for the L gene. However, multiple strains are known for each of the viruses, and genes consisting of a sequence other than those exemplified above may exist due to strain differences. Sendai virus vectors carrying viral genes derived from any of these genes are useful as vectors of the present invention. In addition, regarding the P protein, the functional site thereof is a region including the N binding site, the L binding site, and the oligomer forming site at the C terminus side (in the case of SeV, 320-568 at the C terminus side of the P protein) (Blanchard L. et al., Virology. (2004) 319, 201-211). The P protein of the present invention preferably includes at least this region. For example, the vectors of the present invention contain a nucleotide sequence having 90% or higher, preferably 95% or higher, 96% or higher, 97% or higher, 98% or higher, or 99% or higher identity to the coding sequence of any of the above-mentioned viral genes (regarding the P gene of SeV, for example, may be the sequence at the C terminus side, for example, amino acid sequences shown in SEQ ID NOS: 479 to 568 or amino acid sequences shown in SEQ ID NOS: 320 to 568). Furthermore, the vectors of the present invention contain, for example, a nucleotide sequence encoding an amino acid sequence having 90% or higher, preferably 95% or higher, 96% or higher, 97% or higher, 98% or higher, or 99% or higher identity to an amino acid sequence encoded by the coding sequence of any one of the above-mentioned viral genes (regarding the P protein of SeV, for example, may be the sequence at the C terminus side, for example, amino acid sequences shown in SEQ ID NOS: 479 to 568 or amino acid sequences shown in SEQ ID NOS: 320 to 568). Furthermore, the vectors of the present invention contain, for example, a nucleotide sequence encoding polypeptide including a nucleotide sequence encoding an amino acid sequence with ten or less, preferably nine or less, eight or less, seven or less, six or less, five or less, four or less, three or less, two or less, or one amino acid substitutions, insertions, deletions, and/or additions in an amino acid sequence encoded by the coding sequence of any one of the above-mentioned viral genes (regarding the P protein of SeV, for example, may be the sequence at the C terminus side, for example, amino acid sequences shown in SEQ ID NOS: 479 to 568 or amino acid sequences shown in SEQ ID NOS: 320 to 568). The vectors modified so as to add a degron to the P protein encoded by such vectors are favorable as the vectors of the present invention.

The sequences referenced by the database accession numbers such as the nucleotide sequences and amino acid sequences described herein refer to sequences on, for example, the filing date and priority date of this application, and can be identified as sequences at the time of either the filing date or priority date of the present application, and are preferably identified as sequences on the filing date of this application. The sequences at the respective time points can be identified by referring to the revision history of the database.

Furthermore, negative strand RNA viruses of the present invention may be derived from natural strains, wild-type strains, mutant strains, laboratory-passaged strains, and artificially constructed strains and such. An example is the Sendai virus Z strain (Medical Journal of Osaka University Vol. 6, No. 1, March 1955 p 1-15). That is, these viruses may be virus vectors having similar structures as viruses isolated from nature, or viruses artificially modified by genetic recombination, as long as the desired reprogramming can be induced. For example, they may have mutations or deletions in any of the genes of the wild-type virus. For example, viruses having a mutation or deletion in at least one gene encoding a viral envelope protein or a coat protein can be preferably used. Such virus vectors are, for example, virus vectors that can replicate the genome in infected cells but cannot form infectious virus particles. Since there is no worry of spreading the infection to the surroundings, such transmission-defective virus vectors are highly safe. For example, negative-strand RNA viruses that do not contain at least one gene encoding an envelope protein such as F and/or HN or a spike protein, or a combination thereof may be used (WO 00/70055 and WO 00/70070; Li, H.-O. et al., J. Virol. 74(14): 6564-6569 (2000)). If proteins necessary for genome replication (for example, N, P, and L proteins) are encoded in the genomic RNA, the genome can be amplified in infected cells. To produce defective type of viruses, for example, the defective gene product or a protein that can complement it is externally supplied in the virus-producing cell (WO 00/70055 and WO 00/70070; Li. H.-O. et al., J. Virol. 74(14): 6564-6569 (2000)). Furthermore, a method of collecting virus vectors as noninfective virus particles (VLP) without completely complementing the defective viral protein is also known (WO 00/70070). Furthermore, when virus vectors are collected as RNPs (for example, RNPs containing the N, L, and P proteins and genomic RNA), vectors can be produced without complementing the envelope proteins.

The viruses of the present invention are not limited to natural viruses, and for example, artificially produced viruses are also included. For example, in the viruses of the present invention, those in which mutations are introduced into nucleic acid sequences in order to optimize codon, chimeric viruses (for example, including chimeras between homogeneous viruses and chimeric viruses between heterogeneous viruses (for example, chimeras between PIV and SeV, and the like)) are also included (J. Virol. 1995, 849-855).

Furthermore, in the present invention, viral proteins such as N, L, and P proteins may not be wild type as long as they maintain the function of expressing genes in transduced cells. For example, modified proteins appropriately added with a peptide such as a tag, proteins having modified codon, proteins in which a part of amino acid sequence of wild type protein is deleted so as not to lose the function, and the like can be appropriately used. In the present invention, such modified proteins and deleted proteins are also included in the N, L, and P proteins. For example, other regions are not essential in expression of virus vectors as long as the P protein has a part of the C terminus.

In the present invention, the negative-strand RNA virus vector is a vector having genome nucleic acid derived from the virus and capable of expressing transgene by inserting the transgene into the nucleic acid. In the present invention, the negative-strand RNA virus vector includes infectious virus particles, as well as complexes of the viral core, viral genome, and viral protein, and complexes comprising non-infectious viral particles and such, which are complexes having the ability to express carried genes upon introduction into cells.

In the vector of the present invention in which a degron is added to the negative-strand RNA virus structure protein (hereinafter, referred to as the "vector of the present invention"), the removal speed of the vector is increased by modifying (−)-strand single-stranded RNA such that degradation of proteins to be bound to the (−)-strand single-stranded RNA is enhanced. In the present invention, the proteins to be bound to the (−)-strand single-stranded RNA refer to proteins to be bound directly and/or indirectly to the (−)-strand single-stranded RNA to form complexes with the (−)-strand single-stranded RNA. In the complexes of the present invention, complexes comprising (−)-strand single-stranded RNA derived from negative-strand RNA viruses and proteins derived from negative-strand RNA viruses bound thereto (for example, NP, P, and L proteins) are included. In the present invention, "derived from negative-strand RNA viruses" means that constituents (including proteins and RNAs) of negative-strand RNA viruses are in a state of not being changed or being partially modified. For example, proteins or RNAs produced by modifying proteins or RNAs of negative-strand RNA viruses are proteins or RNAs "derived from negative-strand RNA viruses". The types of vectors of the present invention are not limited as long as they have the aforementioned characteristics. For example, the vectors of the present invention may be virus vectors having envelope proteins (F, HN, and M proteins) or the like and a structure of virus particles. Moreover, the vectors of the present invention may be RNP vectors, which are RNP itself, not having viral envelopes.

In the negative-strand RNA viruses, NP, P, and L proteins are bound to (−)-strand single-stranded RNA and exhibit the function essential in genomic RNA replication and protein expression (hereinbelow, in some cases, the NP, P, and L proteins are referred to as "genomic RNA-bound proteins"). The NP protein is a protein that is very firmly bound to genomic RNA and provides template activity to the genomic RNA. The genomic RNA has template activity of RNA synthesis only in a state of being bound to the NP protein, and does not have template activity at all in a state of being not bound to the NP protein. The P protein is bound, as the small subunit of RNA polymerase, to the genomic RNA and the L protein is bound, as the large subunit of RNA polymerase, to the genomic RNA. For this reason, in the negative-strand RNA viruses, if any one of NP, P, and L proteins is deficient, replication of the genomic RNA does not occur.

Such an embodiment of the vector of the present invention is characterized by containing (a) (−)-strand single-stranded RNA, which is modified so as to add a degron to one or more proteins selected from NP protein, P protein, and L protein that are proteins to bind to negative-strand RNA virus (−)-strand single-stranded RNA, derived from a negative-strand RNA virus; and (b) a complex comprising NP protein, P protein, and L protein. That is, it is preferable to modify a genomic RNA-bound protein (NP protein, P protein, and/or L protein) encoded in the modified (−)-strand single-stranded RNA such that a degron is added thereto. The vectors of the present invention may be virus particles containing the modified (−)-strand single-stranded RNA (genomic RNA) and a complex comprising NP, P, and L proteins (RNP). The (−)-strand single-stranded RNA contained in the vector of the present invention is modified so as to add a degron to at least the P protein. When the host is infected with the vector of the present invention, proteins are expressed from genes encoded in the genomic RNA by the operation of the NP, P, and L proteins contained in the vector of the present invention. However, in the vector of the present invention in which a degron is added to the P protein having intensified temperature sensitivity, loss of the function of the P protein is enhanced by an increase in temperature and destabilization of the degron. Therefore, the formation of the virus particles (particles containing genomic RNA and NP, P, and L proteins) that is self-replicated is stopped by an increase in temperature and destabilization of the degron. That is, the vector of the present invention is an ultra-temperature-sensitive virus vector. When exogenous genes are carried on the vectors of the present invention and infected to the host, the exogenous genes are expressed in the host cells, however, thereafter, production of the virus particles having self-replicating ability from the vectors of the present invention is stopped by combination of an increase in temperature and destabilization of the degron, and thus removal of the vectors from the cells is enhanced so that expression of the exogenous genes is also stopped.

The genes encoded in the genomic RNA of the vector of the present invention may have virus-derived gene sequences without any change or may be introduced with any mutations. For example, a person skilled in the art can introduce a minor mutation that does not impair the function of each protein into each gene on the genomic RNA by known methods. For example, mutations can be site-specifically introduced by a PCR method, a cassette mutagenesis method, and the like, or random mutations can be introduced by chemical reagents, random nucleotides, and the like.

For example, in the envelope protein and the spike protein, many mutations including attenuation mutations and temperature-sensitive mutations are known. Viruses having these mutation protein genes can be favorably used in the present invention. In the present invention, vectors with lowered cytotoxicity are desirably used. Cytotoxicity of the vectors can be measured, for example, by quantifying the release of lactic acid dehydrogenase (LDH) from vector infected cells. As the release level of LDH decreases, cytotoxicity is lowered. For example, vectors with significantly lowered cytotoxicity compared to the wild type can be used. Regarding the degree of lowering of cytotoxicity, for example, vectors showing a significant decrease of, for example, 20% or higher, 25% or higher, 30% or higher, 35% or higher, 40% or higher, or 50% or higher in the LDH release level compared to the wild type in a culture medium of human-derived HeLa cell (ATCC CCL-2) or simian-derived CV-1 cell (ATCC CCL 70) infected at MOI (multiplicity of infection) 3 and cultured for three days at 35 to 37° C. (for example, 37° C.) can be used. Furthermore, mutations that decrease cytotoxicity also include temperature-sensitive mutations.

Further, the temperature sensitivity can be determined by measuring the viral proliferation rate or the expression level of the carried gene at the viral host's ordinary temperature (for example, 37° C. to 38° C.). As the viral proliferation rate and/or the expression level of the carried gene decrease, as compared to those not having a mutation, the temperature sensitivity is determined to be high.

A virus vector used in the present invention has deletions or mutations in preferably at least one, more preferably at least 2, 3, 4, 5, or more viral genes. Deletions and mutations may be arbitrarily combined and introduced to each of the genes. Herein, a mutation may be a function-impairing mutation or a temperature-sensitive mutation, and is a mutation that decreases the viral proliferation rate or the expression level of any of the carried genes to preferably ½ or less, more preferably ⅓ or less, more preferably ⅕ or less, more preferably 1/10 or less, and more preferably 1/20 or less compared to the wild type at least at 37° C. The use of such modified virus vectors can be useful particularly in terms that cytotoxicity in the host cells can be lowered or the removal of the vector can be enhanced. For example, virus vectors used favorably in the present invention have at least two deleted or mutated viral genes. Such viruses include those with deletions of at least two viral genes, those with mutations in at least two viral genes, and those with a mutation in at least one viral gene and a deletion of at least one viral gene. The at least two mutated or deleted viral genes are preferably genes encoding envelope-constituting proteins. For example, the negative-strand RNA virus vectors of the present invention are preferably to have deficiency of at least the F gene, and more preferably those with deletion of the F gene with further deletion of the M and/or the HN gene or further mutation (for example, temperature-sensitive mutation) in the M and/or the HN gene are used favorably in the present invention. Furthermore, vectors used in the present invention more preferably have at least three deleted or mutates viral genes (preferably at least three genes encoding envelope-constituting proteins; F, HN, and M). Such virus vectors include those with deletion of at least three genes, those with mutations in at least three genes, those with mutations in at least one gene and deletion of at least two genes, and those with mutations in at least two genes and deletion of at least one gene. As examples of more preferred embodiments, vectors with deletion of the F gene with further deletion of the M and the HN gene or further mutations (for example, temperature-sensitive mutations) in the M and the HN gene are used favorably in the present invention. Furthermore, for example, vectors with deletion of the F gene with further deletion of the M or the HN gene and further mutation in the remaining M or HN gene (for example, temperature-sensitive mutation) are used favorably in the present invention. Such mutated-form viruses can be produced according to known methods.

For example, a temperature-sensitive mutation of the M gene of Sendai virus includes amino acid substitution of site arbitrarily selected from the group consisting of position 69 (G69), position 116 (T116), and position 183 (A183) of the M protein or amino acid substitutions of equivalent sites of the negative-strand RNA virus M protein (Inoue, M. et al., J. Virol. 2003, 77: 3238-3246). Viruses having a genome encoding a mutant M protein, in which the amino acids of any one site, preferably a combination of any two sites, or more preferably all three sites of the three sites mentioned above are substituted in the Sendai virus M proteins to other amino acids, are used preferably in the present invention.

Preferred amino acid mutations are substitution to other amino acids with a side chain having different chemical properties, and examples are substitution to an amino acid with a BLOSUM62 matrix (Henikoff, S. and Henikoff, J. G. (1992) Proc. Natl. Acad. Sci. USA 89: 10915-10919) score of three or less, preferably two or less, more preferably one or less, and even more preferably 0. Specifically. G69, T116, and A 183 of the Sendai virus M protein can be substituted to Glu (E), Ala (A), and Ser (S), respectively. Regarding other negative-strand RNA virus M proteins, amino acids of equivalent sites can also be substituted to Glu (E), Ala (A), and Ser (S), respectively. Furthermore, mutations homologous to mutations in the M protein of the temperature-sensitive P253-505 measles virus strain (Morikawa, Y et al., Kitasato Arch. Exp. Med. 1991: 64; 15-30) can also be used. Mutations can be introduced according to known mutation methods, for example, using oligonucleotides and the like.

Furthermore, examples of temperature-sensitive mutations in the HN gene include amino acid substitution of a site arbitrarily selected from the group consisting of position 262 (A262), position 264 (G264), and position 461 (K461) of the HN protein of a Sendai virus, or amino acid substitution of equivalent site of the negative-strand RNA virus HN protein (Inoue. M. et al., J. Virol. 2003, 77: 3238-3246). Viruses having a genome encoding a mutant HN protein in which the amino acids of any one of the three sites, preferably a combination of any two sites, or more preferably all three sites are substituted to other amino acids are used preferably in the present invention. As mentioned above, preferred amino acid substitutions are substitutions to other amino acids with a side chain having different chemical properties. As a preferred example, A262, G264, and K461 of the Sendai virus HN protein are substituted to Thr (T), Arg (R), and Gly (G), respectively. Regarding the other negative-strand RNA virus M proteins, the amino acids of equivalent sites can be substituted to Thr (T), Arg (R), and Gly (G), respectively. Furthermore, for example, using the temperature-sensitive vaccine strain Urabe AM9 of the mumps virus as a reference, amino acids at positions 464 and 468 of the HN protein can be mutated (Wright, K. E. et al., Virus Res. 2000: 67; 49-57).

Furthermore, the vectors of the present invention may have mutations in the P gene and/or the L gene. Examples of such mutations are specifically, mutation of Glu at position 86 (E86) in the SeV P protein, and substitution of Leu at position 511 (L511) in the SeV P protein to other amino acids. Regarding the other negative-strand RNA virus P proteins, substitutions of equivalent sites are exemplified. As mentioned above, preferred amino acid substitutions are substitution to other amino acids with a side chain having different chemical properties. Specific examples may include substitution of the amino acid at position 86 to Lys, and substitution of the amino acid at position 511 to Phe. Furthermore, examples in the L protein include substitution of Asn at position 1197 (N1197) and/or Lys at position 1795 (K1795) in the SeV L protein to other amino acids, and substitutions of equivalent sites in other negative-strand RNA virus L proteins, and similarly as above, preferred amino acid substitutions are substitutions to other amino acids with a side chain having different chemical properties. Specific examples are substitution of the amino acid at position 1197 to Ser, and substitution of the amino acid at position 1795 to Glu. Mutations of the P gene and L gene can significantly increase the effects of sustained infectivity, suppression of release of secondary particles, or suppression of cytotoxicity. Further, combination of mutations and/or deficiencies of envelope protein genes can dramatically increase these effects. Furthermore, examples for the L gene include substitution of Tyr at position 1214 (Y1214) and/or substitution of Met at position 1602 (M1602) of the SeV L protein to other amino acids, and substitutions of equivalent sites in other negative-strand RNA virus L proteins, and similarly as above, preferred amino acid substitutions are substitutions to other amino acids with a side chain having different chemical properties. Specific examples are substitutions of the amino acid at position 1214 to Phe, and substitutions of the amino acid at position 1602 to Leu. The above-mentioned mutations can be arbitrarily combined.

For example, Sendai virus vectors in which at least G at position 69, T at position 116, and A at position 183 of the SeV M protein, at least A at position 262, G at position 264, and K at position 461 of the SeV HN protein, at least L at position 511 of the SeV P protein, and at least N at position 1197 and K at position 1795 of the SeV L protein are substituted to other amino acids, and in which the F gene is also deficient or deleted; and F-gene-deficient or -deleted Sendai virus vectors whose cytotoxicity is similar to or lower than those mentioned above and/or whose temperature sensitivity is similar to or higher than those mentioned above are particularly preferred. Regarding other negative-strand RNA viruses, vectors in which equivalent sites are substituted and the F gene is deficient or deleted; and F-gene-deficient or -deleted vectors whose cytotoxicity is similar to or lower than those mentioned above and/or whose temperature sensitivity is similar to or higher than those mentioned above are preferred. Specific examples of the substitutions may include G69E, T116A, and A183S substitutions for the M protein, A262T, G264R, and K461G substitutions for the HN protein, L511F substitution for the P protein, and N1197S and K1795E for the L protein.

Amino acid mutations may be substitutions to other desired amino acids, but preferably, as mentioned above, are substitutions to other amino acids with a side chain having different chemical properties. For example, the amino acids can be classified into groups such as basic amino acids (for example, lysine, arginine, and histidine), acidic amino acids (for example, aspartic acid and glutamic acid), non-charged polar amino acids (for example, glycine, asparagine, glutamine, serine, threonine, tyrosine, and cysteine), nonpolar amino acids (for example, alanine, valine, leucine, isoleucine, proline, phenylalanine, methionine, and tryptophan), β-branched amino acids (for example, threonine, valine, and isoleucine), and aromatic amino acids (for example, tyrosine, phenylalanine, tryptophan, and histidine), but regarding a certain amino acid, substitutions to other amino acids other than the group to which the certain amino acid belongs are exemplified. Specifically, substitutions to acidic or neutral amino acids for basic amino acids, substitutions to nonpolar amino acids for polar amino acids, and in the case of amino acids having a larger molecular weight than the average molecular weight of 20 types of natural amino acids, substitutions to amino acids having a lower average molecular weight than the average molecular weight of amino acids having a larger molecular weight, conversely, in the case of substitutions to amino acids having a lower molecular weight than the average molecular weight of the natural amino acids, substitutions to amino acids having a larger average molecular are exemplified, but substitutions are not limited thereto.

Further, examples of mutations of the L protein include substitutions of amino acids at sites arbitrarily selected from position 942 (Y942), position 1361 (L1361), and position 1558 (L1558) of the SeV L protein or equivalent sites of negative-strand RNA virus L protein to other amino acids. Similarly as above, preferred amino acid substitutions are substitutions to other amino acids with a side chain having different chemical properties. Specific examples may include substitution of the amino acid at position 942 to His, substitution of the amino acid at position 1361 to Cys, and substitution of the amino acid at position to Ile. In particular, the L protein with substitutions at least at positions 942 or 1558 can be used preferably. For example, mutant L proteins in which, in addition to position 1558, position 1361 is also substituted to another amino acid are preferred as well. Furthermore, mutant L proteins in which, in addition to position 942, position 1558 and/or position 1361 are also substituted to other amino acids are favorable as well. These mutations can increase the temperature sensitivity of the L protein.

Examples of mutations of the P protein include substitutions of amino acids at sites arbitrarily selected from position 433 (D433), position 434 (R434), and position 437 (K437) of the SeV P protein or equivalent sites of negative-strand RNA virus P protein to other amino acids. Similarly as above, preferred amino acid substitutions are substitutions to other amino acids with a side chain having different chemical properties. Specific examples include substitution of the amino acid at position 433 to Ala (A), substitution of the amino acid at position 434 to Ala (A), and substitution of the amino acid at position 437 to Ala (A). In particular, P proteins in which all three of these sites are substituted can be used preferably. These mutations can increase the temperature sensitivity of the P protein.

Temperature-sensitive mutations which may be contained in the vector of the present invention are specifically described in WO 2012/029770, WO 2010/008054, and WO 2003/025570. Preferably, F-gene-deficient or -deleted Sendai virus vectors encoding a mutant P protein in which at least at the three positions of D at position 433, R at position 434, and K at position 437 are substituted to other amino acids. In addition, a mutant L protein in which at least the L at position 1558 is substituted (preferably a mutant L protein in which at least the L at position 1361 is also substituted to another amino acid); and F-gene-deficient or -deleted Sendai virus vectors whose cytotoxicity is similar to or lower than those mentioned above and/or whose temperature sensitivity is similar to or higher than those mentioned above are used preferably in the present invention. In addition to the above-mentioned viral protein, each of the viral proteins may have mutations on other amino acids (for example, on ten or less, five or less, four or less, three or less, two or less, or one amino acid). Since vectors comprising the above-mentioned mutations show a high temperature sensitivity.

The genomic RNA contained in the vector of the present invention may encode all of the envelope protein genes or may not encode a part or the whole of the envelope protein genes. The envelope protein genes to be encoded in the genomic RNA (M gene, F gene, and HN gene) may be a wild type or may be introduced with temperature-sensitive mutations. The temperature-sensitive mutations of the envelope proteins are specifically described in WO 2012/029770, WO 2010/008054, and WO 2003/025570.

By expressing a desired exogenous envelope protein in a virus-producing cell when producing the virus vector, a virus vector containing this protein can be produced. Such proteins are not particularly limited and desired proteins, such as adhesion factors, ligands, and receptors that confer an ability to infect to mammalian cells are used. Specific examples may include the G protein of vesicular stomatitis virus (VSV) (VSV-G). The VSV-G protein may be derived from any VSV strain, and for example, VSV-G protein derived from the Indiana serotype strain (J. Virology 39: 519-528 (1981)) can be used, but it is not limited thereto. The virus vectors of the present invention can include arbitrary combinations of other virus-derived envelope proteins.

Temperature sensitivity in the present invention means that the activity is significantly reduced at the standard temperature for cell culture (for example, 37 to 38° C.) when compared to that at a low temperature (for example, 30 to 36° C.). More preferably, the temperature sensitivity means that the activity is significantly reduced at 37° C. when compared to that at 35° C. For example, in the case of an expression vector, a temperature-sensitive vector indicates that the expression amount thereof at the standard temperature for cell culture (for example, 37 to 38° C.) is significantly lower than the expression amount at a low temperature (for example, 37 to 38° C.). For example, a growth rate or gene expression level of the temperature-sensitive vector, for example, at 37° C. is, for example, ⅔ or less, preferably ½ or less, more preferably ⅓ or less, more preferably ⅕ or less, more preferably 1/10, and more preferably 1/20 or less when compared to that at 35° C. Moreover, the growth rate or gene expression level of the temperature-sensitive vector at 37° C. is, for example, ½ or less, more preferably ⅓ or less, more preferably ⅕ or less, more preferably 1/10 or less, and more preferably 1/20 when compared to that of a vector having a wild type protein. For example, TS 7 (Y942H/L1361C/L1558I mutations in the L protein), TS 12 (D433A/R434A/K437A mutations in the P protein). TS 13 (D433A/R434A/K437A mutations in the P protein and L1558I mutation in the L protein), TS 14 (D433A/R434A/K437A mutations in the P protein and L1361C in the L protein), and TS 15 (D433A/R434A/K437A mutations in the P protein and L1361C/L1558I mutations in the L protein) mutations and such in Sendai virus specifically described in WO 2012/029770 and WO 2010/008054 are preferable temperature-sensitive mutations.

Specific vectors may be, for example, an F gene-deleted Sendai virus vector in which the M protein has G69E, T116A, and A183S mutations; the HN protein has A262T, G264R, and K461G mutations; the P protein has L511F mutation; and the L protein has N1197S and K1795E mutations (for example, Z strain); and vectors produced by further introducing a TS 7, TS 12, TS 13, TS 14, or TS 15 mutation into this vector are more preferred. Specifically, examples include SeV18+/TSΔF (WO 2010/008054 and WO 2003/025570) and SeV(PM)/TSΔF, and vectors which are modified so as to add a degron to the P protein in the vectors produced by further introducing a TS 7, TS 12, TS 13, TS 14, or TS 15 mutation into these vectors, but are not limited thereto.

"TSΔF" means carrying G69E, T116A, and A183S mutations in the M protein, A262T, G264R, and K461G mutations in the HN protein, L511F mutation in the P protein, and N1197S and K1795E mutations in the L protein, and deletion of the F gene.

The degron in the present invention refers to a polypeptide that destabilizes a protein by addition to the protein, and is well known by a person skilled in the art. Examples of the degron include a sequence that is stabilized by the binding to a small molecule, a sequence that is destabilized by the binding to a small molecule, and a sequence that is destabilized regardless of whether a small molecule is present. Specific examples include FKBP12-derived DD-tag (US 2009/0215169) that is known as mTOR protein, dihydrofolate reductase (DHFR)-derived DDG-tag (US 2012/0178168), TetR mutant (WO 2007/032555), plant-derived auxin-inducible degron (AID) system (WO 2010/125620), PEST sequence that is known as an auxilytic sequence (WO 99/54348), CL1 (WO 2004/025264), calpain-derived sequence (JP 2009-136154 A), and NDS (JP 2011-101639 A). FKBP12 is known as mammalian target of rapamycin (mTOR), is stabilized by the binding to a low molecule such as rapamycin or shield1, is destabilized by removal thereof, and is degraded by proteasome. DHFR is stabilized by trimethoprim, and TetR mutant is stabilized by doxycycline. The PEST sequence is a sequence rich in Pro, Glu, Ser, and Thr, and for example, the PEST sequence can be destabilized by adding 422-461 at the C terminus side of mouse ornithine decarboxylase (mODC). The PEST sequence regulates the half-life of protein, and a desired half-life reducing sequence can be used (Rechsteiner M, et al., Trends Biochem. Sci. 21, 267-271, 1996). The both ends of the PEST sequence are surrounded, for example, by basic amino acids (H, K, or R), and the PEST sequence is a sequence which includes (i) P, (ii) D and E, or (iii) S and E and binds to ubiquitinating enzyme E3, and can be identified, for example, by GENETYX™ Ver. 9 (GENETYX CORPORATION). As a sequence capable of obtaining the similar effect to the PEST, CL1, a calpain partial sequence, NDS, and the like are exemplified. An AID sequence is destabilized by binding TIR1 and auxin (IAA) that are ubiquitin ligase of plants.

In the present invention, these degrons can be added to the P protein and specific examples of preferred degrons include mTOR degron, DHFR degron, TetR degron, PEST, and AID. Incidentally, natural sequences and those derived therefrom are included in these degrons. Examples of particularly preferred degrons include mTOR degron, DHFR degron, TetR degron, and PEST, among these, degrons other than AID sequence are preferred, and specifically, FKBP12 degron (DD), DHFR degron (DDG), TetR degron, and mODC PEST are preferred. In PEST, d2 derived from natural sequence and d1 or d4 that is a modification thereof are known (WO 99/54348), but all of these are also included in PEST and can be used in the present invention (see Examples).

Hereinbelow, preferred examples of the degron sequences are specifically described. mODC PEST sequence (WO 99/54348)

d2tag: mODC422-461: 422-461 at the C terminus side of ACCESSION: P00860 (SEQ ID NO: 89) (DNA: SEQ ID NO: 101)

d4tag: mODC422-461 (T436A) (SEQ ID NO: 90)

d1tag: mODC422-461 (E428A/E430A/E431A) (SEQ ID NO: 91)

Furthermore, other mutants described in WO 99/54348 may be used. Specifically, preferred examples of PEST sequences may include $MODC_{376-461}$, $MODC_{376-456}$, $MODC_{422-461}$ (SEQ ID NO: 89) described in WO 99/54348 and mutations of P426A/P427A, P438A, E428A/E430A, E431A, E444A, S440A, S445A, T436A, D433A/D434A, D448A, and combinations thereof that are mutation sequences with respect to $MODC_{422-461}$. Furthermore, polypeptides, which include amino acid sequences in which one or plural amino acids are substituted, deleted, and/or added in these amino acid sequences and have the activity of destabilizing proteins, may be used. Particularly preferred sequences are $MODC_{422-461}$ (SEQ ID NO: 89) and mutant mODC422-461 (T436A) (SEQ ID NO: 90) thereof. Moreover, P438A, S440A, and the like can also be used favorably in the present invention.

DD-tag sequence (US 2012/0178168)

DD-tag: FKBP (L106P): mutant of ACCESSION: NP_000792 (F37V/L107P) (SEQ ID NO: 93) (DNA: SEQ ID NO: 102)

Furthermore, another mutant described in US 2012/0178168 may be used. Incidentally, in US 2012/0178168, the mutant is described as L106P without counting the Met at the N terminus, and this mutation is located at the same position as L107P of NP_000792.

Specific examples include 2-108 of ACCESSION: NP_000792 ($FKBP_{2-108}$) (SEQ ID NO: 92), and a mutant thereof, and examples of the mutant include F36V, F15S, V24A, H25R, E60G, L106P, D100G, M66T, R71G, D100N, E102G, K105I (all representing the position when the second amino acid is regarded as "1" without counting the Met at the N terminus), and mutations of combinations thereof. Moreover, polypeptides, which include amino acid sequences in which one or plural amino acids are substituted, deleted, and/or added in these amino acid sequences and have the activity of destabilizing proteins, may be used.

DDG-tag sequence (US 2012/0178168)

DDG-tag: mutant (R12L/G67S/Y100I) (SEQ ID NO: 95) of DHFR (H12L/Y100I):

ACCESSION: B7MAH1 [UniParc] (SEQ ID NO: 94) (DNA: SEQ ID NO: 42)

Furthermore, another mutant described in US 2012/0178168 may be used. Specific examples include an amino acid sequence of DFHR protein (ACCESSION: B7MAH1, SEQ ID NO: 94), and a mutant thereof, and examples of the mutant include N18T/A19V, F103L, Y100I, G121V, H12Y, Y100I, H12L/Y100I, R98H/F103S, M42T/H114R, I61F/T68S, and mutations of combinations thereof. Moreover, polypeptides, which include amino acid sequences in which one or plural amino acids are substituted, deleted, and/or added in these amino acid sequences and have the activity of destabilizing proteins, may be used. Incidentally, the first amino acid Met may be omitted.

TetR-tag sequence (WO 2007/032555)

TetR-tag: mutant (R28Q/D95N/L101S/G102D) (SEQ ID NO: 97) of TetR (R28Q/D95N/L101S/G102D): ACCESSION: NP_941292 (SEQ ID NO: 96) (DNA: SEQ ID NO: 80)

Furthermore, another mutant described in WO 2007/032555 may be used. Specific examples include an amino acid sequence of TetR protein (ACCESSION: NP_941292, SEQ ID NO: 96), and a mutant thereof, and examples of the mutant include D95N, L101S, G102D, and mutations of combinations thereof. Moreover, a mutation of R28Q may be included. Further, polypeptides, which include amino acid sequences in which one or plural amino acids are substituted, deleted, and/or added in these amino acid sequences and have the activity of destabilizing proteins, may be used. Incidentally, the first amino acid Met may be omitted.

The nucleic acid encoding the degron can be appropriately produced by DNA synthesis. Furthermore, the natural degron sequence can be separated by using DNA encoding the aforementioned degron sequence (for example, SEQ ID NO: 101, 102, 42, 80, or the like) or a complementary sequence thereof as a probe and performing a hybridization method under stringent conditions. The stringent hybridization conditions can be appropriately selected by a person skilled in the art. For example, pre-hybridization is carried out at 42° C. overnight in a hybridization solution containing 25% formamide, in the case of stricter conditions, containing 50% formamide, 4×SSC, 50 mM HEPES at pH 7.0, 10×Denhardt's solution, and 20 μg/ml denatured salmon sperm DNA, and then hybridization is carried out at 42° C. overnight. Thereafter, washing can be carried out in a washing solution and temperature condition of about "1×SSC, 0.1% SDS, 37° C.", as more stricter condition, about "0.5×SSC, 0.1% SDS, 42° C.", further stricter condition, about "0.5×SSC, 0.1% SDS, 42° C.", further stricter condition, about "0.2×SSC, 0.1% SDS, 65° C." or "0.1×SSC, 0.1% SDS, 65° C." Polynucleotide isolated by such a hybridization technique or polypeptide encoded by the polynucleotide has typically high homology with polynucleotide as a probe or polypeptide encoded by the polynucleotide in each of nucleotide sequence and amino acid sequence. The high homology indicates sequence identity of at least 70% or higher, further preferably 80% or higher, further preferably 90% or higher, further preferably at least 95% or higher, and further preferably at least 97% or higher (for example, 98% or higher or 996 or higher). The sequence identity can be determined, for example, by algorithm BLAST (Proc. Natl. Acad. Sci. USA 87: 2264-2268, 1990, Proc. Natl. Acad. Sci. USA 90: 5873-5877, 1993) by Karlin and Altschul. In the case of analyzing the sequence by BLAST (Altschul et al. J. Mol. Biol. 215: 403-410, 1990) developed based on that algorithm, default parameters of each program are used. The specific techniques of these analysis methods are known (www.ncbi.nlm.nih.gov.). In the case of modifying the amino acid sequence, the amino acid to be modified is preferably one to several amino acids, and more preferably 1 to 10, 1 to 8, 1 to 5, 1 to 4, 1 to 3, or 1 to 2.

The degron can be appropriately added to a desired position of the P protein, and for example, can be added to the N terminus or C terminus of the P protein. When the degron is added to the N terminus of the P protein and expression of the C protein encoded in the nucleic acid in the coding region of the P protein is inhibited, the C protein may be separately expressed from the vector. When fragments of the P protein are used as the P protein instead of the whole length of the P protein and the fragments do not include the coding region of the C protein, the degron can be added to any position of the N terminus and the C terminus. In the present invention, the degron is preferably added to the C terminus side of the P protein. The modified P protein added with the degron can be produced by known methods. Specifically, a sequence encoding a degron may be inserted into a sequence of a viral genome encoding the P protein while ensuring the reading frame is consistent.

Incidentally, as described above, fragments can be appropriately used without using the whole length of the P protein. Only a part of the C terminus is essential as the P protein, and other regions are not essential in expression of the virus vector. Specifically, the P protein may be fragments holding the binding site to the L protein and the binding site to N protein:RNA. Examples of the binding site to the L protein include amino acid sequences shown in SEQ ID NOS: 411 and 445, and examples of the binding site to N protein:RNA include amino acid sequences shown in SEQ ID NOS: 479 to 568 of the SeV P protein (for example, accession numbers AAB06197.1, P04859.1, P14252.1, AAB06291.1, AAX07439.1, BAM62828.1, BAM62834.1, P04860.1, BAM62840.1, BAD74220.1, P14251.1, BAM62844.1, BAM62842.1, BAM62842.1, BAF73480.1, BAD74226.1, BAF73486.1, Q9DUE2.1, BAC79134.1, NP_056873.1, ABB00297.1, and the like). More specifically, for example, fragments including amino acid sequences of 320 to 568 of the SeV P protein can be suitably used as the functional P protein in the present invention. When the deleted P protein is used, the size of the vector can be reduced and it can be expected to be less influenced by the immune reaction of the host.

When the P protein in which the coding region of the C protein is deleted is used, as described above, the C protein may be appropriately expressed separately. Herein, the C protein includes C', C, Y1, and Y2 proteins (Irie T. et al., PLoS One. (2010) 5: e10719). For expressing the C protein, the coding sequence of the C protein may be appropriately inserted into the vector. There is no particular limitation on insertion position, and the coding sequence of the C protein can be inserted immediately before the P protein (3' side of the coding sequence of the P protein in the genome) or immediately after the P protein (5' side of the coding sequence of the P protein in the genome). Upon the insertion, the E-I-S sequence may be appropriately added.

In the present invention, the vector in which a degron is added to the P protein, particularly, the vector in which a degron is added to the temperature-sensitive P protein specifically has D433A/R434A/K437A mutations in the P protein (WO 2012/029770 and WO 2010/008054), the degron is DD-tag, DDG-tag, TetR-tag, or mODC of the PEST sequence, or a mutant thereof having a different degradation speed (WO 99/54348). More preferably, the vector has L1361C/L1558I mutations in the L protein as the temperature-sensitive mutation.

The low-temperature culturing in the present invention refers to culturing at a temperature lower than 36.5° C. The low-temperature culturing refers to culturing at a low temperature of preferably below 36.4° C., more preferably 36.3° C., 36.2° C., 36.1° C., 36° C., 35.9° C., 35.8° C., 35.7° C., 35.6° C., 35.5° C., 35.4° C., 35.3° C., 35.2° C., or 35.1° C., and more preferably lower than 35° C. The lower limit is, for example, 30° C., preferably 31° C., and more preferably 32° C., 33° C., or 34° C. Further, about 37° C. in the present invention refers to specifically, 36.5 to 37.5° C., preferably 36.6 to 37.4° C., and more preferably 36.7° C. to 37.3° C.

After the vector of the present invention is introduced to express a target gene, the vector can be appropriately removed in accordance with the property of the degron. For example, in the case of using a ligand controllable degron such as DD, DDG, or TetR mutant, removal of the vector can be enhanced by removing or adding a ligand such as Shield-1. Further, in the case of a degron which exhibits the function without a ligand, such as mODC, removal of the vector can be enhanced by continuing the culture of the cells into which the vector is introduced. The culturing period from start of removal until completion of removal may be appropriately determined, and when the vector of the present invention is used, the vector is removed, for example, within four weeks, three weeks, two weeks, or on week, for example, within 20 days, 15 days, ten days, five days, or three days. The culturing period is, for example, three days to three weeks or is five days to 20 days or five days to two weeks. The removal of the virus can be confirmed by the fact that the level of removal is reduced to the same level as that of the virus non-transferred cell (or 1/100 or less, preferably 1/500 or less, 1/1000 or less, or 1/5000 as compared to the maximum value after the introduction of the virus) by detection of the reporter gene or detection of the virus using the antibody or PCR.

In the present invention, enhancing of removal of the vector in which a degron is added to the temperature-sensitive P protein can be carried out, for example, at 35° C. to 39° C. Enhancing of removal can be carried out preferably at 36° C. to 38.5° C. and more preferably at about 37° C. Enhancing of removal of the vector in the present invention means that under such conditions removal of the vector is significantly enhanced as compared to the vector not added with a degron.

Production of the negative-strand RNA virus vector of the present invention may be carried out using known methods. As specific procedures, typically, the negative-strand RNA virus vector can be produced by the steps of (a) transcribing a cDNA encoding the negative-strand RNA virus genomic RNA (minus strand) or a complementary strand thereof (plus strand) in a cell that expresses viral proteins (NP, P, and L) necessary for virus particle formation, and (b) collecting the produced virus. Viral proteins necessary for particle formation may be expressed from the transcribed viral genomic RNA, or may be provided from sources other than genomic RNA. For example, they can be provided by introducing expression plasmids encoding the NP, P, and L proteins into cells. When viral genes necessary for particle formation are lacking in the genomic RNA, those viral genes can be separately expressed in virus-producing cells to complement particle formation. To express the viral proteins or the RNA genome in cells, vectors having a DNA encoding such proteins or genomic RNA linked downstream of a suitable promoter that functions in a host cell is introduced into the host cell. The transcribed genomic RNA is replicated in the presence of viral proteins, and virion is formed. When a defective type of virus lacking genes such as those of the envelope proteins is produced, the missing protein, other viral proteins that can complement the function of these proteins, or such can be expressed in the virus-producing cells. In the present invention, vectors in which at least F gene is deleted can be suitably used.

The genomic RNA included in the vector of the present invention is, for example, genomic RNA in which the degron sequence is added to the P gene, and the RNP of the present invention can be produced by transcribing the genomic RNA (positive strand or negative strand) in the presence of the NP, P, and L proteins. At this time, by expressing the P protein not added with a degron (for example, wild type P protein), it is possible to prevent negative influence on production of the virus by the P protein which is added with a degron and encoded in the genomic RNA. The formation of RNP can be carried out, for example, by BHK-21 or LLC-MK2 cells. The supply of the NP, P, and L proteins can be carried out by various methods as long as the NP, P, and L proteins are not supplied by the virus vector. For example, the supply of the NP, P, and L proteins can be carried out by introducing expression vector encoding each gene as described above into cells (see Examples). Regarding each gene, NP, P, and L genes may be integrated into chromosome of the host cell. The NP, P, and L genes expressed for forming RNP are not necessary to be completely identical to NP, P, and L genes encoded in the genome of the vector. That is, amino acid sequences of proteins encoded by these genes may not be identical to amino acid sequences of proteins encoded by RNP genome, and the amino acid sequences may be introduced with mutation or may be substituted by homologous genes of other viruses as long as they are joined to genomic RNA and have the transcribing and replicating activity of the genome in the cells.

In the case of the envelope protein gene-deficient vectors, if envelope proteins such as F, HN, and/or M proteins are expressed in the cells when the vectors are reconstituted in the cells, those proteins are integrated into the virus vectors, and thus virus vectors maintaining infectiousness can be produced. When the cells are infected with such vectors once, proteins can be expressed from the genomic RNA by RNP in the cells, but the vectors have the P protein added with the temperature-sensitive mutations and the degron sequence. Thus, removal of the vectors is enhanced by an increase in temperature and destabilization of the degron. Such vectors are significantly useful in modification of the cells particularly by carrying transcription factors.

The present invention is a method for producing the vector of the present invention, and provides the method including a step of expressing a nucleic acid encoding genomic RNA of the vector, or a complementary strand thereof, under the presence of NP, P, and L proteins, each of which does not have an added degron. That is, the present invention is a method for producing the vector of the present invention, and provides the method including a step of expressing a nucleic acid encoding genomic RNA of the vector, or a complementary strand thereof, under the presence of NP, P, and L proteins, and the NP, P, and L proteins are NP, P, and L proteins, each of which does not have an added degron. The virus vector produced in this way contains P protein not added with a degron and is a virus vector encoding P protein added with a degron.

For example, production of the negative-strand RNA virus of the present invention can be carried out by expressing the viral genome encoding the P protein modified to attach a degron by using the following known methods (WO 97/16539; WO 97/16538; WO 00/70055; WO 00/70070; WO 01/18223; WO 03/025570; WO 2005/071092; WO 2006/137517; WO 2007/083644; WO 2008/007581; Hasan, M. K. et al., J. Gen. Virol. 78: 2813-2820, 1997, Kato, A. et al., 1997, EMBO J. 16: 578-587 and Yu, D. et al., 1997, Genes Cells 2: 457-466; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol. 71: 1265-1271; Bridgen, A. and Elliott, R. M., 1996, Proc. Natl. Acad. Sci.

USA 93: 15400-15404; Tokusumi, T et al. Virus Res. 2002: 86; 33-38, and Li, H.-O. et al., J. Virol. 2000: 74; 6564-6569). Further, regarding methods for proliferation of viruses and methods for producing recombinant viruses, see also "Uirusu-gaku Jikken-gaku Kakuron (Detailed Virology Experiments)", second revised edition (National Institute of Infectious Diseases Students Institute edition, Maruzen, 1982).

The activity of the P protein of the vector of the present invention is decreased in addition to the above description, and thus preferably, the vector is produced by using P expressing cells. In the case of vectors in which the F gene is deficient, production of the vector may be carried out by using cells expressing P protein and F protein (PF expressing cell) (see Examples in the present invention).

The vector of the present invention can carry a desired gene. There is no particular limitation on genes to be carried, and a desired exogenous gene (a gene that a vector does not have originally) can be carried. There is no particular limitation on the number of exogenous genes to be carried, and one, two or more exogenous genes can be carried. When the exogenous gene encodes a protein, a degron can be appropriately added to the protein. By adding a degron different from the degron added to the P protein of the vector of the present invention, expression of the protein encoded by the exogenous gene can be controlled independently from removal of the vector (Examples 26 and 27). For example, a degron whose expression can be controlled by temperature can be added to the P protein and a degron whose expression can be controlled by a compound or the like can be added to the protein encoded by the exogenous gene. Specifically, for example, a PEST sequence or a dd-tag can be added to the P protein and a dd-tag that can be controlled by shield1 or the like or a ddg-tag that can be controlled by trimethoprim or the like can be added to the protein encoded by the exogenous gene. Furthermore, for example, when two exogenous genes are carried, adding a degron, which is different from each other, to the protein encoded by each exogenous gene, it is possible to control expression of each expression of these two exogenous proteins independently from the vector. Specifically, for example, by adding a PEST sequence or a dd-tag to the P protein and respectively adding a dd-tag and a ddg-tag to proteins encoded by two exogenous genes, it is possible to independently control expression of the two exogenous genes. The present invention also relates to a method for controlling expression of an exogenous gene using these vectors, independently from the timing of removal of vectors. Such vectors are particularly useful in expression regulation when expressing proteins such as transcription factors, cell differentiation regulatory factors and the like.

In the vector of the present invention, generally, exogenous genes can be inserted immediately before (3' side of the genome of) or immediately after (5' side of the genome of) any of the viral genes (for example, NP, P, M, F, HN, or L). The exogenous genes may be appropriately sandwiched between the Sendai Virus S (Start) sequence and the E (End) sequence. The S sequence is a signal sequence that initiates transcription, and the E sequence terminates the transcription. The region between the S sequence and the E sequence becomes a single transcription unit. A sequence that serves as a spacer (intervening sequence) can be appropriately inserted between the E sequence of a certain gene and the S sequence of the next gene.

While a desired S sequence of the negative-strand RNA virus may be used as the S sequence, for example, in the case of Sendai virus, 3'-UCCCWVUUWC-5' (W=A or U; V=A, C, or G) sequence (SEQ ID NO: 1) can be used favorably. In particular, 3'-UCCCAGUUUC-5' (SEQ ID NO: 2), 3'-UCCCACUUAC-5' (SEQ ID NO: 3), and 3'-UCCCACUUUC-5' (SEQ ID NO: 4) are preferred. When these sequences are presented as DNA sequences encoding the plus strand, they are 5'-AGGGTCAAAG-3' (SEQ ID NO: 5), 5'-AGGGTGAATG-3' (SEQ ID NO: 6), and 5'-AGGGTGAAAG-3' (SEQ ID NO: 7), respectively. The E sequence of the negative-strand RNA virus vector is preferably, for example in the case of the Sendai virus, 3'-AUUCUUUUU-5' (the plus strand-encoding DNA is 5'-TAAGAAAAA-3'). The I sequence may be, for example, any three bases, and specifically, 3'-GAA-5' (5'-CTT-3' in the plus strand DNA) may be used.

The vector of the present invention can be applied to production of pluripotent stem cells by carrying genes encoding reprogramming factors such as transcription factors, and removal of the vector at this time can be enhanced. For example, in WO 2012/029770 and WO 2010/008054, cMYC is carried on a temperature-sensitive TS15 vector, and when pluripotent stem cells are produced by using KLF4, OCT4, SOX2, and cMYC, removal of the vector can be enhanced by carrying cMYC on the vector of the present invention and using this in place of the cMYC vector above. As transcription factors used in production of pluripotent stem cells, molecules other than the above-described molecules, such as L-MYC, Glis1, Lin28, and NANOG, may be used. A transcription factor gene carried on the vector can be appropriately modified. For example, by introducing one or more, preferably two or more, three or more, four or more, or all five mutations selected from the group consisting of a378g, t1122c, t1125c, a1191g, and a1194g into wild type c-MYC, it is possible to express genes to a high level from the vector (for example, SEQ ID NO: 45 described in WO 2010/008054).

In the present invention, "pluripotent stem cells" refer to stem cells produced from the inner cell mass of an embryo of an animal in the blastocyst stage or cells having phenotypes similar to those cells. Specifically, pluripotent stem cells induced in the present invention are cells that express alkaline phosphatase which is an indicator of ES-like cells. Herein, the ES-like cells refer to pluripotent stem cells that have properties and/or forms similar to ES cells. Furthermore, preferably, when pluripotent stem cells are cultured, they form flat colonies containing cells with a higher proportion of nucleus volume than cytoplasm. Culturing may be carried out suitably with a feeder. Moreover, while cultured cells such as MEF stop proliferating in a few weeks, pluripotent stem cells can be passaged for a long period of time, and this can be confirmed based on their proliferative character that is not lost even when they are passaged, for example, 15 times or more, preferably 20 times or more, 25 times or more, 30 times or more, 35 times or more, or 40 times or more every three days. Furthermore, pluripotent stem cells preferably express endogenous NANOG. Furthermore, pluripotent stem cells preferably express TERT, and show telomerase activity (activity to synthesize telomeric repeat sequences). Moreover, pluripotent stem cells preferably have the capability to differentiate into three germ layers (the endoderm, mesoderm, and ectoderm) (for example, confirmable during teratoma formation and/or embroid body formation). More preferably, pluripotent stem cells produce germline chimera when they are transplanted into blastocysts. Pluripotent stem cells capable of germline transmission are called germline-competent pluripotent stem cells. Confirmation of these phenotypes can be carried out by known methods (WO 2007/69666; Ichisaka T et al., Nature 448 (7151):313-7, 2007). Furthermore, differentiation inducing factor genes may be carried on the vectors of the present invention, and introduced into undifferentiated cells, stem cells, or the like so that desired cells or tissues can also be differentiated.

Cells produced by inducing the vectors of the present invention are useful for causing differentiation into a variety of tissues and cells, and can be used in desired examinations, research, diagnosis, tests, treatments, and such. For example, induced stem cells are expected to be utilized in stem cell therapy. For example, reprogramming is induced by using somatic cells collected from patients, and then somatic stem cells and other somatic cells that are obtained by induction of differentiation can be transplanted into patients. Methods for inducing cellular differentiation are not particularly limited, and for example, differentiation can be induced by retinoic acid treatment, treatment with a variety of growth factors/cytokines, and treatment with hormones. Furthermore, the obtained cells can be used for detecting effects of the desired pharmaceutical agents and compounds, and this enables screening of pharmaceutical agents and compounds to be carried out. The present invention can be used for medical uses and for non-medical uses, and is useful in medical and non-medical embodiments. For example, the present invention can be used for therapeutic, surgical, and/or diagnostic, or non-therapeutic, non-surgical, and/or non-diagnostic purposes.

Cells into which vectors are introduced are not particularly limited, but may be differentiated somatic cells and may be somatic stem cells or germ stem cells such as hematopoietic stem cells, neural stem cells, mesenchymal stem cells, hepatic stem cells, and skin epidermis stem cells. Furthermore, cells may be derived, for example, from cells of embryos, fetuses, newborns, children, adults, or the aged. Moreover, the origin of the animals is not particularly limited, and includes mammals such as humans and non-human primates (monkeys and such), rodents such as mice and rats, and non-rodents such as bovine, pigs, and goats.

When the vectors of the present invention are introduced into cells and cultured at 37° C., as compared with the gene expression amount from the vectors or the vector amount after three days from introduction of the vectors into cells, the gene expression amount from each vector or the vector amount is reduced, for example, to 1/5 or less, preferably 1/8 or less, preferably 1/10 or less, 1/20 or less, 1/30 or less, or 1/50 or less after culturing for one week, and is reduced, for example, to 1/10 or less, preferably 1/20 or less, preferably 1/30 or less, 1/50 or less, 1/100 or less, 1/150 or less, 1/200 or less, 1/300 or less, 1/500 or less, 1/1000 or less, or detection limit or less after culturing for two weeks. Furthermore, when the vectors of the present invention are introduced into cells and then cultured at 37° C., the expression amount of the reporter protein from the vectors is significantly lower than the expression amount of the reporter protein in the case of not adding a degron to the P protein but adding a degron to the reporter protein itself in culturing for one week or two weeks, specifically for example, 2/3 or less, preferably 1/2 or less, preferably 1/3 or less, 1/5 or less, 1/8 or less, preferably 1/10 or less, 1/20 or less, 1/30 or less, or 1/50 or less. Examples of the cells include HeLa cells (ATCC CCL-2), BHK-21 cells (JCRB9020), CHO cells, 293 cells, and BJ cells (ATCC CRL-2522), and measurement is carried out preferably in HeLa cells.

Furthermore, the present invention relates to a method that includes a step of co-infecting other negative-strand RNA virus vector with the negative-strand RNA virus vector of the present invention for enhancing removal of the other negative-strand RNA virus vector. The other negative-strand RNA virus vector is not particularly limited as long as it is the same kind of negative-strand RNA virus vector as the negative-strand RNA virus vector of the present invention and may be a wild type negative-strand RNA virus vector or a gene-deficient or gene-modified negative-strand RNA virus vector. In the present invention, it is found that the negative-strand RNA virus vector of the present invention not only enhances removal of the negative-strand RNA virus vector itself in infected cells but also enhances removal of the other co-existing negative-strand RNA virus vector. That is, the vector of the present invention is not only useful for enhancing removal of the vector of the present invention itself and genes carried on the vector but also useful for enhancing removal of other co-existing negative-strand RNA virus or negative-strand RNA virus vector and genes carried on the vector.

That is, the present invention provides a method for enhancing removal of other negative-strand RNA virus or other negative-strand RNA virus vector, the method including a step of co-infecting other negative-strand RNA virus or other negative-strand RNA virus vector with the negative-strand RNA virus vector of the present invention. Regarding co-infecting, it is not necessary to infect viruses or vectors simultaneously but it is sufficient to provide a period of time when viruses or vectors co-exist in cells. First, cells are infected with other negative-strand RNA virus or other negative-strand RNA virus vector, and then cells can be infected with the vector of the present invention when the other negative-strand RNA virus or other negative-strand RNA virus vector need to be removed.

Further, the present invention provides a removal enhancer, which contains the negative-strand RNA virus vector of the present invention, of negative-strand RNA virus or negative-strand RNA virus vector. Furthermore, the present invention provides a removal enhancer, which contains the negative-strand RNA virus vector of the present invention, of genes introduced by negative-strand RNA virus vector. Moreover, the present invention provides a use of the negative-strand RNA virus vector of the present invention in enhancing of removal of negative-strand RNA virus vector and/or genes introduced by negative-strand RNA virus vector. Further, the present invention provides a use of the negative-strand RNA virus vector of the present invention in producing of a removal enhancer of negative-strand RNA virus vector and/or genes introduced by negative-strand RNA virus vector. Using the vector of the present invention, it is possible to control expression of the carried gene of another negative-strand RNA virus vector as well as to control expression of the carried gene of the vector of the present invention. For example, when a degron, which is a small-molecule ligand and can control destabilization, such as Shield-1 is used, by co-infecting the vector of the present invention, when a ligand is added or deleted at a desired timing, it is possible to remove a negative-strand RNA virus vector not having a degron as well as the vector of the present invention.

EXAMPLES

Hereinbelow, the present invention is specifically described with reference to the Examples; however, it is not to be construed as being limited thereto. All documents and other references cited herein are incorporated as part of this description.

<Production of Sendai Virus Vector Used in Present Invention Carrying Exogenous Gene>

The methods for producing Sendai virus vectors carrying an exogenous gene and used in the present invention are shown below. Incidentally, in the present invention, "18+" refers to inserting GOI before the NP gene, "(PM)" refers to inserting GOI between the P gene and the M gene, "(F)" refers to inserting GOI in the place of the F gene (between the M gene and the HN gene), and "(HNL)" refers to inserting GOI between the HN gene and the L gene. Furthermore, in the present invention, "TS" refers to having G69E, T116A, and A183S mutations in the M protein, A262T, G264R, and K461G mutations in the HN protein, L511F mutation in the P protein, and N1197S and K1795E mutations in the L protein, and "ΔF" shows that the F gene is deleted. For example, an F gene-deleted Sendai virus vector having TS mutation in which GOI is inserted before the NP gene is described as SeV18+/TSΔF. Unless otherwise specified, the restriction enzyme used in the insertion of GOI is NotI. Furthermore, TS12 is a Sendai virus vector containing D433A, R434A, and K437A mutations in the P protein in addition to the above-described TS mutation, and TS15 is a Sendai virus vector containing L1361C and L1558I mutations in the L protein in addition to the above-described TS12 mutation. However, these are exemplary, and the present invention is not limited to these examples.

1) Construction of pEB-P Vector

The P gene derived from pSeV (TDK) (WO 2005/071092) was cloned into pEBMulti-Hyg (Wako Pure Chemical Industries, Ltd.) digested with NotI to obtain pEB-P.

2) Construction of SeV(F)/TSΔF Vector Carrying DD-Azami Green (ddAG)

PCR reaction was carried out using Azami Green (AG) from phmAG (Amalgaam Co., Ltd.) as template; and primers XhoI-AG-F (5'-ATATCTCGAGCTATGGTGAGCGTGATCA-3') (SEQ ID NO: 8) and EcoRI-AG-R (5'-ATATGAATTCGCGGCCGCGATGAACT-3') (SEQ ID NO: 9). This PCR product was digested with XhoI and EcoRI (overnight at 37° C.) and the obtained DNA fragment was cloned into pPTuner (Clontech Laboratories, Inc.) containing DD-tag sequence (SEQ ID NO: 93) to obtain pPTuner-ddAG PCR reaction was carried out using this pPTuner-ddAG as template; and primers NotI-ddAG-F (5'-ATATGCGGCCGCACCATGGGAGTGCAGGTGGA-3') (SEQ ID NO: 10) and EcoRI-AG-R (SEQ ID NO: 9). This PCR product was digested with NotI and the obtained DNA fragment was cloned into the NotI site of pSeV(F)/TSΔF to obtain pSeV(F)ddAG/TSΔF. The Sendai virus produced from the transcriptional product of the pSeV(F)ddAG/TSΔF vector is referred to as SeV(F)ddAG/TSΔF.

3) Construction of SeV(HNL)/TSΔF Vector Carrying DD-Azami Green (ddAG)

The ddAG was cloned into the NotI site of SeV(HNL)/TSΔF to obtain pSeV(HNL)ddAG/TSΔF. The Sendai virus produced from the transcriptional product of the pSeV(HNL)ddAG/TSΔF vector is referred to as SeV(HNL)ddAG/TSΔF.

4) Construction of pSeV18+/PLmutTSΔF

PCR reaction was carried out using pSeV18+/TSΔF as template; and primers BamHI-P-F (5'-ATATGGATCCAGTTCACGCGGCCGCA-3') (SEQ ID NO: 11) and XhoI-P-R (5'-ATATCTCGAGTCGGTGCAGGCCTTTA-3') (SEQ ID NO: 12). This PCR product was digested with BamHI and XhoI and the obtained DNA fragment was cloned into pBlueScript II-SK+ (Stratagene) to obtain pBS-P. By carrying out PCR reaction using this pBS-P as template; and primers Pmut-F1 (5'-GGATCATACGGCGCGCCAAGGTACTTG-3') (SEQ ID NO: 13), Pmut-R1 (5'-CAAGTACCTTGGCGCGCCGTATGATCC-3') (SEQ ID NO: 14), Pmut-F2 (5'-CAACTAGATCCTGCAGGAGGCATCCTAC-3') (SEQ ID NO: 15), and Pmut-R2 (5'-GTAGGATGCCTCCTGCAGGATCTAGTG-3') (SEQ ID NO: 16), an AscI site was introduced into the upstream of the P gene and an SbfI site was introduced into the downstream of the P gene to obtain pBS-Pmut. Then, PCR reaction was carried out using pSeV18+TSΔF as template; and primers BamHI-L-F (5'-ATATGGATCCGTACGATCGCAGTCCACCAT-3') (SEQ ID NO: 17) and XhoI-L-R (5'-ATATCTCGAGCAGCTAGCTCAACTGA-3') (SEQ ID NO: 18). This PCR product was digested with BamHI and XhoI and the obtained DNA fragment was cloned into pBlueScript II-SK+ to obtain pBS-L. By carrying out PCR reaction using this pBS-L as template; and primers Lmut-F (5'-GTGAATGGGAGGCCGGCCATAGGTC-3') (SEQ ID NO: 19) and Lmut-R (5'-GACCTATGGCCGGCCTCCCATTCAC-3') (SEQ ID NO: 20), an FseI site was introduced into the upstream of the L gene to obtain pBS-Lmut. Then, pSeV18+/TSΔF was digested with SalI and PvuI, pBS-Lmut was digested with PvuI and KpnI, and these were cloned into pBlueScript II-SK+ to obtain pBS-LmutSeV. Then, pBS-LmutSeV was digested with NheI and SalI and cloned into pSeV18+/TSΔF to obtain pSeV18+/LmutTSΔF. Then, pSeV18+/LmutTSΔF was digested with NotI, NheI, and StuI, pBS-Pmut was digested with NotI and StuI, and these DNA fragments were joined to each other to obtain pSeV18+/PLmutTSΔF.

5) Construction of SeV18+/LddTSΔF Vector Carrying BFP

PCR reaction was carried out using pSeV18+/TSΔF as template; and primers XhoI-L-F (5'-ATATCTCGAGTCACTAAAGAGT-3') (SEQ ID NO: 21) and HindIII-L-R (5'-ATATAAGCTTCGAGCTGTCATATGGCT-3') (SEQ ID NO: 22). This PCR product was digested with XhoI and HindIII to obtain XhoI-L fragment. Then, PCR reaction was carried out using pPTuner as template; and primers HindIII-dd-F (5'-ATATAAGCTTCACCGGTCGGGAGTGCAGGTGGAAA-3') (SEQ ID NO: 23) and KpnI-dd-R1 (5'-ATATGGTACCCTATTCCAGT TCTAGAAGCTCCACATCGA-3') (SEQ ID NO: 24). This PCR product was digested with HindIII and KpnI to obtain dd-KpnI fragment. The XhoI-L fragment and dd-KpnI fragment were cloned into pBlueScript II-SK+ to obtain pBS-XhoI-Ldd. Then, PCR reaction was carried out using pBS-XhoI-Ldd as template; and primers XhoI-L-F (SEQ ID NO: 21) and KpnI-Ldd-R2 (5'-ATATGGTACCGCCTATTCCAGTTCTAG-3') (SEQ ID NO: 25). This PCR product was digested with XhoI and KpnI and cloned into pSeV18+/PLmutTSΔF to obtain pSeV18+/LddTSΔF. Then, pCI-BFP-EIS obtained by cloning TagBFP (Evrogen) into pCI-neo (Promega Corporation) was digested with NotI and cloned into pSeV18+/LddTSΔF to obtain pSeV18+BFP/LddTSΔF. The Sendai virus produced from the transcriptional product of the pSeV18+BFP/LddTSΔF vector is referred to as SeV18+BFP/LddTSΔF.

6) Construction of SeV18+/PddTSΔF Vector Carrying BFP

PCR reaction was carried out using pSeV18+/LddTSΔF as template; and primers AscI-Pdd-F (5'-ATATGGCGCGCCAAGGTACTTGATCCG-3') (SEQ ID NO: 26) and HindIII-Pdd-R (5'-ATATAAGCTTGTTGGTCAGTGACTC-3') (SEQ ID NO: 27). This PCR product was digested with AscI and HindIII to obtain AscI-P fragment. Then, PCR reaction was carried out using pSeV18+/LddTSΔF as template; and primers HindIII-dd-F (SEQ ID NO: 23) and SbfI-Pdd-R (5'-ATATCCTGCAGGATCTATTCCAGTTCTAG-3') (SEQ ID NO: 28). This PCR product was digested with HindIII and SbfI to obtain Pdd-SbfI fragment. The AscI-P fragment and Pdd-SbfI fragment were cloned into pSeV18+/PLmutTSΔF to obtain pSeV18+/PddTSΔF. Then, pCI-BFP-EIS was digested with NotI and cloned into pSeV18+/PddTSΔF to obtain pSeV18+BFP/PddTSΔF. The Sendai virus produced from the transcriptional product of the pSeV18+BFP/PddTSΔF vector is referred to as SeV18+BFP/PddTSΔF.

7) Construction of SeV(HNL)/TSΔF Vectors Carrying d1GFP, d2GFP, and d4GFP d1GFP, d2GFP, and d4GFP each having different half-life were produced by adding the PEST sequence of mODC (WO 99/54348), which is known to regulate half-life, to GFP. mODC422-461 that is the PEST sequence of mODC is referred to as d2 (SEQ ID NO: 89), one obtained by adding E428A/E430A/E431A mutation for shortening half-life to mODC422-461 is referred to as d1 (SEQ ID NO: 91), and one obtained by adding T436A mutation for shortening half-life to mODC422-461 is referred to as d4 (SEQ ID NO: 90).

PCR reaction was carried out using pSeV18+GFP/TS7ΔF (WO 2010/008054; WO 2012/029770) as template; and primers NotI-GFP-F (5'-ATTGCGGCCGCCAAGGTT-CACTTATGGTGAGCAAGGGCGAGGAGCTGTT-CACCG-3') (SEQ ID NO: 29), NotI-GFP-R1 (5'-CCGGCGGGAAGCCATGGCTA AGCTTCTTGTACAGCTCGTCC-3') (SEQ ID NO: 30). NotI-GFP-R2 (5'-GGCGCTCTCCTGGGCACAAGA-CATGGGCAGCGTGCCATCATCCTGGGCGGC-CACGGCCGGCGGGAAGCCA-3') (SEQ ID NO: 31), NotI-GFP-R3 (5'-CTACACATT-GATCCTAGCAGAAGCACAGGCT GCAGGGTGGCGGTC-CATGGCGCTCTCCTGGGCACAAGAC-3') (SEQ ID NO: 32), and NotI-GFP-R4 (5'-ATATGCGGCCGCGAT-GAACTTTCACCCTAAGTTTTTCTTACTACGGCTA-CACATGATCCTAGCAGAAGC-3') (SEQ ID NO: 33). This PCR product was digested with NotI and the obtained DNA fragment was cloned into pSeV(HNL)/TSΔF to obtain pSeV(HNL)d1GFP/TSΔF. Then, PCR reaction was carried out using pSeV18+GFP/TS7ΔF as template; and primers NotI-GFP-F (SEQ ID NO: 29). NotI-GFP-R1 (SEQ ID NO: 30), NotI-GFP-R3 (SEQ ID NO: 32), NotI-GFP-R4 (SEQ ID NO: 33), and NotI-GFP-R5 (5'-GGCGCTCTCCTGGGCACAAGA-CATGGGCAGCGTGCCATCATCCTGCTCCTC-CACCTCCGGCGGGAAGCCA-3') (SEQ ID NO: 34). This PCR product was digested with NotI and the obtained DNA fragment was cloned into pSeV(HNL)-TSΔF to obtain pSeV(HNL)d2GFP/TSΔF. Then, PCR reaction was carried out using pSeV18+GFP/TS7ΔF as template; and primers NotI-GFP-F (SEQ ID NO: 29), NotI-GFP-R1 (SEQ ID NO: 30), NotI-GFP-R3 (SEQ ID NO: 32), NotI-GFP-R4 (SEQ ID NO: 33), and NotI-GFP-R6 (5'-GGCGCTCTCCTGGGCACAAGA-CATGGGCAGGGCGCCATCATCCTGCTCCTC-CACCTCCGGCGGGAAGCCA-3') (SEQ ID NO: 35). This PCR product was digested with NotI and the obtained DNA fragment was cloned into pSeV(HNL)TSΔF to obtain pSeV(HNL)d4GFP/TSΔF. The Sendai viruses produced from the transcriptional products of the pSeV(HNL)d1GFP/TSΔF, pSeV(HNL)d2GFP/TSΔF, and pSeV(HNL)d4GFP/TSΔF vectors are referred to as SeV(HNL)d1GFP/TSΔF, SeV(HNL)d2GFP/TSΔF, and SeV(HNL)d4GFP/TSΔF, respectively.

8) Construction of SeV(HNL)/TSΔF Vectors Carrying d1AG, d2AG, and d4AG

PCR reaction was carried out using pSeV18+AG/TSΔF as template; and primers AG-F1 (5'-ACAAGAGAAAAAA-CATGTATGG-3') (SEQ ID NO: 36) and AG-R1 (5'-CCATGGCTAAGCTTCTTGGCCTGGCTGGGC-3') (SEQ ID NO: 37) to obtain AG fragments. Then, PCR reaction was carried out using pSeV(HNL)d1GFP/TSΔF as template; and primers AG-F2 (5'-GCCCAGCCAGGCCAAGAAGCT-TAGCCATGG-3') (SEQ ID NO: 38) and AG-R2 (5'-GA-TAACAGCACCTCCTCCCGACT-3') (SEQ ID NO: 39) to obtain d1 fragment. Then, PCR reaction was carried out using pSeV(HNL)d2GFP/TSΔF as template; and primers AG-F2 (SEQ ID NO: 38) and AG-R2 (SEQ ID NO: 39) to obtain d2 fragments. Then, PCR reaction was carried out using pSeV(HNL)d4GFP/TSΔF as template; and primers AG-FE (SEQ ID NO: 38) and AG-R2 (SEQ ID NO: 39) to obtain d4 fragment. Then, PCR reaction was carried out using the AG fragment and d1, d2, and d4 fragments as template; and primers AG-F1 (SEQ ID NO: 36) and AG-R2 (SEQ ID NO: 39). These PCR products were digested with NotI and the obtained DNA fragments were cloned into pSeV(HNL)/TSΔF to obtain pSeV(HNL)d1AG/TSΔF, pSeV(HNL)d2AG/TSΔF, and pSeV(HNL)d4AG/TSΔF. The Sendai viruses produced from the transcriptional products of the pSeV(HNL)d1AG/TSΔF, pSeV(HNL)d2AG/TSΔF, and pSeV(HNL)d4AG/TSΔF vectors are referred to as SeV(HNL)d1AG/TSΔF, SeV(HNL)d2AG/TSΔF, and SeV(HNL)d4AG/TSΔF, respectively.

9) Construction of SeV(HNL)/TSΔF Vectors Carrying d1ddAG, d2ddAG, and d4ddAG

PCR reaction was carried out using pSeV(F)ddAG/TSΔF as template; and primers ddAG-F1 (5'-ATCAGA-GACCTGCGACAA-3') (SEQ ID NO: 40) and AG-R1 (SEQ ID NO: 37) to obtain ddAG-F fragment. Then, PCR reaction was carried out using pSeV(HNL)d1GFP/TSΔF as template; and primers AG-F2 (SEQ ID NO: 38) and ddAG-R (5'-CTGGATAGAGTATGTCAGAAGGGTTTTG-3') (SEQ ID NO: 41) to obtain d1ddAG-R fragment. Then, PCR reaction was carried out using the ddAG-F fragment and the d1ddAG-R fragment as template; and primers AG-F1 (SEQ ID NO: 36) and ddAG-R (SEQ ID NO: 41) to obtain d1ddAG fragment. Then, PCR reaction was carried out using pSeV(HNL)d2GFP/TSΔF as template; and primers AG-F2 (SEQ ID NO: 38) and ddAG-R (SEQ ID NO: 41) to obtain d2ddAG-R fragment. Then, PCR reaction was carried out using the ddAG-F fragments and the d2ddAG-R fragments as template; and primers AG-F1 (SEQ ID NO: 36) and ddAG-R (SEQ ID NO: 41) to obtain d2ddAG fragment. Then, PCR reaction was carried out using pSeV(HNL)d4GFP/TSΔF as template; and primers AG-F2 (SEQ ID NO: 38) and ddAG-R (SEQ ID NO: 41) to obtain d2ddAG-R fragment. Then, PCR reaction was carried out using the ddAG-F fragment and the d2ddAG-R fragment as template; and primers AG-F1 (SEQ ID NO: 36) and ddAG-R (SEQ ID NO: 41) to obtain d4ddAG fragment. Then, these PCR products were digested with NotI and the obtained DNA fragment were cloned into pSeV(HNL)/TSΔF to obtain pSeV(HNL)d1ddAG/TSΔF, pSeV(HNL)d2ddAGTSΔF, and pSeV(HNL)d4ddAG/TSΔF. The Sendai viruses produced from the transcriptional products of the pSeV(HNL)d1ddAG/TSΔF, pSeV(HNL)d2ddAG/TSΔF, and pSeV(HNL)d4ddAG/TSΔF vectors are referred to as SeV(HNL)d1ddAG/TSΔF, SeV(HNL)d2ddAG/TSΔF, and SeV(HNL)d4ddAG/TSΔF, respectively.

10) Construction of SeV(HNL)d2ddgRFP/TSΔF Vector

PCR reaction was carried out using ecDHFR sequence (SEQ ID NO: 42) (Biomatik) (the sequence described in US 2012/0178168 was codon-modified) synthesized by synthesis of an artificial gene as template; and primers ddg-F (5'-ATTAACCCTCACTAAAGGGA-3') (SEQ ID NO: 43) and ddg-R (5'-CCTTAGACACTCGCCGCTCCAGAATCTC-3') (SEQ ID NO: 44) to obtain ddg fragment containing DDG-tag (SEQ ID NO: 95). Then, PCR reaction was carried out using SeV18+RFP/TSΔF carrying TagRFP (Evrogen) as template; and primers RFP-F (5'-GAGCGGCGAGTGTCTAAGGGCGAAGAGCTG-3') (SEQ ID NO: 45) and RFP-R (5'-GGCTAAGCTATTAAGTTTGTGCCCCAG-3') (SEQ ID NO: 46) to obtain RFP fragment. Then, PCR reaction was carried out using pSeV(HNL)d2AG/TSΔF as template; and primers d2-F (5'-CAAACTTAATAAGCTTAGCCATGGCTTCCC-3') (SEQ ID NO: 47) and ddAG-R (SEQ ID NO: 41) to obtain d2RFP fragment. Then, PCR reaction was carried out using the ddg fragment, the RFP fragment, and the d2RFP fragment as template; and primers ddg-F (SEQ ID NO: 43) and ddAG-R (SEQ ID NO: 41). This PCR product was digested with NotI and the obtained DNA fragment was cloned into pSeV(HNL)/TSΔF to obtain pSeV(HNL)d2ddgRFP/TSΔF. The Sendai virus produced from the transcriptional product of the pSeV(HNL)d2ddgRFP/TSΔF is referred to as SeV(HNL)d2ddgRFP/TSΔF.

11) Construction of SeV(PM)d2ddgRFP(HNL)d2ddAG/TS12ΔF Vector pSeV(HNL)d2ddgRFP/TSΔF was digested with NotI and d2ddgRFP was cloned into SeV(PM)/TS12ΔF to obtain SeV(PM)d2ddgRFP/TS12ΔF. Then, pSeV(HNL)d2ddAG/TSΔF was digested with NotI and d2ddAG was cloned into pSeV(HNL)/TS12ΔF to obtain pSeV(HNL)d2ddAG/TS12ΔF. Then, SeV(PM)d2ddgRFP/TS12ΔF and pSeV(HNL)d2ddAG/TS12ΔF were digested with PacI and NheI and joined to each other to obtain pSeV(PM)d2ddgRFP(HNL)d2ddAG/TS12ΔF. The Sendai virus produced from the transcriptional product of the pSeV(PM)d2ddgRFP(HNL)d2ddAG/TS12ΔF is referred to as SeV(PM)d2ddgRFP(HNL)d2ddAG/TS12ΔF.

12) Construction of SeV18+TIR1(HNL)AGaid/TSΔF Vector pBMH-TIR1 carrying TIR1 sequence (SEQ ID NO: 48) (Biomatik) (the sequence described in WO 2010/125620 was codon-modified) synthesized by synthesis of an artificial gene was digested with NotI and cloned into pSeV18+/TSΔF to obtain pSeV18+TIR1/TSΔF. Then, PCR reaction was carried out using pSeV(HNL)AG/TSΔF as template; and primers AGaid-F (5'-TAACTGACTAGCAGGCTTGTCG-3') (SEQ ID NO: 49), AGaid-R1 (5'-CACTGGTGGCCATCCCACAACTTGACTACCTCCACCTCCGCTCCACCTCCACCACTCTTGGCCTGACTC-3') (SEQ ID NO: 50), AGaid-R2 (5'-CTTTCACCCTAAGTTTTTCTTACTACGGCTACTTTCTATATGATCTCACTGGTGGCCATCCC-3') (SEQ ID NO: 51), and AGaid-R3 (5'-CTGCGGCCGCGATGAACTTTCACCCTAAGTTTTTC-3') (SEQ ID NO: 52) to amplify fragments including AID sequence (244-282 of accession number AY117183 (SEQ ID NO: 98), and 82-94 of accession number AAM51258 (SEQ ID NO: 99)). Incidentally, the above-described primers are designed such that silent mutations (g264a and ccgg276-279taga; SEQ ID NO: 100) are introduced into natural AID sequence (244-282 of accession number AY117183). This PCR product was digested with NotI and the obtained DNA fragment was cloned into pSeV(HNL)/TSΔF to obtain pSeV(HNL)AGaid/TSΔF. Then, pSeV18+TIR1/TSΔF and pSeV(HNL)AGaid/TSΔF were digested with SphI and AatI and joined to each other to obtain pSeV18+TIR1(HNL)AGaid/TSΔF. The Sendai virus produced from the transcriptional product of the pSeV18+TIR1(HNL)AGaid/TSΔF is referred to as SeV18+TIR1(HNL)AGaid/TSΔF.

13) Construction of SeV18+TIR1(HNL)d2AG/PaidTSΔF Vector

PCR reaction was carried out using pSeV18+/PLmutTSΔF as template; and primers Paid-F (5'-CTGCAACCCATGGAGATGAAGG-3') (SEQ ID NO: 53), Paid-R1 (5'-CTGGTGGCCATCCCACAACTTGACTACCTCCACCTCCGCTTCCACCTCCACCACTGTTGGTCAGTGACTC-3') (SEQ ID NO: 54), and Paid-R2 (5'-TATACCTGCAGGATCTACTTTCTATATGATCTCACTGGTGGCCATCCCAC-3') (SEQ ID NO: 55). This PCR product was digested with AscI and SbfI and the obtained DNA fragment was cloned into pSeV18+/PLmutTSΔF to obtain pSeV18+/PaidTSΔF. Then, pBMH-TIR1 was digested with NotI and cloned into pSeV18+/PaidTSΔF to obtain pSeV18+TIR1/PaidTSΔF. Then, pSeV18+TIR1/PaidTSΔF was digested with StuI and AatII, pSeV(HNL)d2AG/TSΔF was digested with StuI, NheI, and AatII, pSeV(HNL)d2AG/TSΔF was digested with NheI and AatII, and these were joined to each other to obtain pSeV18+TIR1(HNL)d2AG/PaidTSΔF. The Sendai virus produced from the transcriptional product of the pSeV18+TIR1(HNL)d2AG/PaidTSΔF is referred to as SeV18+TIR1(HNL)d2AG/PaidTSΔF.

14) Construction of SeV18+TIR1(HNL)d2AG/LaidTSΔF Vector

PCR reaction was carried out using pSeV18+/TSΔF as template; and primers Laid-F (5'-ATCACTGCTAGATCTGTGCTGC-3') (SEQ ID NO: 56), Laid-R1 (5'-GGTGGCCATCCCACAACTTGACTACCTCCACCTCCGCTTCCACCTCCACCACTCGAGCTGTCATATGGC-3') (SEQ ID NO: 57), Laid-R2 (5'-CTAATTACTACTTCTATATGATCTCACTGGTGGCCATCCCACAACTTGACTAC-3') (SEQ ID NO: 58), and Laid-R3 (5'-TATAGGTACCGCGGAGCTTCGATCGTTCTGCACGATAGGGACTAATTACTACTTTCTATATGATC-3') (SEQ ID NO: 59). This PCR product was digested with NheI and KpnI and the obtained DNA fragment was cloned into pSeV18+TIR1/TSΔF to obtain pSeV18+TIR1/LaidTSΔF. Then, pSeV18+TIR1/LaidTSΔF was digested with SphI, NheI, and SalI, pSeV(HNL)d2AG/TSΔF was digested with SphI, NheI, and XhoI, and these were joined to each other to obtain pSeV18+TIR1(HNL)d2AG/LaidTSΔF. The Sendai virus produced from the transcriptional product of the pSeV18+TIR1(HNL)d2AG/LaidTSΔF is referred to as SeV18+TIR1(HNL)d2AG/LaidTSΔF.

15) Construction of SeV18+/PddTS15ΔF Vector

PCR reaction was carried out using pSeV18+/TS15ΔF as template; and primers AscI-Pdd-F (SEQ ID NO: 26) and HindIII-Pdd-R (SEQ ID NO: 27). The fragment was digested with AscI and HindIII to obtain AscI-Pts15 fragment. Then, the AscI-Pts15 fragment and the SbfI-Pdd fragment were cloned into pSeV18+/PLmutTSΔF to obtain pSeV18+/Pts15ddTSΔF. Then, the pSeV18+/Pts15ddTSΔF and pSeV18+/TS15ΔF were digested with KpnI and NheI and these were joined to each other to obtain pSeV18+/PddTS15ΔF. BFP and GFP were carried on the pSeV18+/PddTS15ΔF to obtain pSeV18+BFP/PddTS15ΔF and pSeV18+GFP/PddTS15ΔF. The Sendai viruses produced from the transcriptional products of the pSeV18+BFP/

PddTS15ΔF and the pSeV18+GFP/PddTS15ΔF are referred to as SeV18+BFP/PddTS15ΔF and SeV18+GFP/PddTS15ΔF respectively.

16) Construction of SeV18+/ddPTS15ΔF Vector

PCR reaction was carried out using pSeV18+TS15ΔF as template; and primers ddPts15-F1 (5'-ATTCTCGAGGATCAAGATGCCTTCATTC-3') (SEQ ID NO: 60) and ddPts15-R2 (5'-AATAAGCTTCTAGTTGGTCAGTGACTC-3') (SEQ ID NO: 61). The fragment was digested with XhoI and HindIII and cloned into pPTuner to obtain pPTuner-Pts15. Then, PCR reaction was carried out using pSeV18+TS15ΔF as template; and primers ddPts15-F2 (5'-ATTGGCGCGCCAAGGTACTTGATCCGTAG-3') (SEQ ID NO: 62) and ddPts15-R2 (5'-CACCTGCACTCCCATGCGGTAAGTGTAGC-3') (SEQ ID NO: 63) to obtain AscI-ddPts15. Then, PCR reaction was carried out using pPTuner-Pts15 as template; and primers ddPts15-F3 (5'-GCTACACTTACCGCATGGGAGTGCAGGTG-3') (SEQ ID NO: 64) and ddPts15-R3 (5'-AATCCTGCAGGTGATGATCTAGTTGGTCAGTGACTC-3') (SEQ ID NO: 65) to obtain ddPts15-SbfI. Then, PCR reaction was carried out using AscI-ddPts15 and ddPts15-SbfI as template; and primers ddPts15-F2 (SEQ ID NO: 62) and ddPts15-R3 (SEQ ID NO: 65) to obtain AscI-ddPts15-SbfI. Then, the AscI-ddPts15-SbfI was digested with AscI and SbfI and cloned into pSeV18+/PLmutTSΔF to obtain pSeV18+/ddPts15TSΔF. Then, the pSeV18+/ddPts15TSΔF and the pSeV18+/TS15ΔF were digested with KpnI and NheI and these were joined to each other to obtain pSeV18+/ddPTS15ΔF. BFP and GFP were carried on the pSeV18+/ddPTS15ΔF to obtain pSeV18+BFP/ddPTS15ΔF and pSeV18+GFP/ddPTS15ΔF. The Sendai viruses produced from the transcriptional products of the pSeV18+BFP/ddPTS15ΔF and the pSeV18+GFP/ddPTS15ΔF are referred to as SeV18+BFP/ddPTS15ΔF and SeV18+GFP/ddPTS15ΔF, respectively.

17) Construction of pPdd-Halo and pddP-Halo Vectors

PCR reaction was carried out using pRL-TK (Promega Corporation) as template; and primers HSVp-F (5'-ATATAGATCTAAATGAGTCTTCGGACCTCG-3') (SEQ ID NO: 66) and HSVp-R (5'-ATATGCTAGCTTAAGCGGGTCGCTGCAG-3') (SEQ ID NO: 67) to obtain an HSV promoter. This HSV promoter was digested with BglII and NheI and cloned into pCI-neo (Promega Corporation) to obtain pHSV-neo. Then, PCR reaction was carried out using pFN21A HaloTag (Promega Corporation) as template; and primers HaloTag-F1 (5'-TCTGTACTTTCAGAGCGATAACGATGGATCCGAAATCGGTACTGGC-3') (SEQ ID NO: 68), HaloTag-R (5'-GCGGCCGCTTAACCGGAAATCTCGAGCGTC-3') (SEQ ID NO: 69), and HaloTag-F2 (5'-GCTAGCATATGGTACCCCAACCACTGAGGATCTGTACTTCAGAGCG-3') (SEQ ID NO: 70), and then cloned into pGEM-T Easy (Promega Corporation) to obtain pGEM-HaloTag. Then, PCR reaction was carried out using pSeV18+/ddPTS15ΔF as template; and primers ddP-Halo-F (5'-ATATGCTAGCATGGGAGTGCAGGTGGAAAC-3') (SEQ ID NO: 71) and ddP-Halo-R (5'-ATATGGTACCCTAGTTGGTCAGTGACTC-3') (SEQ ID NO: 72). The obtained PCR product was digested with NheI and KpnI and cloned into pGEM-HaloTag to obtain pGEM-ddP-Halo. The obtained pGEM-ddP-Halo was digested with NheI and NotI and cloned into pHSV-neo to obtain pHSV-ddP-Halo. Then, PCR reaction was carried out using pSeV18+/PddTS15ΔF as template; and primers Pdd-Halo-F (5'-ATATGCTAGCATGGATCAAGATGCCTTC-3') (SEQ ID NO: 73) and KpnI-dd-R1 (SEQ ID NO: 24). The obtained PCR product was digested with NheI and KpnI and cloned into pGEM-HaloTag to obtain pGEM-Pdd-Halo. The obtained pGEM-Pdd-Halo was digested with NheI and NotI and cloned into pHSV-neo to obtain pHSV-Pdd-Halo.

18) Construction of SeV18+/PddTS15ΔF Vectors Carrying d1AG, d2AG, and d4AG

PCR reaction was carried out using pSeV18+AG/PLmutTSΔF having AG carried at 18+ position of pSeV18+/PLmutTSΔF as template; and primers AG-F1 (SEQ ID NO: 36) and AG-R1 (SEQ ID NO: 37) to obtain dAG fragment. Then, PCR reaction was carried out using pSeV(HNL)d1GFP/TSdF as template; and primers AG-F2 (SEQ ID NO: 38) and dAG-R2 (5'-CAAAACCCTTCTGACATACTCTATCCAG-3') (SEQ ID NO: 74) to obtain d1 fragment. Then, PCR reaction was carried out using the dAG fragment and the d1 fragment as template; and primers AG-F1 (SEQ ID NO: 36) and dAG-R2 (SEQ ID NO: 74) and the obtained d1AG fragment was cloned into pBlueScript II-SK+ to obtain pBS-d1AG. Then, PCR reaction was carried out using pSeV(HNL)d2GFP/TSdF as template; and primers AG-F2 (SEQ ID NO: 38) and dAG-R2 (SEQ ID NO: 74) to obtain d2 fragment. Then, PCR reaction was carried out using the dAG fragment and the d2 fragment as template; and primers AG-F1 (SEQ ID NO: 36) and dAG-R2 (SEQ ID NO: 74) and the obtained d2AG fragment was cloned into pBlueScript II-SK+ to obtain pBS-d2AG. Then, PCR reaction was carried out using pSeV(HNL)d4GFP/TSdF as template; and primers AG-F2 (SEQ ID NO: 38) and dAG-R2 (SEQ ID NO: 74) to obtain d4 fragment. Then, PCR reaction was carried out using the dAG fragment and the d4 fragment as template; and primers AG-F1 (SEQ ID NO: 36) and dAG-R2 (SEQ ID NO: 74) and the obtained d4AG fragment was cloned into pBlueScript II-SK+ to obtain pBS-d4AG. Then, the pBS-d1AG, the pBS-d2AG, and the pBS-d4AG were digested with NotI and cloned into pSeV18+/PddTS15ΔF to obtain pSeV18+d1AG/PddTS15ΔF, pSeV18+d2AG/PddTS15ΔF, and pSeV18+d4AG/PddTS15ΔF. The Sendai viruses produced from the transcriptional products of the pSeV18+d1AG/PddTS15ΔF, the pSeV18+d2AG/PddTS15ΔF, and the pSeV18+d4AG/PddTS15ΔF are referred to as SeV18+d1AG/PddTS15ΔF, SeV18+d2AG/PddTS15ΔF, and SeV18+d4AG/PddTS15ΔF, respectively.

19) Construction of SeV18+d2AG/d2PTS15ΔF and SeV18+d2AG/d4PTS15ΔF Vectors

PCR reaction was carried out using pSeV18+d2AG/TS15ΔF as template; and primers Paid-F (SEQ ID NO: 53), dP-R1 (5'-CCATGGCTAAGCTTGTTGGTCAGTGACTC-3') (SEQ ID NO: 75), dP-R2 (5'-CCGGCGGGAAGCCATGGCTAAGCTTGTTGG-3') (SEQ ID NO: 76), NotI-GFP-R5 (SEQ ID NO: 34), NotI-GFP-R3 (SEQ ID NO: 32), and dP-R5 (5'-ATTCCTGCAGGATCTACACATTGATCCTAGCAGAAGC-3') (SEQ ID NO: 77) to obtain d2P fragment. Then, the d2P fragment and pSeV18+d2AG/PddTS15ΔF were digested with AscI and SbfI and joined to each other to obtain pSeV18+d2AG/d2PTS15ΔF. Then, PCR reaction was carried out using pSeV18+d2AG/TS15ΔF as template; and primers Paid-F (SEQ ID NO: 53), dP-R1 (SEQ ID NO: 75), dP-R2 (SEQ ID NO: 76), NotI-GFP-R6 (SEQ ID NO: 35), NotI-GFP-R3 (SEQ ID NO: 32), and dP-R5 (SEQ ID NO: 77) to obtain d4P fragment. Then, the d4P fragment and pSeV18+d2AG/PddTS15ΔF were digested with AscI and SbfI and joined to each other to obtain pSeV18+d2AG/d4PTS15ΔF. The Sendai viruses produced from the transcriptional products of the pSeV18+d2AG/d2PTS15ΔF and the pSeV18+d2AG/d4PTS15ΔF are referred to as SeV18+d2AG/d2PTS15ΔF and SeV18+d2AG/d4PTS15ΔF, respectively.

20) Construction of SeV18+d2AG/PddgTS15ΔF Vector

PCR reaction was carried out using pSeV(HNL)d2ddgRFP/TS/dF as template; and primers HindIII-ddg-F (5'-AATAAGCTTCACCGGTCGATCAGTCTGATTGCGG-3') (SEQ ID NO: 78) and SbfI-ddg-R (5'-CTTCCTGCAGGATTATCTATCGCCGCTCCAGAATCTC-3') (SEQ ID NO: 79) and the obtained PCR product was digested with HindII and SbfI to obtain HindIII-ddg-SbfI fragment. Then, pSeV18+d2AG/PaidTS15ΔF into which Paid was inserted instead of Pdd of pSeV18+d2AG/PddTS15ΔF was digested with AscI. SbfI, and HindIII to obtain AscI-P-HindIII fragment. Then, the HindIII-ddg-SbfI fragment and the AscI-P-HindIII fragment were joined to the pSeV18+d2AG/PaidTS15ΔF digested with AscI and SbfI to obtain pSeV18+d2AG/PddgTS15ΔF. The Sendai virus produced from the transcriptional product of the pSeV18+d2AG/PddgTS15ΔF is referred to as SeV18+d2AG/PddgTS15ΔF.

21) Construction of SeV(HNL)d2tetRAG/TSΔF Vector

PCR reaction was carried out using a TetR mutant sequence (SEQ ID NO: 80) (amino acid sequence is SEQ ID NO: 97) (FASMAC) (the sequence described in WO 2007/032555 was codon-modified) synthesized by synthesis of an artificial gene as template; and primers NotI-tetR-F (5'-ATATGCGGCCGCCTTGCCACCATGTCTAGGCTGGACAAG-3') (SEQ ID NO: 81) and tetR-R (5'-CACGCTCACAGACCCACTTTCACATTTAAG-3') (SEQ ID NO: 82) to obtain NotI-tetR fragment. Then, PCR reaction was carried out using pSeV18+d2AG/PddTS15dF as template; and primers d2AG-F (5'-GTGGGTCTGTGAGCGTGATCAAGCCCGAG-3') (SEQ ID NO: 83) and AG-R2 (SEQ ID NO: 39) to obtain td2AG fragment. Then, PCR reaction was carried out using the NotI-tetR fragment and the td2AG fragment as template; and primers NotI-tetR-F (SEQ ID NO: 81) and AG-R2 (SEQ ID NO: 39) to obtain d2tetRAG fragment. Then, the d2tetRAG fragment was cloned into pSeV(HNL)/TSΔF to obtain pSeV(HNL)d2tetRAG/TSΔF. The Sendai virus produced from the transcriptional product of the pSeV(HNL)d2tetRAG/TSΔF is referred to as SeV(HNL)d2tetRAG/TSΔF.

22) Construction of SeV18+/PtetRTS15ΔF Vector Carrying d2AG

PCR reaction was carried out using pSeV18+d2AG/PddTS15dF as template; and primers Paid-F (SEQ ID NO: 53) and dP-R7 (5'-CAGCCTAGAGTTGGTCAGTGACTCTATGTC-3') (SEQ ID NO: 84) to obtain Ptet fragment. Then, PCR reaction was carried out using a TetR mutant sequence (SEQ ID NO: 80) as template; and primers PtetR-F (5'-CTGACCAACTCTAGGCTGGACAAGAGTAAG-3') (SEQ ID NO: 85) and PtetR-R (5'-ATATCCTGCAGGATCTAAGACCCACTTTCACATITAAG-3') (SEQ ID NO: 86) to obtain tetR-SbfI fragment. Then, PCR reaction was carried out using the Ptet fragment and the tetR-SbfI fragment as template; and primers Paid-F (SEQ ID NO: 53) and PtetR-R (SEQ ID NO: 86) to obtain PtetR fragment. Then, the PtetR fragment was cloned into pSeV18+d2AG/TS15ΔF digested with AscI and SbfI to obtain pSeV18+d2AG/PtetRTS15ΔF. The Sendai virus produced from the transcriptional product of the pSeV18+d2AG/PtetRTS15ΔF is referred to as SeV18+d2AG/PtetRTS15ΔF.

23) Construction of SeV18+/TS12ΔF, SeV18+/d2PTS12ΔF, and SeV18+/PddTS12ΔF Vectors Carrying d2AG d2AG was cloned into pSeV18+/TS12ΔF to obtain pSeV18+d2AG/TS12ΔF. Then, pSeV18+/TS12ΔF and pSeV18+d2AG/d2PTS15ΔF were digested with NheI and KpnI and joined to each other to obtain pSeV18+d2AG/d2PTS12ΔF. Then, pSeV18+/TS12ΔF and pSeV18+d2AG/PddTS15ΔF were digested with NheI and KpnI and joined to each other to obtain pSeV18+d2AG/PddTS12ΔF. The Sendai viruses produced from the transcriptional products of the pSeV18+d2AG/TS12ΔF, the pSeV18+d2AG/d2PTS12ΔF, and the pSeV18+d2AG/PddTS12ΔF are referred to as SeV18+d2AG/TS12ΔF, SeV18+d2AG/d2PTS12ΔF, and SeV18+d2AG/PddTS12ΔF.

24) Construction of SeV(HNL)/d2PTS15ΔF, SeV(HNL)/PddTS15ΔF, SeV(HNL)/PddgTS15ΔF, and SeV(HNL)/PtetRTS15ΔF Vectors Carrying cMYC pSeV(HNL)AG/PaidTS15ΔF was digested with AscI and SbfI to obtain pSeV(HNL)AG/TS15ΔF (AscI/SbfI) fragment. Then, pSeV18+d2AG/d2PTS15ΔF, pSeV18+d2AG/PddTS15ΔF, pSeV18+d2AG/PddgTS15ΔF, and pSeV18+d2AG/PtetRTS15ΔF were digested with AscI and SbfI to obtain d2P, Pdd, Pddg, and PtetR fragments. Then, joining of these fragments was carried out to obtain pSeV(HNL)AG/d2PTS15ΔF, pSeV(HNL)AG/PddTS15ΔF, pSeV(HNL)AG/PddgTS15ΔF, and pSeV(HNL)AG/PtetRTS15ΔF. Then, pSeV(PM)KOS(HNL)cMYC/TSΔF was cut with NotI and the obtained cMYC fragment was cloned into pSeV(HNL)AG/d2PTS15ΔF, pSeV(HNL)AG/PddTS15ΔF, pSeV(HNL)AG/PddgTS15ΔF, and pSeV(HNL)AG/PtetRTS15ΔF, which were digested with NotI, to obtain pSeV(HNL)cMYC/d2PTS15ΔF, pSeV(HNL)cMYC/PddTS15ΔF, pSeV(HNL)cMYC/PddgTS15ΔF, and pSeV(HNL)cMYC/PtetRTS15ΔF. The Sendai viruses produced from the transcriptional products of the pSeV(HNL)cMYC/d2PTS15ΔF, the pSeV(HNL)cMYC/PddTS15ΔF, the pSeV(HNL)cMYC/PddgTS15ΔF, and the pSeV(HNL)cMYC/PtetRTS15ΔF are referred to as SeV(HNL)cMYC/d2PTS15ΔF, SeV(HNL)cMYC/PddTS15ΔF, SeV(HNL)cMYC/PddgTS15ΔF, and SeV(HNL)cMYC/PtetRTS15ΔF.

25) Construction of pCAGGS-d144P, pCAGGS-d307P, and pCAGGS-Pct Vectors

PCR reaction was carried out using pSeV18+TSΔF as template; and primers NotI-SeV-Pd144-F (5'-ATATGCGGCCGCACCATGGGATATCCGAGA-3') (SEQ ID NO: 103) and SeV-P-NotI-R (5'-ATATGCGGCCGCCTAGTTGGTCAGTGACTC-3') (SEQ ID NO: 104) to obtain NotI-Pd144 fragment. PCR reaction was carried out using pSeV18+TSΔF as template; and primers NotI-SeV-Pd307-F (5'-ATATGCGGCCGCACCATGGGTCTAGAGACC-3') (SEQ ID NO: 105) and SeV-P-NotI-R (SEQ ID NO: 104) to obtain NotI-Pd307 fragment. PCR reaction was carried out using pSeV18+TSΔF as template; and primers NotI-SeV-Pct-F (5'-ATATGCGGCCGCACCATGGGAGAGAACACA-3') (SEQ ID NO: 106) and SeV-P-NotI-R (SEQ ID NO: 104) to obtain NotI-Pct fragments. The obtained fragments were digested with NotI and cloned into a plasmid having a NotI linker integrated into the EcoRI site of pCAGGS (Gene, vol. 108, pp 193-199, 1991) to obtain pCAGGS-d144P, pCAGGS-d307P, and pCAGGS-Pct.

26) Construction of pEB-SeV-Pdd-Halo, pEB-MeV-Pdd-Halo, pEB-NDV-Pdd-Halo, pEB-PIV2-Pdd-Halo, and pEB-VSV-Pdd-Halo Vectors MeV (AIK-C): the P gene of ACCESSION: AF266286 (SEQ ID NO: 107) (GENEWIZ), NDV (LaSota): the P gene of ACCESSION: AY845400 (SEQ ID NO: 108) (GENEWIZ), PIV2: the P gene of ACCESSION: M37748 (SEQ ID NO: 109) (GENEWIZ), and VSV (Indiana): the P gene of ACCESSION: FJ478454 (SEQ ID NO: 110) (GENEWIZ) each synthesized by synthesis of an artificial gene were digested with NheI and HindIII and cloned into pHSV-Pdd-Halo to obtain pHSV-MeV-Pdd-Halo, pHSV-NDV-Pdd-Halo, pHSV-PIV2-Pdd-Halo, and pHSV-VSV-Pdd-Halo. Then, PCR reaction was carried out using pHSV-Pdd-Halo and plasmid thereof as template; and primers NotI-TKp-F (5'-ATATGCGGCCGCGCTTAAGCTAGCATG-3') (SEQ ID NO: 111) and HaloTag-R (SEQ ID NO: 69), and the obtained PCR product was digested with NotI and cloned into pEBMulti-Hyg to obtain pEB-SeV-Pdd-Halo, pEB-MeV-Pdd-Halo, pEB-NDV-Pdd-Halo, pEB-PIV2-Pdd-Halo, and pEB-VSV-Pdd-Halo.

27) Construction of SeV(PM)ddgOFP(HNL)ddDGFP/d2PTS15ΔF and SeV(PM)ddgOFP(HNL)ddDGFP/PddTS15ΔF Vectors PCR reaction was carried out using YukonOFP (DNA 2.0) as template; and primers NotI-OFP-F (5'-ATATGCGGCCGCTCGCCACCATGT-CACTGTCTAAACAGGTG-3') (SEQ ID NO: 112) and OFP-EIS-NotI-R (5'-ATATGCGGCCGCGAACTTT-CACCCTAAGTTITTCTACT-TACTAGGTTTCCTTGACGTCCACGGTGAAAT-3') (SEQ ID NO: 113), and the obtained PCR product was digested with NotI and cloned into pSeV18+TSΔF to obtain pSeV18+OFP/TSΔF. PCR reaction was carried out using DasherGFP (DNA 2.0) as template; and primers NotI-DGFP-F (5'-ATAGCGGCCGCGA-CATGACTGCCCTGACCG-3') (SEQ ID NO: 114) and DGFP-EIS-NotI-R (5'-TATGCGGCCGCGATGAACTTT-CACCCTAAGTTTTTCTTACTACGGTTACTGA-TAGGTATCGAGATCGAC-3') (SEQ ID NO: 115), and the PCR product was digested with NotI and cloned into pSeV18+TSΔF to obtain pSeV18+DGFP/TSΔF. Then, PCR reaction was carried out using pSeV(HNL)d2ddgRFP/TSΔF as template; and primers AGaid-F (SEQ ID NO: 49) and ddgOFP-R (5'-TTAGACAGT-GATCGCCGCTCCAGAATCTC-3') (SEQ ID NO: 116) to obtain ddgOFP-N fragment. PCR reaction was carried out using pSeV18+OFP/TSΔF as template; and primers ddg-OFP-F (5'-GGAGCGGCGAT-CACTGTCTAAACAGGTGC-3') (SEQ ID NO: 117) and EIS-NotI-2R (5'-CCTGCGGCCGCATGAACTTT-CACCCTAAGTTTTC-3') (SEQ ID NO: 118) to obtain ddgOFP-EIS fragment. PCR reaction was carried out using the ddgOFP-N fragment and the ddgOFP-EIS fragment as template; and primers ddgOFP-F (SEQ ID NO: 117) and EIS-NotI-2R (SEQ ID NO: 118), and the obtained PCR product was digested with NotI and cloned into pSeV(PM)/d2PTS15ΔF to obtain pSeV(PM)ddgOFP/d2PTS15ΔF. Then, PCR reaction was carried out using pSeV18+BFP/PddTS15ΔF as template; and primers NotI-dd-F (5'-ATATGCGGCCGCGCCACCATGGGAGTGCAGGTG-GAAACC-3') (SEQ ID NO: 119) and ddgOFP-R (5'-CGGTCAGGGCAGTTTCCAGTTCTAGAAGC-3') (SEQ ID NO: 120) to obtain ddDGFP-N fragment. PCR reaction was carried out using pSeV18+DGFP/TSΔF as template; and primers ddDGFP-F (5'-TCTAGAACTG-GAAACTGCCCTGACCGAAGG-3') (SEQ ID NO: 121) and AG-R2 (SEQ ID NO: 39) to obtain ddDGFP-EIS fragment. PCR reaction was carried out using the ddDGFP-N fragment and the ddDGFP-EIS fragment as template; and primers ddDGFP-F (SEQ ID NO: 121) and AG-R2 (SEQ ID NO: 39), and the obtained PCR product was digested with NotI and cloned into pSeV(HNL)/d2PTS15ΔF to obtain pSeV(HNL)ddDGFP/d2PTS15ΔF. Then, the pSeV(PM)ddgOFP/d2PTS15ΔF was digested with SalI and AseI, the pSeV(HNL)ddDGFP/d2PTS15ΔF was digested with AseI and NheI, and the pSeV(HNL)ddDGFP/d2PTS15ΔF was digested with Salt NheI, and NotI. The obtained (PM)ddgOFP fragment, (HNL)ddDGFP fragment, and pSeV-SalI-NheI fragment were joined to each other to obtain pSeV(PM)ddgOFP(HNL)ddDGFP/d2PTS15ΔF. Then, the pSeV(PM)ddgOFP(HNL)ddDGFP/d2PTS15ΔF and the SeV18+BFP/PddTS15ΔF were digested with AscI and SbfI and joined to each other to obtain pSeV(PM)ddgOFP(HNL)ddDGFP/PddTS15ΔF. The Sendai viruses produced from the transcriptional products of the pSeV(PM)ddgOFP(HNL)ddDGFP/d2PTS15ΔF and the pSeV(PM)ddgOFP(HNL)ddDGFP/PddTS15ΔF are referred to as SeV(PM)ddgOFP(HNL)ddDGFP/d2PTS15ΔF and SeV(PM)ddgOFP(HNL)ddDGFP/PddTS15ΔF.

28) Construction of SeV18+DGFP/PddΔF Vector

PCR reaction was carried out using pSeV18+ΔF as template; and primers BamHI-P-F (SEQ ID NO: 11) and Pmut-R1 (SEQ ID NO: 14) to obtain BamHI-PmutdF fragment. Then, PCR reaction was carried out using pSeV18+ΔF as template; and primers Pmut-F1 (SEQ ID NO: 13) and Pmut-R2 (SEQ ID NO: 16) to obtain PmutdF fragment. Then, PCR reaction was carried out using pSeV18+ΔF as template; and primers Pmut-F2 (SEQ ID NO: 15) and XhoI-P-R (SEQ ID NO: 12) to obtain PmutdF-XhoI fragment. Then, PCR reaction was carried out using the BamHI-PmutdF fragment, the PmutdF fragment, and the PmutdF-XhoI fragment as template; and primers BamHI-P-F (SEQ ID NO: 11) and XhoI-P-R (SEQ ID NO: 12), and the obtained DNA fragment was cloned into pBlueScript II-SK+ to obtain pBS-PmutdF. Then, the pBS-PmutdF was digested with NotI, StuI, and XhoI to obtain 3878 bp fragment. Then, pSeV18+ΔF was digested with NotI and NheI to obtain 6321 bp fragment. Then, pSeV18+ΔF was digested with NotI, StuI, and NheI to obtain 6161 bp fragment. Then, the 3878 bp fragment, the 6321 bp fragment, and the 6161 bp fragment were joined to each other to obtain pSeV18+/PmutΔF. Then, PCR reaction was carried out using pSeV18+ΔF as template; and primers AscI-Pdd-F (SEQ ID NO: 26) and HindIII-Pdd-R (SEQ ID NO: 27), and the obtained fragment was digested with AscI and HindIII to obtain AscI-PdF-HindIII fragment. Then, PCR reaction was carried out using pSeV18+BFP/PddTSΔF as template; and primers HindIII-dd-F (SEQ ID NO: 23) and SbfI-Pdd-R (SEQ ID NO: 28), and the obtained PCR product was digested with HindIII and SbfI to obtain Pdd-SbfI fragment. The AscI-PdF-HindIII fragment and Pdd-SbfI fragment were cloned into pSeV18+/PmutΔF to obtain pSeV18+/PddΔF. Then, pSeV18+DGFP/TSΔF was digested with NotI and cloned into pSeV18+/PddΔF to obtain pSeV18+DGFP/PddΔF. The Sendai virus produced from the transcriptional product of the pSeV18+DGFP/PddΔF vector is referred to as SeV18+DGFP/PddΔF.

Example 11

HeLa cells were seeded into 12-well plates at $1\times10^5$ cells/well and pEB-P was gene-transferred to the cells using Lipofectamine LTX (Life Technologies), SeV18+GFP/TSΔP (WO 2008/133206) was infected at MOI=10 at 37° C. (day 0), and then observation with a fluorescence microscope was carried out on day 1. As the fluorescence microscope, ECLIPSE TE2000-U (Nikon Corporation) was used. As a result, in the cells to which pEB-P was gene-transferred, green fluorescence was observed by infection of SeV18+GFP/TSΔP; however, in the cells into which pEB-P was not gene-transferred and which were infected only with SeV18+GFP/TSΔP, green fluorescence was not observed (FIG. 1).

Example 2

HeLa cells were seeded into 12-well plates at $1\times10^5$ cells/well. SeV(F)ddAG/TSΔF (ddAG) was infected at MOI=10 at 37° C. (day 0), 1 μM of Shield1 was added thereto on day 1, and after 5 hr. observation with a fluorescence microscope and analysis by FACS were carried out. FACScalibur (BD Biosciences) was used as FACS. As a result, green fluorescence was observed in ddAG infected cells added with Shield and strong fluorescence of ddAG+Shield1 was observed with FACS. It was difficult to determine fluorescence of ddAG not added with Shield1 under the microscope, but in FACS, fluorescence at the base level that is clearly discerned from control cells which were not infected with ddAG was observed (FIG. 2).

Example 3

HeLa cells were infected with SeV(HNL)ddAG/TSΔF (ddAG) at MOI=10 at 37° C. (day 0), 1 μM of Shield1 was added thereto on day 1, and after 5 hr, observation with a fluorescence microscope and analysis by FACS were carried out. As a result, green fluorescence was observed in ddAG infected cells added with Shield1 and strong fluorescence of ddAG+Shield1 was observed with FACS. Fluorescence of ddAG not added with Shield was decreased by carrying the gene at HNL position as compared to SeV(F)ddAG/TSΔF on which the gene was carried at F position, but with FACS, fluorescence at the base level that is clearly discerned from control cells which were not infected with ddAG was observed (FIG. 3).

Example 41

HeLa cells were infected with SeV(HNL)d1GFP/TSΔF (d1GFP), SeV(HNL)d2GFP/TSΔF (d2GFP), SeV(HNL)d4GFP/TSΔF (d4GFP), SeV(HNL)d1AG/TSΔF (d1AG), SeV(HNL)d2AG/TSΔF (d2AG), and SeV(HNL)d4AG/TSΔF (d4AG) at MOI=10 at 37° C. (day 0), and then observation with a fluorescence microscope was carried out on day 2. As a result, a decrease in fluorescence was observed by adding a PEST sequence to the C terminus side of GFP or AG Among d4GFP, d2GFP, and d1GFP, fluorescence of d4GFP was strong and fluorescence of d1GFP was weak (FIG. 4). It was possible to observe d2AG and d4AG under the fluorescence microscope, but it was difficult to determine d1AG under the fluorescence microscope. Thus, in the subsequent tests, d2 and d4 were used.

Example 5

HeLa cells were infected with SeV(HNL)d2ddAG/TSΔF (d2ddAG) and SeV(HNL)d4ddAG/TSΔF (d4ddAG) at MOI=10 at 37° C. (day 0), 1 μM of Shield1 was added thereto on day 3, and analysis by FACS was carried out on day 5. As a result, even when the gene was carried at HNL position of the SeV vector in combination of PEST sequence in addition to DD-tag, regarding fluorescence of AG at the time of not adding Shield1, fluorescence at the base level that is clearly discerned from control cells was observed (FIG. 5).

Example 6

HeLa cells were infected with SeV(PM)d2ddgRFP(HNL)d2ddAG/TS12ΔF (ddgRFP-ddAG) at MOI=10 at 37° C. (day 0), 1 μM of Shield1 or 20 μM of trimethoprim (TMP) was added thereto on day 2, and after 6 hr, observation with a fluorescence microscope was carried out. As a result, green fluorescence was observed in ddgRFP-ddAG infected cells added with Shield1, red fluorescence was observed in ddgRFP-ddAG infected cells added with TMP, and green and red fluorescences were observed in ddgRFP-ddAG infected cells added with Shield1 and TMP. Thus, it was observed that independent control can be performed on the SeV vector (FIG. 6).

Example 7

HeLa cells were infected with SeV(HNL)d2tetRAG/TSΔF (d2tetRAG) at MOI=10 at 35° C. (day 0), 1.5 μg/mL of doxorubicin (DOX) was added thereto on day 1, the cells were then transferred to 37° C., and then observation with a fluorescence microscope was carried out on day 3. As a result, green fluorescence was observed in d2tetRAG infected cells added with DOX (FIG. 7).

Example 8

HeLa cells were infected with SeV18+TIR1(HNL)AGaid/TSΔF (TIR1-AGaid) at MOI=10 at 37° C. (day 0), 500 μM or 2 mM of naphthalene acetic acid (NAA) as Auxin was added thereto on day 3, and after 4 hr and after one day, observation with a fluorescence microscope and a fluorescence plate reader was carried out. Infinite F200 (TECAN) was used as the fluorescence plate reader. As a result, a decrease in fluorescence of the cells infected with TIR1-AGaid was not observed within 4 hr after addition of Auxin, but a decrease in fluorescence to 79.5% (500 μM) was observed after one day (FIG. 8).

[Example 9] PF Expressing Cell

In order to obtain PF expressing cells, the P genes were introduced into LLC-MK2/F cells expressing the F protein (WO 00/70070). pCXN-P4C(−) was gene-transferred to the LLC-MK2/F cells by a calcium phosphate method, and selection by G418 was carried out to obtain LLC-MK2/PF cells expressing the P protein and the F protein (PF expressing cells). The obtained PF expressing cells were infected with SeV18+GFP/TSΔP in which the P genes are deficient, and green fluorescence was observed under a fluorescence microscope, confirming the P protein was functional. Furthermore, expression of the P protein and the F protein was confirmed by the Western blotting method. The PF expressing cells were used at 32° C. in production of the SeV vectors of the present invention in which a degron is added to the P protein.

Example 10

BHK cells were infected with SeV18+BFP/PddTSΔF (BFP-Pdd) at 37° C. or BJ cell-derived iPS cells were infected with SeV18+BFP/LddTSΔF (BFP-Ldd) at MOI=5 and 1 μM of Shield1 was added thereto (day 0), Shield1 was removed on day 1, and observation was carried out on day 5. As a result, in the BFP-Pdd infected cells from which Shield1 was removed, blue fluorescence was reduced to about 18% as compared to the BFP-Pdd infected cells from which Shield1 was not removed (image analysis with ImageJ (NIH)) (FIG. 9). On the other hand, fluorescence of BFP-Ldd was weak even in the presence of Shield1 and a large change in expression regulation was also not observed (FIG. 10). The reconstitution efficiency of the SeV vector in the case of DD-tag addition to the L protein was lower than that in the case of DD-tag addition to the P protein. Furthermore, SeV producing cells expressing the P protein were easily obtained; however, SeV producing cells expressing the L protein were not easily obtained, and even if such SeV producing cells could be obtained, SeV productivity was low.

Example 11 pHSV-ddP-Halo and pHSV-Pdd-Halo were gene-transferred to HeLa cells using Lipofectamine LTX (Life Technologies), pulse labeling was carried out with an FAM ligand for 15 minutes in the presence of 1 μM of Shield1, and then degradation of the P protein was observed with a fluorescence microscope, using loss of fluorescence as an indicator. As a result, it was observed that degradation of the P protein started within ten minutes and the P protein was degraded within five hours (FIG. 11). Even when DD-tag was added to either of the N terminus side or the C terminus side of the P protein, the same degradation was shown.

Example 12

Reconstitution of SeV18+BFP/PddTS15ΔF, SeV18+GFP/PddTS15ΔF, SeV18+BFP/ddPTS15ΔF, and SeV18+GFP/ddPTS15ΔF was attempted using PF expressing cells. As a result, SeV18+BFP/PddTS15ΔF and SeV18+GFP/PddTS15ΔF in which DD-tag is added to the C terminus side of the P protein were obtainable, but SeV18+BFP/ddPTS15ΔF and SeV18+GFP/ddPTS15ΔF in which DD-tag is added to the N terminus side of the P protein were not obtainable. That is, it is shown that by adding DD-tag to the N terminus side of the P protein without supplying the C protein, the reconstitution efficiency of the SeV vector is reduced.

Example 13

HeLa cells were infected with SeV18+TIR1(HNL)d2AG/PaidTSΔF (d2AG-Paid) or SeV18+TIR1(HNL)d2AG/LaidTSΔF (d2AG-Laid) at MOI=5 at 37° C. (day 0), 500 μM of indole-3-acetic acid (IAA) as Auxin was added thereto on day 3, and then observation with a fluorescence microscope and FACS was carried out. As a result, a result that the median value was reduced from 149.89 to 126.35 in FACS was obtained with d2AG-Paid (FIG. 12), but a large change in expression regulation of d2AG-Laid was not observed. The reconstitution efficiency of the SeV vector in the case of aid addition to the d2AG-Paid L protein was reduced as compared to the case of aid addition to the P protein.

Example 14

HeLa cells were infected with SeV18+d2AG/PddTS15ΔF (d2AG-PddTS15) and SeV18+d2AG/TS15ΔF (d2AG-TS15) at MOI=5 at 32° C., 1 μM of Shield1 was added thereto (−day 3), and on day 0, removal of Shield1 and cell transfer to 37° C. were carried out or the cells were transferred to 35° C. while Shield1 was added. Then, temporal observation was carried out. As a result, in the d2AG-PddTS15 infected cells at 37° C. from which Shield1 was removed, fluorescence was lost on day 7, and higher fluorescence expression level than that of d2AG-TS15 was shown under the condition of 35° C. (FIG. 13). On the other hand, in d2AG-TS15 at 37° C., cells in which fluorescence was lost were observed on day 21, but remaining of fluorescence expression was observed (FIG. 13). When SeV antibody staining was carried out on day 14, d2AG-PddTS15 at 37° C. was negative for staining with the SeV antibody and d2AG-TS15 at 37° C. was positive for staining with the SeV antibody (FIG. 14). After d2AG-PddTS15 was infected at 32° C., the temperature was increased to 35 to 39° C. on day 2, and observation was carried out on day 5 from the infection. As a result, fluorescence expression was reduced at 35 to 39° C., and fluorescence expression was lost at 37 to 39° C. (FIG. 15).

Example 15

HeLa cells were infected with SeV18+d2AG/PddgTS15ΔF (d2AG-PddgTS15) at MOI=5 at 32° C., 20 μM of trimethoprim (TMP) was added thereto (day 0), and on day 3, removal of TMP and cell transfer to 37° C. were carried out or the cells were transferred to 35° C. while Shield1 was added. Then, temporal observation was carried out. As a result, in d2AG-PddgTS15 infected cells at 37° C. from which TMP was removed, loss of fluorescence was observed on day 6 from the infection (FIG. 16(*a*)). The decrease and loss in expression of the carried gene were observed at 35 to 39° C. (FIG. 16(*b*)). DD-tag was expressed at 35° C.; on the other hand, loss of expression was observed with ddg-tag.

Example 16

HeLa cells were infected with SeV18+d2AG/PtetRTS15ΔF (d2AG-PtetRTS15) at MOI=5 at 32° C., 1.5 μg/mL of DOX was added thereto (day 0), removal of DOX and cell transfer to 35 to 39° C. were carried out on day 2, and then observation was carried out on day 5 after the infection. As a result, fluorescence expression was reduced and lost at 35 to 39° C. (FIG. 17).

Example 17

HeLa cells were infected with SeV18+d2AG/d4PTS15ΔF (d2AG-d4PTS15) at MOI=5 at 32° C. (day 0), cell transfer to 35 to 39° C. was carried out on day 2, and then observation was carried out on day 5 after the infection. As a result, fluorescence expression was reduced at 35 to 39° C., and lost at 37 to 39° C. (FIG. 18).

Example 18

HeLa cells were infected with SeV18+d2AG/d2PTS12A (d2AG-d2PTS12), SeV18+d2AG/PddTS12ΔF (d2AG-PddTS12), and SeV18+d2AG/TS12ΔF (d2AG-TS12) at MOI=5 (day 0) (in the case of d2AG-PddTS12, 1 μM of Shield1 was added thereto at the time of infection), Shield1 was removed on day 3, cells were transferred to 37° C. after being cultured at 38.5° C. for five days or cells were transferred to 35° C. (in the case of d2AG-PddTS12 at 35° C., addition of Shield1 was maintained), and then observation was carried out on day 18 after the infection ("38.5° C. (5 day)" and "35° C." of FIG. 19, respectively). As a result, loss of fluorescence expression of d2AG-d2PTS12 and d2AG-PddTS12 was enhanced earlier than d2AG-TS12, and fluorescence expression of d2AG-PddTS12 was lost in a shorter time than d2AG-d2PTS12 (FIG. 19).

Example 19

Hela cells were infected with SeV18+d2AG/d2PTS15ΔF (d2AG-d2PTS15), SeV18+d2AG/d4PTS15ΔF (d2AG-d4PTS15), and SeV18+d2AG/TS15ΔF (d2AG-TS15) at MOI=5 at 32° C. (day 0) and cells were transferred to 37° C. or transferred to 35° C. on day 3. Then, temporal observation was carried out. As a result, in the d2AG-d2P15 and d2AG-d4P15 infected cells at 37° C., fluorescence was lost on day 7 (FIG. 20), and loss of fluorescence also was confirmed in FACS on day 13 (FIG. 21). On the other hand, in the d2AG-TS15 at 37° C., remaining of fluorescence on day 13 was observed (FIG. 21). Even by adding a degron, fluorescence of d2AG at 35° C. showed the same value as that of the conventional vector not added with a degron (FIG. 21).

Example 20

HeLa cells were infected with SeV18+d2AG/d2PTS15ΔF (d2AG-d2PTS15) and SeV18+d2AG/TS15ΔF (d2AG-TS15) at MOI=5 at 32° C. (−day 3), cell transfer to 37° C. was carried out on day 0, and then temporal observation was carried out. As a result, in the d2AG-d2PTS15 infected cells at 37° C., fluorescence was lost on day 7 (FIG. 22). On the other hand, in the d2AG-TS15 at 37° C., cells in which fluorescence was lost on day 21 were observed, but remaining of fluorescence expression was observed. Even by adding a degron, fluorescence of d2AG at 35° C. showed the same value as that of the conventional vector not added with a degron (FIG. 22).

Example 21

RNAs were collected from the cells of Examples 14 and 20, and RT-PCR and real-time PCR were carried out. Applied Biosystems 7500 Fast (Life Technologies) was used in the real-time PCR. Sequences described in WO 2012/029770 were used as the PCR primers for SeV and the PCR primer of beta-Actin. SeV-L (5'-CCGTAGTAAGAAAAACTTAGGGTGA-3') (SEQ ID NO: 87) and SeV-R (5'-GATCCATGCGGTAAGTGTAGC-3') (SEQ ID NO: 88) were used as the real-time PCR primer of SeV. Probe#3 of Universal ProbeLibrary (Roche) was used as a probe and Human GAPD (GAPDH) Endogenous Control (VIC/MGB Probe, Primer Limited) (Life Technologies) was used for GAPDH. In the HeLa cells on day 21, loss of SeV band of d2AG-d2PTS15 and d2AG-PddTS15 was observed, but SeV band was observed in d2AG-TS15 (FIG. 23). Similarly, also in the real-time PCR, loss of d2AG-d2PTS15 and d2AG-PddTS15 on day 21 was observed, but d2AG-TS15 was confirmed to remain on day 21 (FIG. 24). When RQ of PddTS15 on day 14 was regarded as 1, d2PTS15 and PddTS15 were not detected on day 21. On the other hand, TS15, a conventional vector, was gradually reduced, but remaining thereof was confirmed even on day 21. PddTS15 on day 3 showed a value higher than TS15 on day 3 by 30 times or more.

Example 22

CytoTune-iPS 2.0 (a combination of SeV(PM)KOS/TS12ΔF, SeV(HNL)cMYC/TS15ΔF, and SeV18+KLF4/TSΔF, available from Life Technologies or MEDICAL & BIOLOGICAL LABORATORIES CO., LTD.) or cMYC of CytoTune-iPS 2.0 was substituted with SeV(HNL)cMYC/d2PTS15ΔF (d2P-MYC), SeV(HNL)cMYC/PddTS15ΔF (Pdd-MYC), SeV(HNL)cMYC/PddgTS15ΔF (Pddg-MYC), or SeV(HNL)cMYC/PtetRTS15ΔF (PtetR-MYC) and then BJ cells were infected therewith at 32° C. (methods for producing iPS cells are specifically described in WO 2012/029770 and WO 2010/008054, KOS and KLF4 are at MOI=5, and cMYC is at MOI=1) (day 0), the cells were transferred to 37° C. on day 1 and seeded onto MEF on day 6, and staining for alkaline phosphatase (ALP) was carried out on day 28. 1-Step NBT/BCIP (Thermo Scientific) was used in ALP staining. The cells were passaged at 37° C., SeV antibody staining and real-time PCR using TaqMan Sendai Assay ID: Mr04269880_mr (Life Technologies), and PCR of NANOG and TERT that are reprogramming markers were carried out for each passage. Sequences described in WO 2012/029770 were used as the PCR primers for NANOG and TERT. As a result, it was confirmed that ALP positive colonies were formed in all vectors (FIG. 25). The efficiency of appearance of ALP positive colonies on day 30 when KOS and KLF4 were infected at MOI=10 and d2P-MYC was infected at MOI=5 was 0.5% or higher. As a result of carrying out SeV antibody staining, negativity for SeV antibody staining of d2P-MYC was confirmed with the number of passages at which SeV positive cells were observed with CytoTune-iPS 2.0 at P=2 (FIG. 26). As a result of the real-time PCR, it was confirmed that RQ of CytoTune-iPS 2.0 at P=1 was 1; on the other hand, d2P-MYC at P=1 was 1/16 or less, d2P-MYC at P=2 was 1/1500 or less, d2P-MYC was not detected at P=3, and loss of d2P-MYC was observed at timing earlier than that in the case of CytoTune-iPS 2.0 (FIG. 27). As a result of PCR of the reprogramming markers, regarding d2P-MYC at P=3, NANOG positivity, TERT positivity, and SeV negativity of the obtained iPS cells were observed in three strains #3, #5, and #6 (FIG. 28), and regarding Pdd-MYC, Pddg-MYC, and PtetR-MYC, NANOG positivity, TERT positivity, and SeV negativity were observed in each of two strains of the obtained iPS cells (FIG. 29). Furthermore, when the iPS cells obtained in FIG. 28 were transplanted to the NOD-scid mice, teratomas were formed, and three germ layer formation ability was observed by carrying out hematoxylin-eosin staining (FIG. 30).

Example 23

HeLa cells were infected with SeV18+d2AG/TS15ΔF (d2AG-TS15) and SeV18+d2AG/PtetRTS15ΔF (d2AG-PtetRTS15) (1.5 μg/ml of DOX was added in the case of d2AG-PtetRTS15) (day 0), removal of DOX and cell transfer to 35° C. were carried out on day 2, and then observation was carried out on day 5 after the infection. As a result, as compared to the case of infection with only d2AG-TS15 (referred to as TS15), it is shown that removal of the vector was enhanced to 60% by co-infection with d2AG-PtetRTS15 (referred to as TS15+PtetR) (FIG. 31). On the other hand, in the cells whose infection dose of d2AG-TS15 was increased two fold, fluorescence of d2AG was increased to 118%.

Example 24 pCAGGS-P4C(−) (WO 2005/071085), pCAGGS-d144P (d144P), pCAGGS-d307P (d307P), and pCAGGS-Pct (Pct) were gene-transferred to HeLa cells using TransIT-LT1 (Mirus Bio), and SeV18+GFP/TSΔP (WO 2008/133206) was infected at MOI=10 at 37° C. (day 0), and then observation with a fluorescence microscope was carried out on day 1. As a result, similarly to the cells to which pCAGGS-P was gene-transferred, in the cells into which d144P, d307P, and Pct were introduced, green fluorescence was also observed by infection of SeV18+GFP/TSΔP (FIG.

32). This indicates that even when the N terminus side of the P protein is chipped off, the P protein functions as the P protein.

Example 25 pEB-SeV-Pdd-Halo, pEB-MeV-Pdd-Halo, pEB-NDV-Pdd-Halo, pEB-PIV2-Pdd-Halo, and pEB-VSV-Pdd-Halo were gene-transferred to HeLa cells using TransIT-LT1 (Mirus Bio), pulse labeling was carried out with a TMR ligand for 15 minutes in the presence of 1 μM of Shield1, and then degradation of the P protein was observed with fluorescence microscope, using loss of fluorescence as an indicator. As a result, it was shown that the P protein of the negative-strand RNA viruses was rapidly degraded in one hour (FIG. 33). While the P protein of SeV was reduced to 12.1% in one hour, MeV, NDV, PIV2, and VSV were reduced to 6.1%, 6.8%, 10.2%, and 7.9%, respectively.

Example 26

BHK cells were infected with SeV(PM)ddgOFP(HNL) ddDGFP/d2PTS15ΔF (ddgOFP-ddDGFP-d2PTS15) at 32° C. (day 0), 1 μM of Shield1 or 1 μM of Shield1 and 20 μM of TMP were added thereto on day 2, and then observation with a fluorescence microscope was carried out on day 3. As a result, in the ddgOFP-ddDGFP infected cells added with Shield1, green fluorescence was observed, and in the ddgOFP-ddDGFP-d2PTS15 infected cells added with Shield1 and TMP, green fluorescence and orange fluorescence were observed (FIG. 34*a*).

Example 27

1 μM of Shield1 was added to Hela cells and SeV(PM) ddgOFP(HNL)ddDGFP/PddTS15ΔF (ddgOFP-ddDGFP-PddTS15) was infected at MOI=5 at 32° C. (day 0), 1 μM of Shield1 or 1 μM of Shield1 and 20 μM of TMP were added thereto on day 2, and then observation with a fluorescence microscope was carried out on day 3. After fluorescence observation, Shield1 and TMP were removed and the cells were transferred to 37° C. As a result, in the ddgOFP-ddDGFP-PddTS15 infected cells added with Shield1, green fluorescence was observed, and in the ddgOFP-ddDGFP infected cells added with Shield1 and TMP, green fluorescence and orange fluorescence were observed. In the cells in which Shield1 and TMP were removed and the cells were transferred to 37° C., loss of fluorescence was observed (FIG. 34*b*). This indicates that multiple carried genes are independently controlled by pharmaceutical agents and the vectors are removed by an increase in temperature.

Example 28

HeLa cells were infected with SeV18+DGFP/PddΔF (DGFP-Pdd/dF) at MOI=5 at 37° C. while adding or not adding 1 μM of Shield1 (day 0), observation with a fluorescence microscope was carried out on day 1, and fluorescence images were analyzed with MetaMorph (Molecular Devices). As a result, as compared to the DGFP-Pdd/dF infected cells added with Shield1, in the DGFP-Pdd/dF infected cells not added with Shield1, a reduction of fluorescence to 40% was observed (FIG. 35). This indicates that even in vectors not having a temperature-sensitive mutation, expression can be regulated by adding a degron to the P protein.

INDUSTRIAL APPLICABILITY

According to the present invention, it is possible to induce expression of the carried gene at a high level after introduction of the vectors, and then to rapidly remove the vectors. The present invention is useful for transiently expressing a transcription factor such as a reprogramming factor in a target cell and is expected to be applied to cell therapy and regenerative medical treatment.

The invention claimed is:

1. A Sendai viral vector comprising a nucleic acid sequence encoding an endogenous P protein operably linked on the C-terminus to a degron.

2. The Sendai viral vector of claim 1, wherein the P protein is a temperature-sensitive P protein.

3. The Sendai viral vector of claim 2, wherein said temperature-sensitive mutation comprises an L511F mutation.

4. The Sendai viral vector of claim 2, wherein said temperature-sensitive mutation comprises D433A, R434A, and K437A mutations.

5. The Sendai viral vector of claim 1, wherein the L protein of said virus comprises L1361C and L1558I mutations.

6. The Sendai viral vector of claim 1, wherein the degron is selected from the group consisting of mtor degron, dihydrofolate reductase (DHFR) degron, PEST, tetr degron, and auxin-inducible degron (AID).

7. The Sendai viral vector of claim 1, further comprising an exogenous nucleic acid sequence encoding an exogenous protein.

8. The Sendai viral vector of claim 7, wherein said exogenous protein is operably linked to a degron.

9. The Sendai viral vector of claim 8, wherein the degron operably linked to the exogenous protein is different from the degron operably linked to the P protein.

10. The Sendai viral vector of claim 1, further comprising a first exogenous nucleic acid sequence encoding a first exogenous protein operably linked to a degron, and a second exogenous nucleic acid sequence encoding a second exogenous protein, wherein the degrons operably linked to the first and second proteins are different from each other.

11. A composition comprising the Sendai viral vector of claim 1.

* * * * *